US012760281B2

(12) United States Patent
Chen et al.

(10) Patent No.: US 12,760,281 B2
(45) Date of Patent: Oct. 13, 2026

(54) CHIMPANZEE ADENOVIRUS VECTOR, CONSTRUCTION METHOD THEREFOR, AND APPLICATION THEREOF

(71) Applicant: JIAXING ANYU BIOTECHNOLOGY CO., LTD, Zhejiang (CN)

(72) Inventors: Ping Chen, Zhejiang (CN); Na Li, Zhejiang (CN); Tingting Zhang, Zhejiang (CN); Xintao Zhong, Zhejiang (CN); Zhigang Zhu, Zhejiang (CN); Nan Li, Zhejiang (CN)

(73) Assignee: JIAXING ANYU BIOTECHNOLOGY CO., LTD, Jiaxing (CN)

( * ) Notice: Subject to any disclaimer, the term of this patent is extended or adjusted under 35 U.S.C. 154(b) by 475 days.

(21) Appl. No.: 18/014,647

(22) PCT Filed: Jul. 6, 2021

(86) PCT No.: PCT/CN2021/104641
§ 371 (c)(1),
(2) Date: Jan. 5, 2023

(87) PCT Pub. No.: WO2022/007774
PCT Pub. Date: Jan. 13, 2022

(65) Prior Publication Data

US 2025/0066740 A1 Feb. 27, 2025

(30) Foreign Application Priority Data

Jul. 6, 2020 (CN) ......................... 202010642745.3
Sep. 10, 2020 (CN) ......................... 202010945335.6

(51) Int. Cl.
*C12N 7/00* (2006.01)
*A61K 39/00* (2006.01)
(Continued)

(52) U.S. Cl.
CPC ................ *C12N 7/00* (2013.01); *A61K 39/12* (2013.01); *C12N 15/86* (2013.01);
(Continued)

(58) Field of Classification Search
None
See application file for complete search history.

(56) References Cited

U.S. PATENT DOCUMENTS

2012/0027788 A1* 2/2012 Colloca .................. A61P 31/20
435/235.1
2025/0066740 A1* 2/2025 Chen .................... C07K 14/005

FOREIGN PATENT DOCUMENTS

CN 102844329 A 12/2012
CN 105112428 A 12/2015
CN 107723298 A 2/2018
CN 111108192 A 5/2020
CN 111363858 A 7/2020
WO WO2019076882 A1 4/2019

OTHER PUBLICATIONS

SEQ 7 alignment with Issued_Patents db U.S. Appl. No. 13/147,193 seq 39 Jul. 2011.*

(Continued)

*Primary Examiner* — Shanon A. Foley
(74) *Attorney, Agent, or Firm* — MUNCY, GEISSLER, OLDS & LOWE, P.C.

(57) ABSTRACT

A chimpanzee adenovirus vector from newly discovered and isolated chimpanzee adenovirus with unique HVR sequences and a method of its construction and application thereof, with higher viral titer, and provides a method for determining its viral titer. The chimpanzee adenovirus circular vector is constructed through a shuttle plasmid, and knocks out E1 and E3 to construct a replication-defective chimpanzee adenovirus vector. The chimpanzee adenovirus vector described in this article has no preexisting antibody in the population, and the knockout of E1 and E3 is safe. At the same time, it is significantly different from human adeno- (Continued)

virus type 5 E1 in 293 cells, which can greatly avoid recovery mutation (RCA) and make it safer. The novel coronavirus vaccine has strong stability and does not cause mutations after multiple passages, and it can induce strong humoral immunity and cellular response in mouse models.

4 Claims, 18 Drawing Sheets

Specification includes a Sequence Listing.

(51) Int. Cl.
*A61K 39/12* (2006.01)
*C12N 15/86* (2006.01)

(52) U.S. Cl.
CPC ................. *A61K 2039/5256* (2013.01); *C12N 2710/10321* (2013.01); *C12N 2710/10322* (2013.01); *C12N 2710/10334* (2013.01); *C12N 2710/10343* (2013.01); *C12N 2770/20022* (2013.01); *C12N 2770/20034* (2013.01)

(56) References Cited

OTHER PUBLICATIONS

SEQ 9 alignment with Issued_Patents db U.S. Appl. No. 13/147,193 seq 41 Jul. 2011.*
SEQ 10 alignment with Issued_Patents db U.S. Appl. No. 13/147,193 seq 38 Jul. 2011.*
SEQ 11 alignment with Issued_Patents db U.S. Appl. No. 13/147,193 seq 41 Jul. 2011.*
SEQ 12 alignment with Issued_Patents db U.S. Appl. No. 13/147,193 seq 41 Jul. 2011.*
SEQ 13 alignment with Issued_Patents db U.S. Appl. No. 13/147,193 seq 41 Jul. 2011.*
SEQ 14 alignment with Issued_Patents db U.S. Appl. No. 13/147,193 seq 41 Jul. 2011.*
Kim et al. "*COVID-19 vaccines: breaking record times to first-in-human trials*." NPJ Vaccines 5 (2020), 3 pgs.

* cited by examiner

Percent Identity

Divergence

| | 1 | 2 | 3 | 4 | 5 | 6 | 7 | 8 | 9 | 10 | 11 | 12 | 13 | | |
|---|---|---|---|---|---|---|---|---|---|---|---|---|---|---|---|
| 1 | | 78.1 | 76.5 | 77.9 | 100.0 | 39.4 | 74.1 | 73.9 | 73.9 | 73.9 | 72.6 | 70.4 | 61.6 | 1 | Simian adenovirus 21.seq |
| 2 | 26.1 | | 89.1 | 98.5 | 78.1 | 42.0 | 77.1 | 76.8 | 78.7 | 78.7 | 73.9 | 68.9 | 67.5 | 2 | Simian adenovirus 22.seq |
| 3 | 28.5 | 11.8 | | 89.0 | 76.5 | 40.9 | 77.1 | 76.1 | 77.8 | 77.8 | 74.2 | 69.4 | 61.2 | 3 | Simian adenovirus 23.seq |
| 4 | 26.4 | 1.6 | 11.9 | | 77.9 | 42.1 | 77.3 | 76.8 | 78.7 | 78.7 | 73.9 | 68.9 | 68.2 | 4 | Simian adenovirus 24.seq |
| 5 | 0.0 | 26.1 | 28.5 | 26.4 | | 39.4 | 74.1 | 73.9 | 73.9 | 73.9 | 72.6 | 70.4 | 61.6 | 5 | Simian adenovirus 25.seq |
| 6 | 124.5 | 111.9 | 116.7 | 111.4 | 124.5 | | 37.5 | 38.2 | 37.2 | 37.2 | 37.4 | 36.3 | 91.4 | 6 | Simian adenovirus 26.seq |
| 7 | 32.0 | 27.5 | 27.5 | 27.1 | 32.0 | 134.6 | | 84.7 | 81.1 | 81.1 | 77.8 | 71.8 | 56.2 | 7 | Simian adenovirus 2.seq |
| 8 | 32.3 | 27.9 | 29.0 | 27.9 | 32.3 | 130.7 | 17.3 | | 80.8 | 80.8 | 78.0 | 71.8 | 56.4 | 8 | Simian adenovirus 7.seq |
| 9 | 32.4 | 25.1 | 26.4 | 25.2 | 32.4 | 136.7 | 21.8 | 22.4 | | 100.0 | 75.9 | 72.0 | 49.8 | 9 | Simian adenovirus 8.seq |
| 10 | 32.4 | 25.1 | 26.4 | 25.2 | 32.4 | 136.7 | 21.8 | 22.4 | 0.0 | | 75.9 | 72.0 | 49.8 | 10 | Simian adenovirus 18.seq |
| 11 | 34.4 | 32.3 | 31.9 | 32.4 | 34.4 | 135.9 | 26.6 | 26.2 | 29.3 | 29.3 | | 74.1 | 54.2 | 11 | Simian adenovirus 19.seq |
| 12 | 38.0 | 40.7 | 39.7 | 40.6 | 38.0 | 142.7 | 35.6 | 35.7 | 35.3 | 35.3 | 32.1 | | 54.1 | 12 | Simian adenovirus 20.seq |
| 13 | 54.3 | 42.9 | 56.1 | 41.8 | 54.3 | 9.2 | 66.2 | 65.5 | 85.2 | 85.2 | 71.6 | 71.3 | | 13 | sAd-AY01.seq |
| | 1 | 2 | 3 | 4 | 5 | 6 | 7 | 8 | 9 | 10 | 11 | 12 | 13 | | |

FIG.4

1. psAd-shuttle: EcoRI/BamHI

CHIMPANZEE ADENOVIRUS VECTOR, CONSTRUCTION METHOD THEREFOR, AND APPLICATION THEREOF

CROSS-REFERENCE TO RELATED APPLICATIONS

The present application claims priority to a U.S. National Stage of International Application No. PCT/CN2021/104641 filed on Jul. 6, 2021, a Chinese prior application No. 202010642745.3 and filed on Jul. 6, 2020, and a Chinese prior application No. 202010945335.6 and filed on Jul. 6, 2020; the entire contents of PCT application PCT/CN2021/104641 are hereby incorporated by reference.

REFERENCE TO AN ELECTRONIC SEQUENCE LISTING

The contents of the electronic sequence listing (Substitute Sequence Listing.txt; Size: 174,474 bytes; and Date of Creation: Jul. 11, 2023) is herein incorporated by reference in its entirety.

TECHNICAL FIELD

The invention relates to the technical field of genetic engineering and the field of immunology, in particular to a novel chimpanzee adenovirus vector and a construction method and application thereof.

BACKGROUND TECHNOLOGY

Adenovirus is a common virus causing upper respiratory tract and lung diseases, and the human immune system will have a strong immune response to adenovirus. Therefore, it is necessary to transform adenovirus into harmless vaccine vector. After decades of research and development, human adenovirus type 5 vaccine vector is widely used. Adenovirus is very popular as vaccine virus, usually, the adenovirus vector used in gene therapy is mainly human adenovirus type 5 (AdHu5), but neutralizing antibodies against AdHu5 are common in the population, and about one third of the population has become immune to it in adulthood. The immune system of these populations will destroy vaccines instead of producing antibodies against viruses carrying inserted genes. Moreover, the Hexon protein of AdHu5 binds to coagulation factor X (FX) in blood, which leads to the accumulation of adenovirus in liver and affects the tumor targeting of AdHu5. Therefore, the efficacy and targeting of adenovirus type 5 need to be further improved and perfected.

Chimpanzee adenovirus provides us with another feasible method. Because chimpanzee adenoviruses such as AdC7 and AdC23 are rarely prevalent in people, there are generally no corresponding neutralizing antibodies in people, and they will not be neutralized by antibodies against human adenovirus type 5 (AdHu5). At the same time, Hexon protein of chimpanzee adenovirus does not bind to FX. Therefore, chimpanzee adenovirus vector can be developed into an ideal adenovirus vector platform, which can be used to prepare higher quality vaccine reagents, such as Novel Coronavirus vaccine, and maintain inherent safety.

COVID-19, which began to break out in large numbers all over the world in 2019, caused serious diseases and caused huge losses. Coronavirus is a large virus family, which is known to cause colds and more serious diseases such as Middle East Respiratory Syndrome (MERS) and Severe Acute Respiratory Syndrome (SARS). Novel Coronavirus is a new strain of coronavirus that has never been found in humans before.

Novel Coronavirus expressed 29 proteins, of which 16 were related to its replication, and 4 were structural proteins, Spike protein (S protein), Nucleocapsid protein (N protein) and Envelope protein (E protein). S protein is the most important surface protein of coronavirus. S protein can bind to human ACE2 (host cell receptor angiotensin converting enzyme 2), and its affinity is much higher than that of severe acute respiratory syndrome coronavirus (SARS-COV). S protein is the key to enter cells and the target of antibody drugs. N protein is abundant in coronavirus, which is a highly immunogenic protein and participates in genome replication and cell signaling pathway regulation.

The antibodies in novel coronavirus pneumonia patients will disappear within a few months, and so may the antibodies provided by vaccines, which means that people can't get vaccinated once and for all, and the antibodies will fade in a short time. The sooner or later of fading depends on the antibody level at the highest point, which determines how long the antibodies can stay in the body. Therefore, how to improve the antibody level of novel coronavirus pneumonia virus in patients is the primary problem to be considered in preparing Novel Coronavirus vaccine.

After testing, the serum of the population does not contain the pre-stored antibody of chimpanzee adenovirus, so the immune system will not destroy the vaccine, which is conducive to the effective expression of the target antigen and improve the level of antibody. Therefore, chimpanzee adenovirus is a good platform as a vaccine vector. The titer of chimpanzee adenovirus is generally low, and the process of constructing vaccine vector is complex and difficult to be industrialized. Therefore, it is urgent to find a chimpanzee adenovirus vector with higher titer and form a complete process platform, which can be used for the preparation of various vaccines such as Novel Coronavirus vaccine.

SUMMARY OF THE INVENTION

To solve traditional problems, the invention provides a brand-new chimpanzee adenovirus with higher virus titer. The defective chimpanzee adenovirus vector prepared by the invention can be used for preparing various vaccines such as Novel Coronavirus vaccine. The chimpanzee adenovirus vaccine vector provided by the invention has no preexisting antibody in the population, and the E1 region of the novel chimpanzee adenovirus vector is very different with the E1 region of human adenovirus type 5 in 293 cells, which can greatly avoid recovery mutation; at the same time, the novel chimpanzee adenovirus vector has the characteristics of higher stability, and can induce strong humoral immunity and cellular response in mouse model.

One of the first aspects, the present invention provides a new chimpanzee adenovirus comprising a hyper variable region HVR, and the hyper variable region HVR comprises a nucleotide sequence represented by any one or more of sequence represent by SEQ ID NO. 9, SEQ ID NO. 10, SEQ ID NO. 11, SEQ ID NO. 12, SEQ ID NO. 13, or SEQ ID NO. 14 or a nucleotide sequence having more than 50% homology with the above sequences including SEQ ID NO. 9, SEQ ID NO. 10, SEQ ID NO. 11, SEQ ID NO. 12, SEQ ID NO. 13, or SEQ ID NO. 14.

Human adenoviruses belong to adenoviridae and mammalian adenoviruses. Up to now, 52 serotypes of human adenoviruses have been isolated, belonging to a ~G7 subgenera. At present, virus isolation technology, antibody detection technology and molecular biology technology (such as polymerase chain reaction, restriction fragment length polymorphism analysis technology, in situ hybridization technology, real-time fluorescence quantitative PCR technology) are mainly used in the diagnosis and typing of adenovirus infection.

Chimpanzee adenovirus also has different serotypes; it's gene sequence includes the sequence of hypervariable region HVR1-9 and relatively conservative sequence. The relatively conservative sequence can be used to distinguish different adenoviruses (such as chimpanzee adenovirus or human adenovirus), while the hypervariable region sequence can be used to distinguish different serotypes of adenoviruses, that is to say, the sequence of hypervariable region determines the specific serotype of adenovirus.

The sequence diagram of HVR1-9 is shown in FIG. 1. There are 9 regions in the hypervariable region. The different nucleic acid sequences of these hyper variable regions, thus the different expressed proteins or structures, determine the different serotypes of viruses. Generally, the hyper variable region of adenovirus has 9 regions, and the arrangement of these 9 regions is shown in FIG. 1. The so-called "serotype" means that in microbiology, it can be used to identify different types of microorganisms of the same kind, which can usually be detected by serological methods, which is called serotype. For example, the serotype of *Streptococcus* is determined mainly by titration titer of O antigen and H antigen.

The gene sequence of the novel chimpanzee adenovirus provided by the invention is mainly based on the sequence of the hexon gene hypervariable region HVR1-6 of the new chimpanzee adenovirus. The sequence of each region in the sequence of the hexon gene hypervariable region HVR1-6 of the chimpanzee adenovirus provided by the present invention is completely or significant different from the sequence of the serotype HVR1-6 of the known chimpanzee adenovirus in the database (GenBank™). The HVR1-6 sequence of the hexon gene hypervariable region of the new chimpanzee adenovirus comprises six mutation sequences respectively located in each sequence of the HVR1-6 sequence: HVR1 is the sequence indicated by the sequence number SEQ ID NO. 9, HVR2 is the sequence indicated by the sequence number SEQ ID NO. 10, HVR3 is the sequence indicated by the sequence number SEQ ID NO. 11, HVR4 is the sequence indicated by the sequence number SEQ ID NO. 12, HVR5 is the sequence indicated by the sequence number SEQ ID NO. 13, and HVR6 is the nucleotide sequence indicated by the sequence number SEQ ID NO. 14. The sequence of the adenovirus of the present invention at the position of HVR7-9 in the hypervariable region is not mutated, as shown in the sequence SEQ ID NO. 15.

The person with ordinary skill in the present invention will appreciate that the sequences of these hypervariable regions, once published, may be modified, artificially synthesized, or other unrelated sequences added to these sequences. These sequences, which have been modified, artificially synthesized, or added to 3 or 5 segments of the sequences consolidated by the invention, Thus forming a new sequence, Although these new sequences are not 100% the same as those published in the present invention, However, the scope of the present invention can still cover sequences having homology with the sequences of the above hypervariable regions 1-6, These new sequences are also within the scope of protection of the present invention, where the new sequence homology may be a sequence homology of a region in a single hypervariable region, for example, a sequence having more than 50% homology with the sequence shown in sequence number Seq ID NO. 9, for example, 55%, 60%, 65%, 70%, 75%, 80%, 85%, 88%, 90%, 95%, or 99%. In addition, sequences such as those having 50% homology with the sequences one of the hypervariable regions 1-6 of the present invention, such as 55%, 60%, 65%, 70%, 75%, 80%, 85%, 88%, 90%, 95%, or 99%, are also possible, and these sequences are also one of the scope of the present invention. In addition, if the sequence of the present invention or the protein sequence encoded by the sequence having more than 50% homology with the sequence of the present invention can be encoded, it is also within the scope of protection of the present invention, that is, the protein or amino acid sequence encoded by these sequences is also within the scope of protection of the present invention.

Of course, these new sequences may include one or more of the nucleic acid sequences in the hypervariable regions of the invention, for example it includes one or more of the nucleic acid sequences shown in hypervariable regions 1-6, the latter comprising sequences having more than 50% homology with each of the nucleic acid sequences in the hypervariable regions 1-6 of the invention, for example 55%, 60%, 65%, 70%, 75%, 80%, 85%, 88%, 90%, 95%, or 99% homology.

Further, in some embodiments, the adenovirus comprises a region of the hypervariable region HVR7-9 having a nucleotide sequence as shown in the sequence as presented by SEQ ID NO. 15.

Further, the hypervariable region HVR has a nucleotide sequence as shown in the sequence SEQ ID NO. 7, or a nucleotide sequence having more than 50% homology with this sequence.

Further, the hypervariable region HVR has a nucleotide sequence as shown in the sequence SEQ ID NO. 7, or a nucleic acid sequence having 55%, 60%, 65%, 70%, 75%, 80%, 85%, 88%, 90%, 95%, or 99% homology therewith.

Further, the chimpanzee adenovirus also includes a conserved region.

On the second aspect, the invention provides a chimpanzee adenovirus, which has a preservation number of CCTCC NO: V202120 and the name is sAd-AY01, which was preserved at the China Center for Type Culture Collection (CCTCC) on Apr. 25, 2021 at the address: Wuhan University, Wuhan City, 430072, China.

In some ways, the present invention provides an adenovirus comprising a nucleotide sequence as shown in the sequence table Seq ID NO. 1, or a sequence having more than 50% homology with the sequence.

The invention provides a brand-new chimpanzee adenovirus. The whole genome of the chimpanzee adenovirus genome DNA is sequenced to determine the final virus genome sequence. The chimpanzee adenovirus was deposited in the China Center for Type Culture Collection (CCTCC) on Apr. 25, 2021. It was classified as orangutan adenovirus name as sAd-AY01, the collection number was CCTCC NO: V202120, and the collection address was Wuhan University, Wuhan, 430072, China. The genome of this new chimpanzee adenovirus sAd-AY01 is 36687 bp.

The brand-new chimpanzee adenovirus provided by the invention, It has a hypervariable region HVR sequence completely different from the existing inhibitory serotype. Compared with the known chimpanzee adenovirus partial serotype HVR1-6 sequence, monkey adenovirus partial serotype HVR1-6 sequence and human adenovirus partial serotype HVR1-6 sequence in gene bank, the homology is between 49% and 91%.

Based on the sequence of HVR1-6 in the hypervariable region of its hexon gene, it is compared with the known chimpanzee adenovirus partial serotype HVR1-6 sequence, monkey adenovirus partial serotype HVR1-6 sequence and human adenovirus partial serotype HVR1-6 sequence in GenBank™, the homology is between 49% and 91%. The phylogenetic tree was constructed by DNAstar software (FIG. 5-2), and the homology and difference of sequences were analyzed by ClustalW calculation method. The adenovirus sequence with the largest homology was part of the gene of Pan troglodytes adenovirus clone 17.2 major capsid protein gene (GenBank™: MF176134.1), and the largest homology was 91.63%. Finally, it was determined that the chimpanzee adenovirus was a new adenovirus that had not been discovered.

Since the discovery and successful isolation of adenoviruses in 1950s, more than 100 serotypes have been found one after another, among which there are at least 52 human adenoviruses, which are divided into seven subgroups: A, B, C, D, E, F and G. Human adenoviruses type 2 and type 5 commonly used in gene therapy belong to subgroup C in serological classification, and have 95% homology in DNA sequence. According to blood cell agglutination characteristics for chimpanzee adenovirus, twenty-two virus strain have been divided into three categories, each virus strain has an adenovirus complement immobilized antigen (Hillis W D, Goodman R (1969) Serological classification of chimpanzee adenoviruses by hemagglutination and hemagglutination inhibition), the type-specific epitopes of adenovirus that can be recognized by neutralizing antibodies are mainly located on the hexon surface. The epitopes of hexon protein are plotted into two loops, L1 and L2, and are divided into seven hypervariable regions, HVR1-6 (L1) and HVR7 (L2). The hypervariable regions can lead to abnormal recombination. In most cases, HVR1-6 sequence sequencing can obviously distinguish serotypes. Molecular typing based on the hexon gene HVR1-7 and the discovery of new adenovirus variants have been widely used. (Casas A, Avellon M, Mosquera O, et al. Molecular typing of human adenoviruses by PCR and sequencing of a partial region of the hexon gene. Lu X, Erdman D D. Molecular typing of human adenoviruses by PCR and sequencing of a partial region of the hexon gene. Arch Viro 1, 2006, 151:1587-1602).

According to the reference of Complete nucleotide sequences and genome organization of four chimpanzee adenoviruses, chimpanzee adenovirus serotypes SAdV-22, SAdV-23, SAdV-24 (simian adenovirus 22, simian adenovirus 23, simian adenovirus 24) were classified into subtype E (as shown in FIG. 5-1). The homology between simian adenovirus 22 and simian adenovirus 26 was 91.1%, the homology between simian adenovirus 24 and simian adenovirus 26 was 91.2%, simian adenovirus 22 and simian adenovirus 26 was 91.2%, and simian adenovirus 22 and Simian adenovirus 24 has a homology of 98.5%. According to the references, the sequences were aligned. Using DNAStar Megalign software and ClustalW algorithm, the reference sequences were synchronously aligned to construct a phylogenetic tree. Our serotype sAd-AY01 belongs to the same subtype as SAdV-22, SAdV-23 and SAdV-24 in references-subtype E, and is a new chimpanzee adenovirus.

The highest homology with the orangutan adenovirus sAd-AY01 provided by the invention is Pan troglodytes adenovirus clone 17.2 major capsid protein gene and Pan troglodytes adenovirus clone 17.2 major capsid protein gene. The two known chimpanzee adenoviruses are not preserved by any preservation institution at present, and only 2000 bp sequences are disclosed.

The inventor has proved through a large number of studies that the novel chimpanzee adenovirus sAd-AY01 provided by the invention has very high virus titer, and the virus titer can reach $5\times10^8$ FFU/mL, which is far higher than the virus titer of the existing chimpanzee adenovirus and human adenovirus.

On the third aspect, the invention provides a new chimpanzee adenovirus vector psAd. The chimpanzee adenovirus vector psAd containing a HVR sequence in a hypervariable region is prepared by constructing a shuttle plasmid psAd-shuttle and carrying out homologous recombination with the chimpanzee adenovirus gene as described above after linearization.

In some embodiments, the plasmid contains a fluorescent labeled nucleic acid or a nucleic acid containing a fluorescent protein; the shuttle plasmid psAd-shuttle has a nucleotide sequence as shown in the sequence SEQ ID NO. 3, including replicon (pACYC), resistance gene (kanamycin), green fluorescent expression frame (RSV promoter, EGFP, BGHpolyA) nucleic acid.

In some embodiments, the cyclic plasmid psAd has a nucleotide sequence as shown in the sequence SEQ ID NO. 2, including a replicon (pACYC), a resistance gene (kanamycin), and a green fluorescent expression box (RSV promoter, EGFP, BGHpoly A) nucleic acid.

The chimpanzee adenovirus (sAd) genome is a linear DNA larger than 36 kb in length, which is difficult to edit effectively. Therefore, it is necessary to connect the replication-related elements in bacteria, such as replicon (pACYC) and resistance gene (kanamycin), to the chimpanzee genome to form a circular plasmid.

The existing method of constructing cyclic plasmid is usually cosmid (phage), which needs to buy corresponding kits, and phage may also pollute the laboratory.

Shuttle plasmids are usually used as expression vectors to carry genes to be expressed into target plasmids. The invention creatively constructs a chimpanzee adenovirus vector ring plasmid by constructing a shuttle plasmid psAd-shuttle comprising a replicon (pACYC), a resistance gene (kanamycin), a green fluorescent expression frame (RSV promoter, EGFP, BGHpolyA), and then carries out homologous recombination with the chimpanzee adenovirus genome after linearization to form a chimpanzee ring plasmid, which can effectively replicate in bacteria; at the same time, in order to monitor the transfection efficiency of plasmid in cells, green fluorescent expression frames (RSV promoter, EGFP, BGHpolyA) were added, and the transfection efficiency of vector could be judged by the amount of fluorescence in TP0 generation after transfection into cells. It can be understood that these are not necessary for shuttle plasmids, such as resistance gene (kanamycin), green fluorescent expression box (RSV promoter, EGFP, BGHpolyA), and of course, green fluorescent expression box (RSV promoter, EGFP, BGHpoly A) is the least necessary.

The method for constructing the circular plasmid of the invention has the advantages that: 1, no need to purchase a reagent kit and avoid the possible contamination of the laboratory by using bacteriophage; 2. The transfection efficiency of TP0 can be tested by adding EGFP fluorescence sequence; 3. It is more flexible and can build the components it needs according to its own needs.

In yet another aspect, the present invention provides a replication-defective chimpanzee adenovirus vector based on the chimpanzee adenovirus described above, conserved region deletion gene.

It can be understood that on the basis of the circular plasmid prepared by the chimpanzee adenovirus sAd-AY01 provided by the invention, the replication-defective chimpanzee adenovirus vector can be prepared by deleting any gene.

In some ways, the deletion gene is associated with chimpanzee adenovirus replication, and the vector after deletion of the gene is a replication-deficient chimpanzee adenovirus vector.

In some ways, the deletion gene includes any one or more of E1, E2A, E2B, E3, E4. For example, deletion of one of E1, E2A, E2B, E3 and E4 regions, or deletion of any combination of multiple regions, such as E1 and E3; E1, E3 and E4; E1, E2A, E3 and E4; E1, E2A, E2B, E3, E4 and so on.

As shown in FIG. 2, the conserved region genes of the chimpanzee adenovirus vector provided by the present invention include E1, E2A, E2B, E3 and E4.

In some embodiments, replication-defective chimpanzee adenovirus vectors are missing genes in the E1 and E3 regions.

In some embodiments, replication-deficient chimpanzee adenovirus vectors can be constructed by deleting E2A, E2B and E4 regions in addition to E1 and E3 regions.

In some embodiments, the E1 and E3 genes are deleted and have a nucleotide sequence as shown in the sequence SEQ ID NO. 4.

Further, the invention provides a replication-defective chimpanzee adenovirus vector psAd ΔE1 ΔE3, which is based on the chimpanzee adenovirus described above, knocks out its E1 and E3 genes to obtain a chimpanzee adenovirus vector psAd ΔE1Δ E3 deletion of E1 and E3 genes.

The replication-defective chimpanzee adenovirus vector comprises the sequence of the hypervariable region, the sequence of one region of the latter's six adjacent hypervariable regions or the region represented by a plurality of sequences.

The replication-deficient chimpanzee adenovirus vector psAdΔ E1Δ E3 has a nucleotide sequence as shown in the sequence SEQ ID NO. 4.

Wild-type chimpanzee adenovirus vector can replicate and amplify in ordinary cells. In application, this vector needs to lack its replication-related elements, and construct replication-deficient adenovirus vector, so that it can only replicate and package in specific complementary cell lines, but cannot replicate and package in ordinary cells. Therefore, the invention specifically knocks out the E1 and E3 genes of the chimpanzee adenovirus vector psAd, so that it can only be packaged in a specific cell line (such as the 293 cell line) and named as psAdΔ E1Δ E3. It will be understood that the adenovirus of the present invention also knocks out other sites, or adenoviruses with deletions of other sites, such as deletions of E2A, E2B, E4 sites, to obtain replication-defective adenovirus vectors.

In another aspect, the invention provides a method for constructing a replication-defective chimpanzee adenovirus vector, comprising the following steps:

(1) constructing the shuttle plasmid psAd, and carrying out homologous recombination with the chimpanzee adenovirus gene described in any one of the foregoing embodiments after linearization; Preferably, the shuttle plasmid comprises a fluorescent labeled cyclic plasmid psAd;

(2) knocking out the E1 gene of psAd to obtain the chimpanzee adenovirus vector psAdΔE1 with deletion of E1 gene; optionally, the enzyme cutting site, such as the enzyme cutting site PsiI; is introduced;

(3) the chimpanzee adenovirus vector psAdΔE1ΔE3 was obtained by knocking out the E3 gene of psAdΔE1.

Further, the shuttle plasmid psAd-shuttle in step 1) has a nucleotide sequence as shown in the sequence SEQ ID NO. 3, and the cyclic plasmid psAd has a nucleotide sequence as shown in the sequence SEQ ID NO. 2.

Further, in step 2), the E1 gene of psAd is digested by CRISPR/Cas9 enzyme, and an HRPT sequence containing a PsiI enzyme digestion site is inserted, and then purified and linked to obtain psAdΔE1; the HRPT sequence has a nucleotide sequence as shown in the sequence SEQ ID NO. 5.

Further, step 3) through CRISPR/Cas9 enzyme digesting psAdΔE1, the obtained product and the fusion fragment pVIII-U-exon are seamlessly cloned to obtain psAdΔE1ΔE3; the fusion fragment pVIII-U-exon has a nucleotide sequence as shown in the sequence SEQ ID NO. 6.

Shuttle plasmids are widely used in the construction of adenovirus vectors, and it is necessary to find a single enzyme cleavage site. The invention creatively adopts CRISPR/cas9 to construct recombinant adenovirus vector, selects appropriate E1, E3, E4 and E2A knockout sites through comparison, selects CRISPR sites according to the positions of E1, E3, E4 and E2A sequences and the number of knockout gene bases, and designs the best gRNA, thereby completing the construction of recombinant adenovirus vector.

In yet another aspect, the present invention provides a vaccine comprising a target gene in a gene deletion region of the replication-defective chimpanzee adenovirus vector as described above.

It can be understood that the nucleic acid sequence inserted into the deletion region can be any nucleic acid sequence, such as infectious disease, tumor and the like, which can be obtained or expressed by the vector to prepare vaccine reagents.

In some embodiments, the gene deletion region includes any one or more of E1, E2A, E2B, E3, E4.

In some embodiments, the target gene is a virus, a bacterium, a tumor gene or a gene fragment.

In some embodiments, the target gene is the Novel Coronavirus S gene.

In some embodiments, the gene of interest is located in the E1 region of a defective chimpanzee adenovirus vector, which is shown to have a nucleotide sequence as shown in sequence SEQ ID NO. 4.

In some embodiments, the invention provides a novel coronavirus vaccine, which is obtained by constructing a recombinant chimpanzee adenovirus vector expressing novel Coronavirus S gene and packaging it with 293 cells; The S gene is expressed in the E1 region of the defective chimpanzee adenovirus vector as described above to form a recombinant adenovirus vector psAd-S.

In another aspect, the invention provides a construction method of a recombinant chimpanzee adenovirus vector expressing novel Coronavirus S gene, comprising the following steps:

(a) constructing the E1 region shuttle plasmid pSsAdE1 of the chimpanzee adenovirus vector as described above;

(b) adding WPRE element to shuttle plasmid pSsAdE1 to obtain pSsAdE1-WPRE element;

(c) construction of shuttle plasmid pSsAdE1-WPRE-S expressing complete S protein gene of COVID-19 in Novel Coronavirus;

(d) homologous recombination of shuttle plasmid pSsAdE1-WPRE-S and adenovirus vector plasmid psAd ΔE1ΔE3 formed recombinant adenovirus vector psAd-S.

Further, the WPRE element is shown to have a nucleotide sequence as shown in the sequence SEQ ID NO. 17.

In another aspect, the present invention provides a titer determination method of recombinant chimpanzee adenovirus, which detects the titer of chimpanzee adenovirus by detecting the change of HVR antigen epitope of hypermutant region by specific antibody prepared from hexon hypermutant region HVR gene fragment, said HVR gene having nucleotide sequence as shown in sequence SEQ ID NO. 7.

Further, the chimpanzee adenovirus is the chimpanzee adenovirus as described above, or the replication defective chimpanzee adenovirus vector, or the vaccine as described above, or any recombinant chimpanzee adenovirus vector, etc.

The novel chimpanzee adenovirus of the invention is quite different from the traditional human type 5 adenovirus and the traditional chimpanzee adenovirus. After detection, the titer detection of the chimpanzee adenovirus of the invention needs to prepare its unique antibody. The main coat proteins of the new chimpanzee adenovirus are hexon, penton and fiber, and the hypervariable region HVR of hexon is the key region to identify the serotype of adenovirus. Therefore, expressing HVR protein and preparing mouse serum can detect the titer of chimpanzee adenovirus.

The detection method of chimpanzee adenovirus titer provided by the invention can be used for detecting the titer of recombinant chimpanzee adenovirus psAd-S vaccine provided by the invention.

In another aspect, the invention provides a packaging method of a recombinant chimpanzee adenovirus vector, wherein the vector of psAd-S was digested with I-sceI enzyme, 293 cells were transfected with the linearized plasmid, and cell suspension was collected.

The beneficial effects of the invention are mainly embodied in:

(1) a new chimpanzee adenovirus is provided, and the virus titer can reach 5×10^8 FFU/ml;

(2) creatively constructed chimpanzee adenovirus ring vector through shuttle plasmid;

(3) the invention provides a brand-new construction method of CRISPR/cas9 of recombinant chimpanzee adenovirus vector, independently designs the best knockout site and gRNA, avoids the trouble of finding a single enzyme cutting site when shuttle plasmid knockout is used in vector construction in the past, and the construction method is simple, efficient and short in cycle;

(4) it provides a brand-new replication-deficient chimpanzee adenovirus vector, which has no pre-existing antibodies in the population. At the same time, the E1 is very different from the E1 of human adenovirus type 5 in 293 cells, which can greatly avoid recovery mutation (RCA), the knockout of E1 and E3 make the chimpanzee adenovirus vector more safe;

(5) A new titer determination method of chimpanzee adenovirus is provided.

(6) After dozens of generations of passages, the constructed Novel Coronavirus vaccine is stability and have no mutation;

(7) The constructed Novel Coronavirus vaccine can induce strong humoral immunity and cellular response in mouse model.

ILLUSTRATED DRAWINGS

FIG. 4 is the results of comparison of the HVR1-6 sequence of the chimpanzee adenovirus sAd-AY01 in example 2 with the HVR1-6 sequence of some known serotypes.

FIG. 5-1 is schematic diagram of chimpanzee adenovirus serotyping in references.

FIG. 5-2 is schematic diagram of the process of constructing a phylogenetic tree analysis sequence of the HVR1-6 sequence of chimpanzee adenovirus sAd-AY01 and the known serotype HVR1-6 sequence in Example 2.

DETAIL OF EMBODIMENTS

Preferred embodiments of the invention are described in further detail below in conjunction with the accompanying drawings and it should be noted that the embodiments described below are intended to facilitate understanding of the invention without any limiting effect thereon.

Example 1 Isolation of a Novel Chimpanzee Virus Strain

Anal swabs from chimpanzees were collected, and chimpanzee adenovirus was cultured by HEK293 cells (purchased from ATCC, batch number 70009859).

Figure 3:
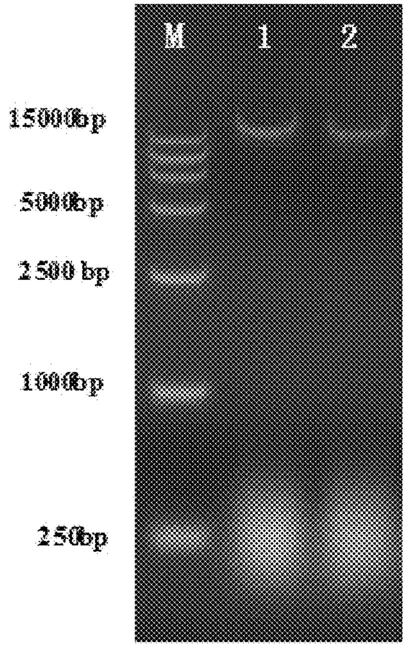
FIG. 3 is the results of the agarose gel electrophoresis confirmation of the genomic DNA sequence of the chimpanzee adenovirus in example 1, where M: 15000 bp Marker; 1, 2: Chimpanzee adenovirus genomic DNA.

First, the collected anal swab is melted on ice. Until room temperature, Put it in a 5 ml cryopreservation tube, Add 3 ml DMEM, Vortex 30s, 4° C., 2000 rpm, Centrifuge for 5 min, The supernatant is filtered through a 0.2 um pinhole filter membrane for about 200 um into a sterile 48-well plate for later use, Then inoculate HEK293 cells with 48 wells prepared in advance, and observe their pathological changes every day. If the cells are full in 48 hours, collect the cell suspension, freeze and thaw twice, and then freeze at −20° C. If it is not full, collect the cell suspension on the 5th day, and continue to inoculate HEK293 cells until the pathological changes, and extract the virus genome for PCR amplification and identification. The Hirt Virial DNA Extract method was used to further expand the identified virus strains (the main steps were collecting 3.5 ml infected cells, freezing and thawing for 3 times, adding 20% SDS 87.5 ul, 20 mg/ml Proteinase K 87.5 ul, incubating at 55° C. for 4 h; Add 1 ml of 5 mol/L NaCl solution into the centrifuge tube dropwise, mix well, incubate at 55° C. for 4 h; Chimpanzee adenovirus genome was extracted with phenol: chloroform: isoamyl alcohol (25:24:1) and chloroform: isoamyl alcohol (24:1). The upper water phase was extracted by adding 1/10 volume of 3 mol/L NaAc and 2 times volume of absolute ethanol at −20° C. for 30 min, centrifuging at 4° C. at 12,400 r/min for 5 min, slowly discarding the supernatant, naturally drying the residual alcohol, and then adding 50 μL Elution Buffer to dissolve DNA. The genomic DNA sequence of chimpanzee adenovirus was confirmed by agarose gel electrophoresis, and the results are shown in FIG. 3, where M: 15000 bp Marker; 1, 2: Genomic DNA of chimpanzee adenovirus, and the sequence larger than 15000 bp is the genome of chimpanzee adenovirus.

Example 2 Classification of Novel Chimpanzee Adenoviruses

The chimpanzee adenovirus genome DNA obtained in Example 1 was sequenced in the whole genome, and Shenggong Bioengineering (Shanghai) Co., Ltd. was responsible for determining the final virus genome sequence. The chimpanzee adenovirus was deposited in the China Center for Type Culture Collection (CCTCC) (Address: Wuhan University, Wuhan, 430072, China), classified and named as orangutan adenovirus sAd-AY01, and the preservation number was CCTCC NO: V202120. The genome of orangutan adenovirus sAd-AY01 is 36687 bp.

Human adenoviruses belong to adenoviridae and mammalian adenoviruses. Up to now, 52 serotypes of human adenoviruses have been isolated, belonging to a ~G7 subgenera. At present, virus isolation technology, antibody detection technology and molecular biology technology (such as polymerase chain reaction, restriction fragment length polymorphism analysis technology, in situ hybridization technology, real-time fluorescence quantitative PCR technology) are mainly used in the diagnosis and typing of adenovirus infection.

Figure 1:
FIG. 1 is schematic diagram of HVR1-9 sequence of chimpanzee adenovirus gene hypervariable region.
Figure 2:
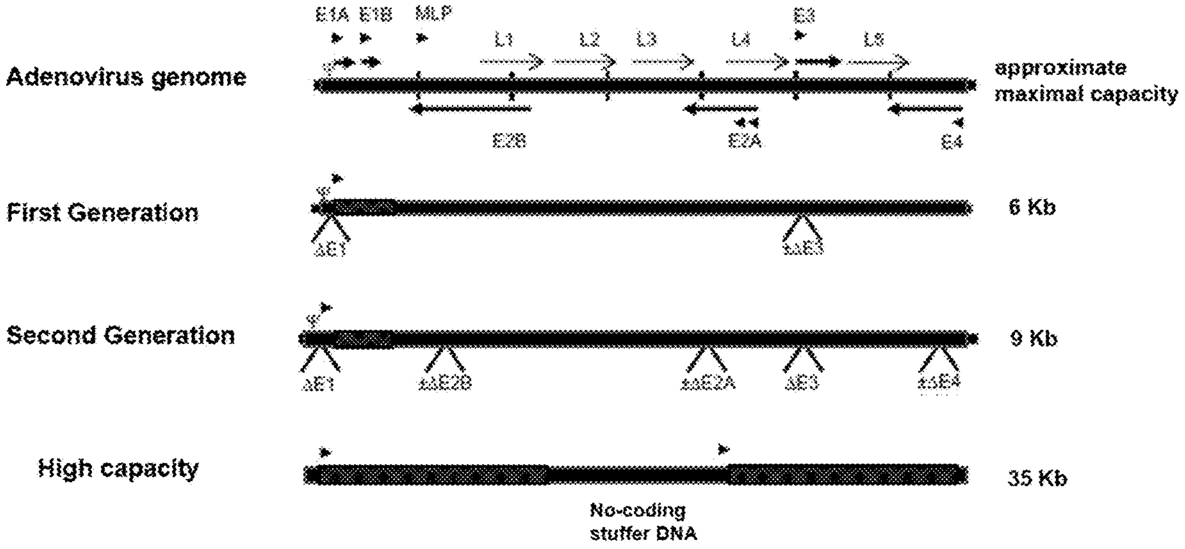
FIG. 2 is schematic diagram of E1, E2A, E2B, E3 and E4 regions of chimpanzee adenovirus gene conserved region.
Figures 1, 5:
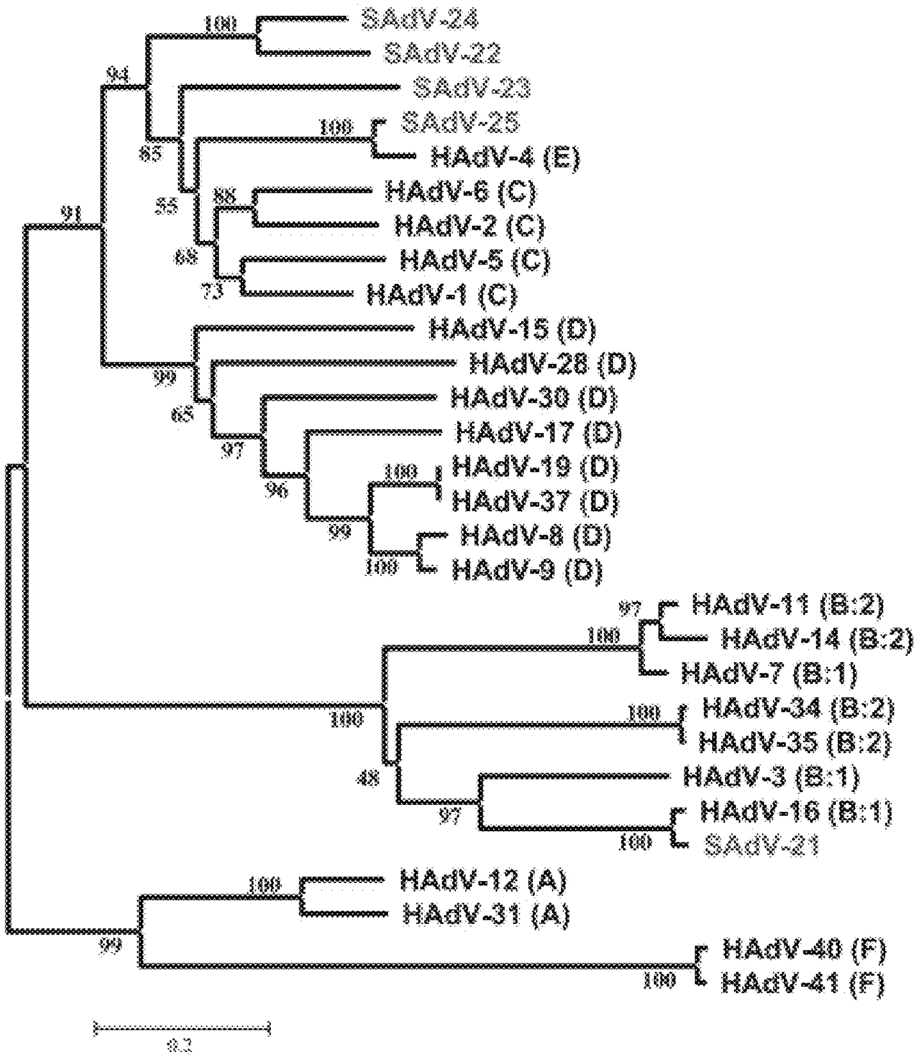
Figures 2, 5:
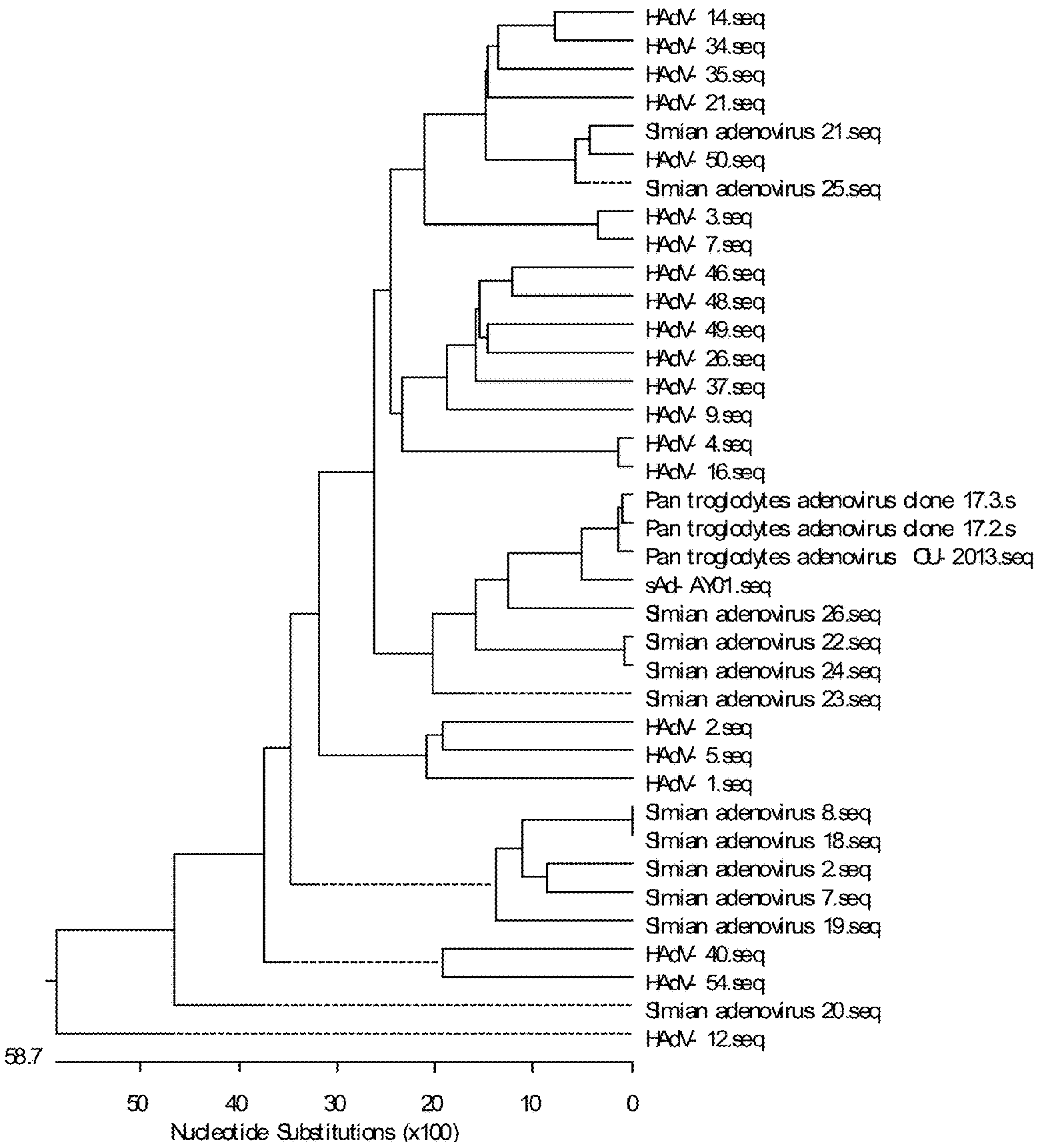

The invention is based on the comparison of the sequence of HVR1-6 of the hypervariable region of the hexon gene with the sequence of HVR1-6 of the known serotype in the database (reference: Rika M O, Yasushi S, Tsunetada K, et a 1. Quantitative Detection and Rapid Identification of Human Adenoviruses.J Clin Microbio1.2007. 4 5:9 5 8. 967). The comparison results are shown in FIG. 4, where 1~12 represent HVR1-6 sequences of 12 known serotypes, and 13 represents HVR1-6 sequence of orangutan adenovirus sAd-AY01. From FIG. 4, it can be seen that the homology between HVR1-6 sequence of orangutan adenovirus sAd-AY01 and some known serotypes HVR1-6 sequences is between 49.8% and 67.5%. Based on the sequence of HVR1-6 in the hypervariable region of its hexon gene, it is compared with the known chimpanzee adenovirus partial serotype HVR1-6 sequence, monkey adenovirus partial serotype HVR1-6 sequence and human adenovirus partial serotype HVR1-6 sequence in GenBank™, the homology is between 49% and 91%. The phylogenetic tree was constructed by DNAstar software (FIG. 5-2), and the homology and difference of sequences were analyzed by ClustalW calculation method. The adenovirus sequence with the largest homology was part of the gene of Pan troglodytes adenovirus clone 17.2 major capsid protein gene (GenBank™: MF176134.1), and the largest homology was 91.63%. Finally, it was determined that the chimpanzee adenovirus was a new adenovirus that had not been discovered. The sequence of HVR1-6 of the new chimpanzee adenovirus are as below:

```
Seq ID NO. 9: HVR1:
ATAACCAAAGACAATGGAACTGATAAG;

Seq ID NO. 10: HVR2:
GAGTCAGGGGGTGAAAGCAAGAAA

Seq ID NO. 11: HVR3:
CATGATACTATTGGAGCTGAAGACAAG

Seq ID NO. 12: HVR4:
AAGGACGATGGCACTACT

Seq ID NO. 13: HVR5:
AGTCAGCAAGCTAGT

Seq ID NO. 14: HVR6:
GGCACTGATGAAACAAGT
```

Example 3 Construction of a Novel Chimpanzee Adenovirus (psAd) Vector Containing Fluorescent Labels The chimpanzee adenovirus (sAd) genome is a linear DNA larger than 36 kb in length, which is difficult to edit effectively. Therefore, it is necessary to connect the replication-related elements in bacteria, such as replicon (pACYC) and resistance gene (kanamycin), to the chimpanzee genome to form a circular plasmid.

Therefore, it is necessary to construct a circular plasmid with a size of about 6000 bp from replicon (pACYC), resistance gene (kanamycin), left arm (~1400 bp) and right arm (~1400 bp) of chimpanzee genome, and then transform it into BJ5183 competence together with chimpanzee adenovirus genome after linearization, and carry out homologous recombination to form a circular plasmid of chimpanzee, which can make it replicate effectively in bacteria. At the same time, in order to monitor the transfection efficiency of plasmids in cells, green fluorescent expression frames (RSV promoter, EGFP, BGHpolyA) were added. After transfection into cells, the transfection efficiency of large vectors was judged by the amount of fluorescence in TP0 generation.

3.1 Construction of Adenovirus Genomic DNA Cyclic Shuttle Plasmid psAd-Shuttle

Primer design of chimpanzee adenovirus sAd-AY01 left arm, right arm and bacterial element

```
PACYC-F:
                                          (SEQ ID: 18)
tttgaggtatattattgatgatgttaattaTTGGTTCCACTTGAGCGTC

AGAC

BGHpoly A-R:
                                          (SEQ ID: 19)
tttgaggtatattattgatgatgttaattaaAGACGAAAGGGCCTCGTT

TGTA

Left arm-F:
                                          (SEQ ID: 20)
catcatcaataatatacctcaaac
```

-continued

```
Left arm-BamHI-R:
                                          (SEQ ID: 21)
CTTTGCTGGGAAGCCACCGTGGGAGGATCCAAGTAAACACACATGTGGC

A

Right arm-F:
                                          (SEQ ID: 22)
TCCACGGTGGCTTCCAGCAA

Right arm-R:
                                          (SEQ ID: 23)
catcatcaataatatacctcaaac
```

Figure 6:
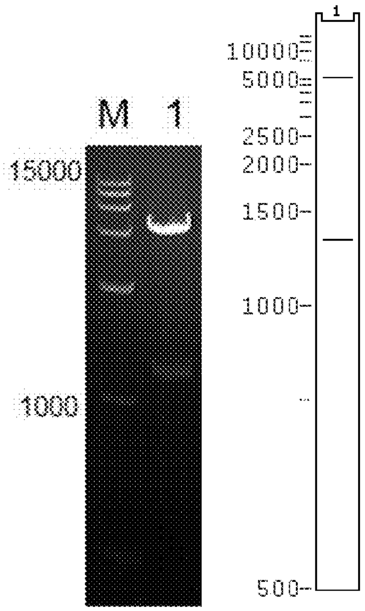
FIG. 6 is the electrophoresis results of enzyme digestion identification of the shuttle plasmid psAd-shuttle constructed in example 3, in which M: 15000 bp Marker; 1: psAd-shuttle BamhI& EcoRI digestion
Figure 7:
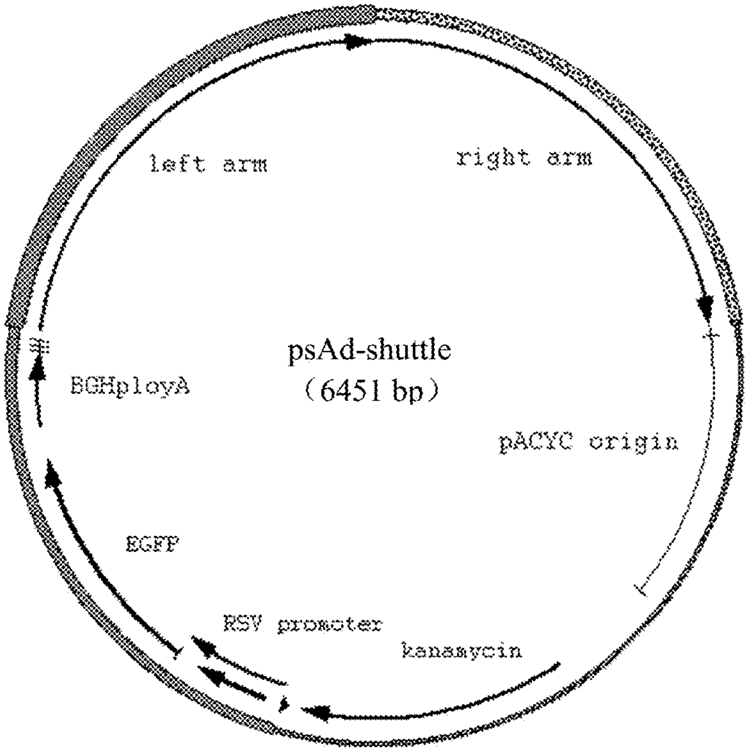
FIG. 7 is the plasmid map of the adenovirus genomic DNA cycling shuttle plasmid psAd-shuttle constructed in example 3.

Gene synthesis bacterial element, replicon (pACYC), resistance gene (kanamycin), green fluorescent expression frame (RSV promoter, EGFP, BGHpoly A);

3 fragments of left arm, right arm and bacterial element were amplified by PCR;

It was cloned seamlessly by using BM smealess cloning kit;

⑤ Kanamycin resistance was screened, and the correct colonies were selected for enzyme digestion identification. The results are shown in FIG. 6, in which M: 15000 bp Marker; 1: psAd-shuttle BamHI-EcoRI digestion. As can be seen from FIG. 6, the shuttle plasmid psAd-shuttle was successfully constructed, and the map of the constructed shuttle plasmid psAd-shuttle is shown in FIG. 7.

3.2 Chimpanzee adenovirus vector plasmid psAd was obtained by homologous recombination of shuttle plasmid psAd-shuttle and chimpanzee adenovirus genome ① BamHI linearized shuttle plasmid psAd-shuttle, and the enzyme digestion system was as follows:

Shuttle plasmid psAd-shuttle 3 μg; BamHI 2 μL; Buffer cutsmart 4 μL; Replenish water to 40 μl. The reaction condition is 37° C., 1 h; 65° C., 20 min;

② Dephosphorylation of Enzyme Digestion Products

Figure 8:
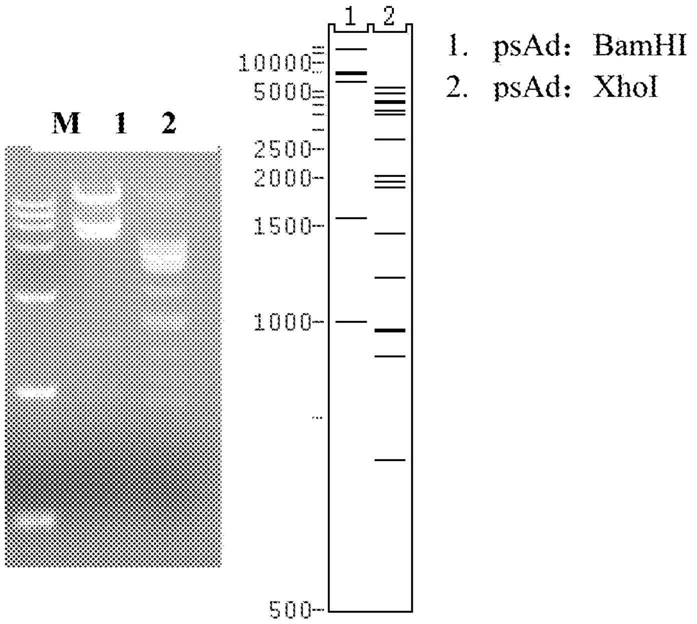
FIG. 8 is the electrophoresis result of enzyme digestion identification of the chimpanzee adenovirus vector plasmid psAd constructed in example 3, in which M: 15000 bp Marker; 1: psAd BamHI digestion; 2: psAd XhoI digestion.
Figure 9:
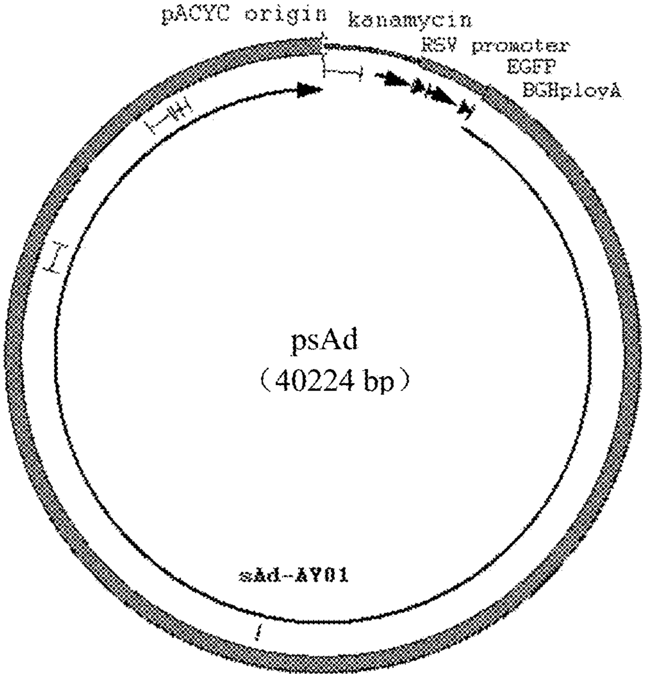
FIG. 9 is the plasmid map of the chimpanzee adenovirus vector plasmid psAd constructed in example 3.

Reaction system: Enzyme digestion reaction solution 40 μL; Dephosphorylase 1 μL; Dephosphorylated buffer 5 μL; Replenish water to 50 μL. The reaction condition is 37° C., 1 h; 65° C., 5 min inactivation;

Used OMEGA Ultra-Deep Gel Extraction Kit to recycle glue;

BJ5183 competent cells were co-transformed with 100 ng of purified shuttle plasmid and 100 ng of adenovirus genomic DNA. The transformed products were coated with LB plate containing Kan and cultured at 37° C. for 12~16 h;

The colonies were cultured in 5 mL LB liquid medium containing Kan for 12~16 h at 37° C., and the plasmid was extracted for enzyme digestion verification. The results are shown in FIG. 8, in which M: 15000 bp Marker; 1: psAd BamHI digestion; 2: psAd XhoI digestion; As can be seen from FIG. 8, a new chimpanzee adenovirus psAd plasmid containing fluorescent markers was successfully constructed, and the constructed plasmid map is shown in FIG. 9.

Example 4 Construction of a Novel Replication-Deficient Chimpanzee Adenovirus Vector psAd E1 E3

4.1 The E1 region of chimpanzee adenovirus vector psAd was excised by CRISPR/cas9 method to obtain the vector plasmid psAd E1 with E1 knockout, and the digestion site PsiI was introduced ① Selection of Target Sequence of Target Gene E1 CRISPR The target sequence of E1 gene knockout was determined by using Thermofisher.com/crisprdesign software.

```
E1A:
                                     (SEQ ID: 24)
TCATTCACCGCCTCCTCGT;

E1B:
                                     (SEQ ID: 25)
ggacctgcgacccgatcatt;
```

DNA Amplification of sAd-E1A-gRNA and sAd-E1B-gRNA

1) DNA Template Design of sAd-E1A-gRNA

```
                                     (SEQ ID: 26)
5'-TAATACGACTCACTATAGATTCACCGCCTCCTCGTTTTTAGAGCT

AAAATAGCAAGGCTAGTCCGTATCAACTTGAAAAGTTTT-3'
```

2) DNA Template Design of sAd-E1B-gRNA

```
5'-Designing upstream and downstream primers of
DNA template for amplification of sAd-E1A-gRNA
and sAd-E1B-gRNA

sAd-E1A-gRNA-Forward:
                                     (SEQ ID: 27)
TAATACGACTCACTATAG ATTCACCGCCTCCTC

sAd-E1A-gRNA-Reverse:
                                     (SEQ ID: 28)
TTCTAGCTCTAAAAC AACGAGGAGGCGGTGAAT

sAd-E1B-gRNA-Forward:
                                     (SEQ ID: 29)
TAATACGACTCACTATAGacctgcgacccgatc

sAd-E1B-gRNA-Reverse:
                                     (SEQ ID: 30)
TTCTAGCTCTAAAACaatgatcgggtcgcaggt
```

4. According to the instructions of Invitrogen™ GeneArt™ Precision gRNA Synthesis Kit, DNA templates for amplifying sAd-E1A-gRNA and sAd-E1B-gRNA are obtained, and sAd-E1A-gRNA and sAd-E1B-gRNA are obtained by in vitro transcription, and purified to obtain gRNA. The sequence after in vitro transcription is as follows:

```
sAd-E1A-gRNA:
                                     (SEQ ID: 31)
GAUUCACCGCCUCCUCGUUGUUUUUAGAAAUAGCAAGUUAAAAUAAGGC

UAGUCACAACUUGAAAAAAGUGUUU

sAd-E1B-gRNA:
                                     (SEQ ID: 32)
GaccUgcgacccgaUcaUUGUUUUUAGAAUAGCAAGUUAAAAUAAGGCU

AGUUUCAACUUGAAAAAAAGGUGUUU
```

⑤ CRISPR/Cas9 "Digestion" psAd

The vector plasmid psAd was obtained by digesting example 3 with sAd-E1A-gRNA, sAd-E1B-gRNA and cas9. The reaction system was Cas9 protein 3 μg, sAd-E1A-gRNA 3 ug, sAd-E1B-gRNA 3 ug, psAd vector plasmid 3 ug, NEB buffer 3.5 μL and supplemented water to 50 μL.

Figure 10:
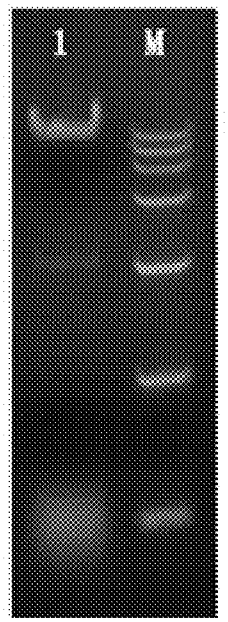
FIG. 10 is the agarose gel electrophoresis result of CRISPR/Cas9 "digested" psAd plasmid in example 4, where M: 15000 bp Marker; 1: psAd "digested" E1 with cas9.

The reaction was incubated overnight at 37° C. and detected by agarose gel electrophoresis. The results are shown in FIG. 10, where M: 15000 bp Marker; 1: psAd "digested" E1 with cas9. As can be seen in FIG. 10, the CRISPR/Cas9 "digested" psAd plasmid was successfully obtained and the vector was purified using the Axygen Gel Recovery Kit.

⑥ Amplify the HRPT Sequence Inserted into E1 Region, which Contains PsiI Cleavage Site Amplification Primers:

```
sAd-E1-HRPT-F:
                                     (SEQ ID: 33)
atgtgcccgagaacccccaaccttgcatttctcagtcctaaac

sAd-E1-HRPT-R:
                                     (SEQ ID: 34)
cccgttgcaggacaacaccaaatcactttgcatatagtatacatg
```

The amplified sequence is:

```
                                     (SEQ ID: 35)
cttgcatttctcagtcctaaacagggtaatgggctggggctgaatcaca

tgaaggcaaggtcagattttttattattatgcacatctagcttgaaaatt

ttccattaagtcaattacagtgaaaaacctcacctggtattgaatgctt

gccttgtatgtctggctattctgtgtttttattttaaaattataatatc

aaaatatttgtgttataaaatattctaactatggaggccataaacaaga

agactaaagttctctcctttcagccttctgtacacatttcttctcaagc

actggtttatgcatgtatactatatgcaaaagtg
```

Figure 11:
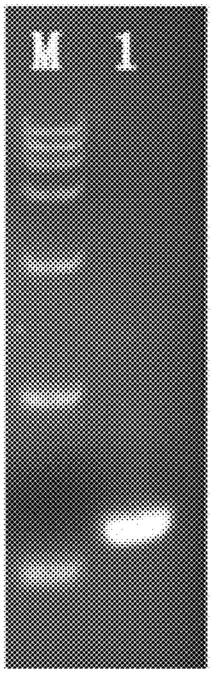
FIG. 11 is the agarose gel electrophoresis result of amplified fragment of HRPT sequence in example 4, wherein: M: 15000 bp Marker; 1: HRPT fragment.

PCR amplified fragment, as shown in FIG. 11, where: M: 15000 bp Marker; 1: HRPT fragment; The fragment was purified using Axygen gel recovery kit.

Figure 12:
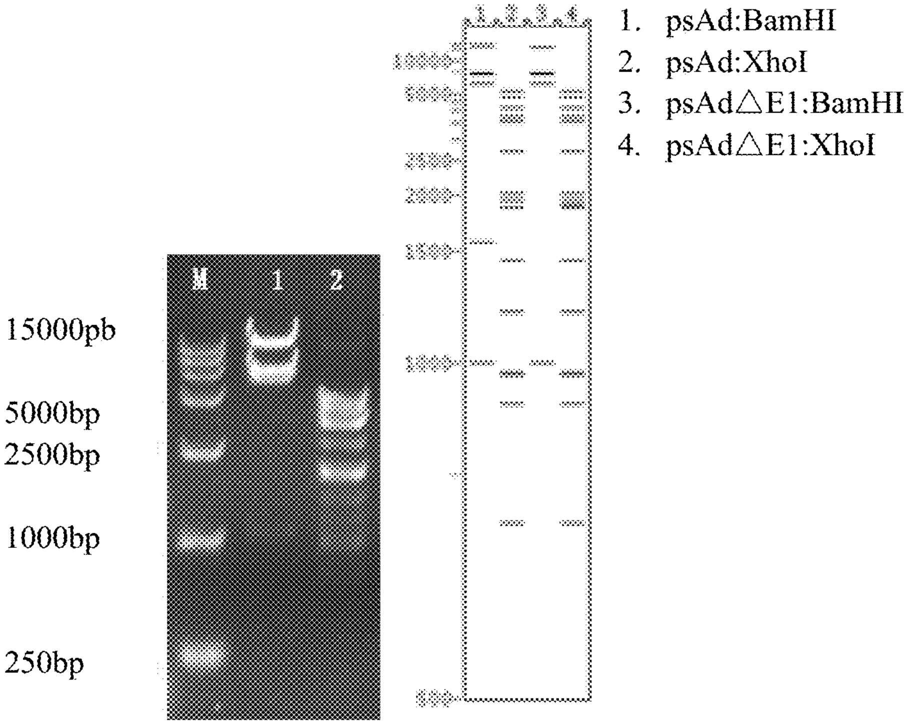
FIG. 12 is the result of identification electrophoresis after digestion of psAdΔE1 construct in example 4.

⑦ Using BM smealess cloning kit of Beijing Bomade Gene Technology Co., Ltd. to connect the vector with the fragment; The identification results after enzyme digestion are shown in FIG. 12, and the chimpanzee adenovirus vector psAd ΔE1 with E1 gene deletion was successfully obtained.

4.2 The vector plasmid psAd ΔE1ΔE3 was obtained by excising the E3 region of psAd ΔE1 adenovirus by CRISPR/cas9

① Selection of Target Sequence of Target Gene E3 CRISPR

The target sequence of E1 gene knockout was identified using the Thermofisher.com/crisprdesign software GeneArt™ CRISPR Search and Design tool (thermofisher-.com/crisprdesign)

```
sAdE3A:
                                     (SEQ ID: 36)
AGCGGCAGGGATACAAGTCC;

sAdE3B:
                                     (SEQ ID: 37)
GGGAAATCACCCTCAAGCT;
```

DNA Amplification of sAd-E3A-gRNA and sAd-E3B-gRNA

1) DNA Template Design of sAd-E3A-gRNA

```
                                     (SEQ ID: 38)
5'AATACGACTCACTATAGCGGCAGGGATACAAGTCCGTTTAGAGCT

AAAATAGCAAGGGTTT-3'
```

2) DNA Template Design of sAd-E3B-gRNA

```
                                        (SEQ ID: 39)
5'-TAATACGACTCACTATAGGAAATCACCCTCAAGCTGTTTTAGAGCT

AAAATAGCAAGTTAAAATAGGGCTAGTCCGTATCAACTTGAAAGGGGCA

CCGAGGGGGCACCGAGGGTGGTGTGTTTTTT-3'
```

Designing upstream and downstream primers of DNA template for amplification of sAd-E3A-gRNA and sAd-E3B-gRNA

```
sAd-E3A-gRNA-F:
                                   (SEQ ID: 40)
TAATACGACTCACTATAGCGGCAGGGATACAAG

sAd-E3A-gRNA-R:
                                   (SEQ ID: 41)
TTCTAGCTCTAAAACGGACTTGTATCCCTGCCG

sAd-E3B-gRNA-F:
                                   (SEQ ID: 42)
TAATACGACTCACTATAGGAAATCACCCTCAA

sAd-E3B-gRNA-R:
                                   (SEQ ID: 43)
TTCTAGCTCTAAAACAGCTTGAGGGTGATTTCC
```

4. According to the instructions of Invitrogen™ GeneArt™ Precision gRNA Synthesis Kit, DNA templates for amplifying sAd-E3A-gRNA and sAd-E3B-gRNA are obtained, and sAd-E3A-gRNA and sAd-E3B-gRNA are obtained by in vitro transcription, and purified to obtain gRNA. The sequence after in vitro transcription is as follows:

```
sAd-E3A-gRNA:
                                        (SEQ ID: 44)
GCGGCAGGGAUACAAGUCCGUUUUUAGAAUAGCAAGUUAAAAUAAGGCU

AGUCCGUUAUCAACUUGAAAAAAGAGUGUUU

sAd-E3B-gRNA:
                                        (SEQ ID: 45)
GGGAAAUCACACCCUCAAGCUGUUUUAGAAAUAGCAAGUUAAAAAGGUU

AUCACAACUUGAAAAAGUGUUU
```

⑤ CRISPR/Cas9 "Digests" E3 of psAdΔE1

The psAdΔE1 plasmid was digested with sAd-E3A-gRNA, sAd-E3B-gRNA and cas9. The reaction system was Cas9 protein 3 ug, sAd-E3A-gRNA 3 ug, sAd-E3B-gRNA 3 ug, psAdΔE1 vector plasmid 3 ug, NEB buffer 3.15 μL, and water supplementation to 50 μL.

Figure 13:
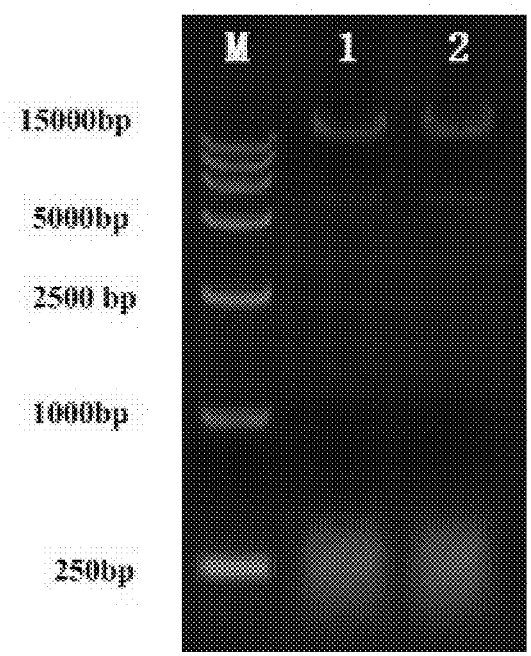
FIG. 13 is the agarose gel electrophoresis result of CRISPR/Cas9 "digestion" psAdΔE1 plasmid in example 4, where M: 15000 bp Marker; 1, 2: psAdΔE1 "digested" E3 with cas9.

Enzyme digestion reaction was incubated at 37° C. overnight. The carrier was purified using Axygen Gel Recovery Kit. The results of enzyme digestion are shown in FIG. 13: M: 15000 bp Marker; 1, 2: psAd E1 "digested" the product using cas9.

The excised pVIII and U-exon regions were amplified by PCR, and the glue was recovered;

The amplification primers are:

```
E3A-F:
                                        (SEQ ID: 46)
AGGAGCGGCAGGGATACAAG

E3A-R:
                                        (SEQ ID: 47)
TCAATCGTAGCCGTCCACCG
```

-continued

```
E3B-F:
                                        (SEQ ID: 48)
AGTCGGTGGACGGCTACGATTGATCACCCCCTTATCCCAGTGAAAT

E3B-R:
                                        (SEQ ID: 49)
CGAGGTCCACCCCCTCC
```

Figure 14:
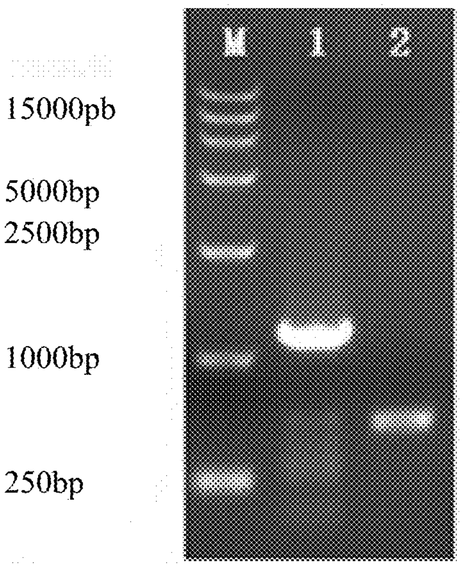
FIG. 14 is the gel electrophoresis results of pVIII and U-exon fragments in example 4, where M: 15000 bp Marker; 1: Partial fragment of PVIII; 2: U-exon partial fragment.

The amplified fragments are:

E3A-F and E3A-R were used as a pair of primers to amplify partial fragments of pVIII; E3B-F and E3B-R were used as a pair of primers to amplify partial fragments of U-exon. As shown in FIG. 14, where M: 15000 bp Marker; 1: Partial fragment of PVIII; 2: U-exon partial fragment.

Figure 15:
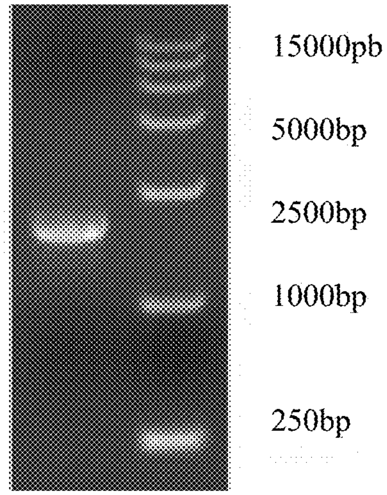
FIG. 15 is the gel electrophoresis result of pVIII-U-exon fragment amplified by fusion PCR in example 4.

The pVIII-U-exon fragment was amplified by E3A-F and E3B-R fusion PCR, and the glue was recovered; As shown in FIG. 15, the final fragment is a 1775 bp fusion fragment.

Figure 16:
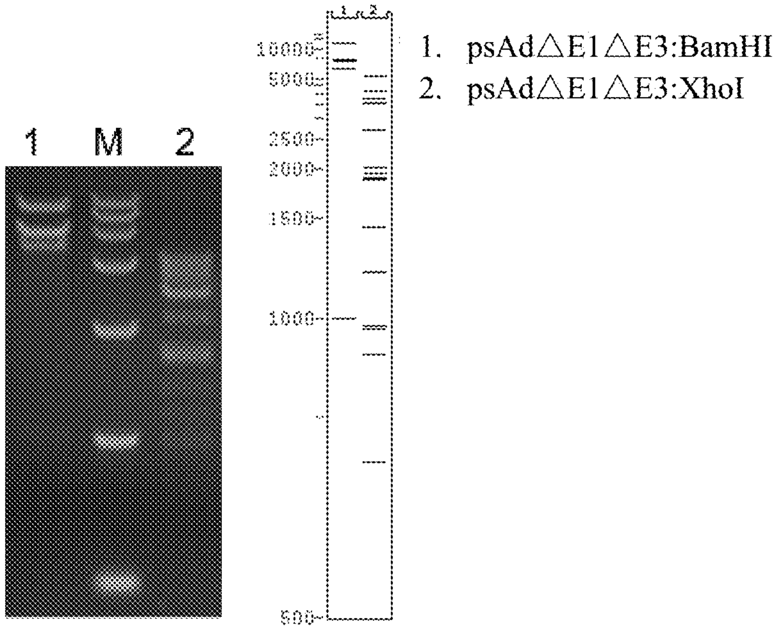
FIG. 16 is the results of enzyme digestion identification electrophoresis of psAdΔE1ΔE3 constructed in example 4, where M: 15000 bp Marker; 1: psAdΔE1ΔE3 BamHI digestion; 2: psAdΔE1 ΔE3 XhoI digestion; The right picture shows the enzyme digestion simulation of psAdΔE1ΔE3 plasmid.
Figure 17:
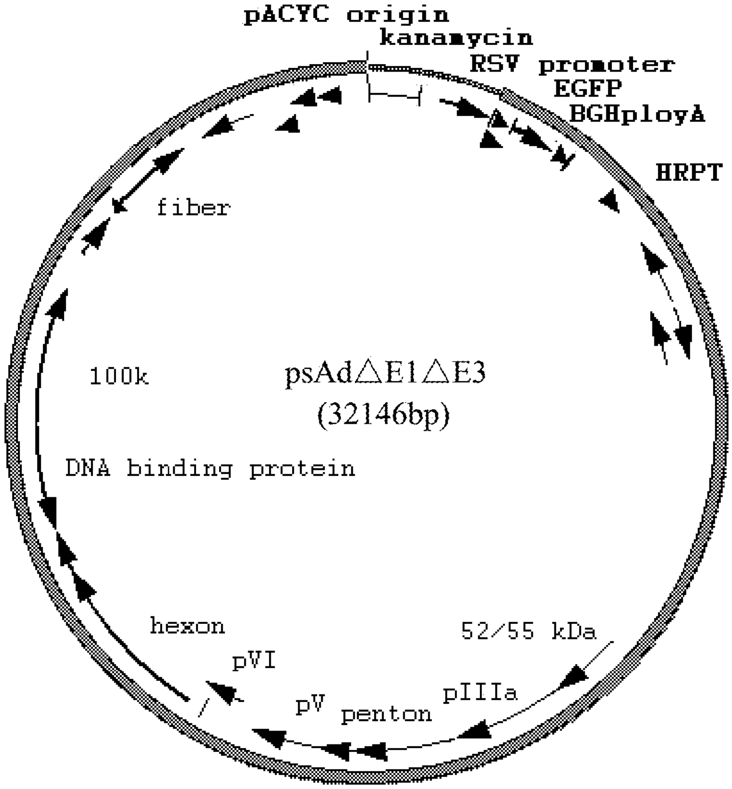
FIG. 17 is the plasmid map of psAdΔE1ΔE3 constructed in Example 4.

8 Using BM smealess cloning kit of Beijing Bomade Gene Technology Co., Ltd. to seamlessly clone the vector after cas9 "enzyme digestion" in step 5 and the pVIII-U-exon fusion fragment in step 7; Transforming to DH5 a competence, screening kanamycin resistance, culturing overnight at 37° C., picking colonies, extracting plasmids, and digesting with BamHI and XhoI; As shown in FIG. 16: M: 15000 bp Marker; 1: psAd E1 E3 BamHI digestion; 2: psAd E1 E3 XhoI digestion; The picture on the right shows the enzyme digestion simulation of psAd E1 E3 plasmid. The results were correct, and the plasmid psAd E1 E3 was successfully constructed. The plasmid map is shown in FIG. 17.

Example 5 Construction of a New Chimpanzee Adenovirus Vector psAdΔE1ΔE3 Shuttle Plasmid pSsAdE1 and a Shuttle Plasmid pSsAdE1-S Expressing Novel Coronavirus S Gene The new chimpanzee adenovirus vector is 35 kb long and has many restriction sites, so it is difficult to operate directly on the vector. It is necessary to construct its special shuttle plasmid and integrate the foreign genes to be expressed into the adenovirus vector by homologous recombination.

S protein is the main antigen protein of Novel Coronavirus, which will cause the main immune response in the process of infection. Therefore, COVID-19 vaccine, a new chimpanzee vector, chose S gene of COVID-19 as the expressed foreign gene. Therefore, it is designed to use CMV promoter to drive expression in E1 region, which can produce a large number of antigens and cause strong immune response.

5.1 Construction of a New Shuttle Plasmid pSsAdE1 for Chimpanzee Adenovirus Vector E1 Region To construct the shuttle plasmid of chimpanzee adenovirus vector, plasmid-related elements (replicon puc origin, resistance gene, eukaryotic system exogenous gene expression frame CMV-MCS-SV40 polyA) and the left arm and right arm of E1 region were connected in a suitable sequence.

① PCR amplified the left arm and right arm of chimpanzee E1 region to replicate related elements, resistance genes and CMV-MCS-SV40 poly A. The template of left arm and right arm was chimpanzee adenovirus vector, and the template of replicating related elements and resistance genes and CMV-MCS-SV40 polyA was obtained by synthesis.

The primer design is as follows

```
Left-arm-F:
                                          (SEQ ID: 50)
TGGATCGGTGATCACCGATCCCGTTTCAAAGTGTAGATCTGACTC

Left-arm-R:
                                          (SEQ ID: 51)
GTTAGCTCACTCATTAGGCACCCttaattaacatcatcaataatatacc

Puc-F:
                                          (SEQ ID: 52)
GGGTGCCTAATGAGTGAGCTA

Amp-R:
                                          (SEQ ID: 53)
GACGTCAGGTGGCACTTTTC

Right-arm-F:
                                          (SEQ ID: 54)
CCCGAAAAGTGCCACCTGACGTCTCCGACCAGCCGGATGAGC

Right-arm-R:
                                          (SEQ ID: 55)
CCCCGTAATTGATTACTATTAATAGAGTGAGTAGTGTTGGGG

CMV-F:
                                          (SEQ ID: 56)
TTAATAGTAATCAATTACGGGGT

SV40-R:
                                          (SEQ ID: 57)
CGGGATCGGTGATCACCGAT
```

PCR amplification system: left-arm-F and left-arm-R were used as a pair of primers to amplify the left arm of the shuttle plasmid, puc-F and Amp-R were used as a pair of primers to amplify the replicon and resistance genes needed by the plasmid, right-arm-F and right-arm-R were used as a pair of primers to amplify the right arm of the shuttle plasmid, and CMV-F and SV40-R were used as a pair of primers to amplify the foreign gene expression frame CMV-MCS-SV40 poly A (Seq ID NO. 16).

Figure 18:
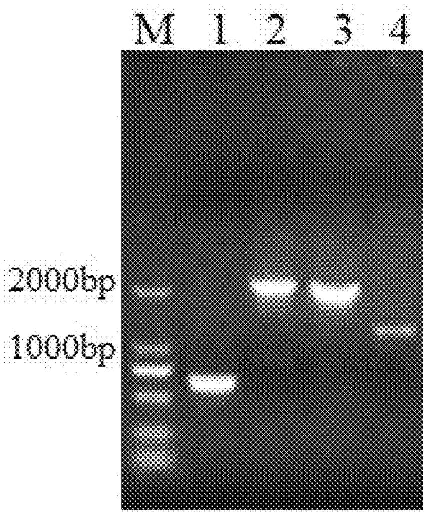
FIG. 18 is the gel electrophoresis results of PCR amplified left arm, puc & amp, right arm, CMV-MCS-SV40 sequences in example 5, wherein: M: 2000 bp Marker; 1 is the fragment left arm; 2 is the fragment puc& 3 is the fragment right arm; 4 is fragment CMV-MCS-SV40.

The amplification results are shown in FIG. 18: M: 2000 bp Marker; 1 is the fragment left arm; 2 is the fragment puc& 3 is the fragment right arm; 4 is fragment CMV-MCS-SV40.

The above four fragments were purified by Axygen gel recovery kit;

3. Using BM smealess cloning kit of Beijing Bomade Gene Technology Co., Ltd. to connect the four fragments; Junction system: left arm, puc & amp, right arm, CMV-MCS-SV40 fragment 2 ul; 2×measure 10 ul; Replenish water to 20 ul. Reaction conditions: 50° C., 40 min. Transformed DH5 a competent cells were coated on LB solid medium (ampicillin-resistant) and cultured overnight at 37° C.

Figure 19:
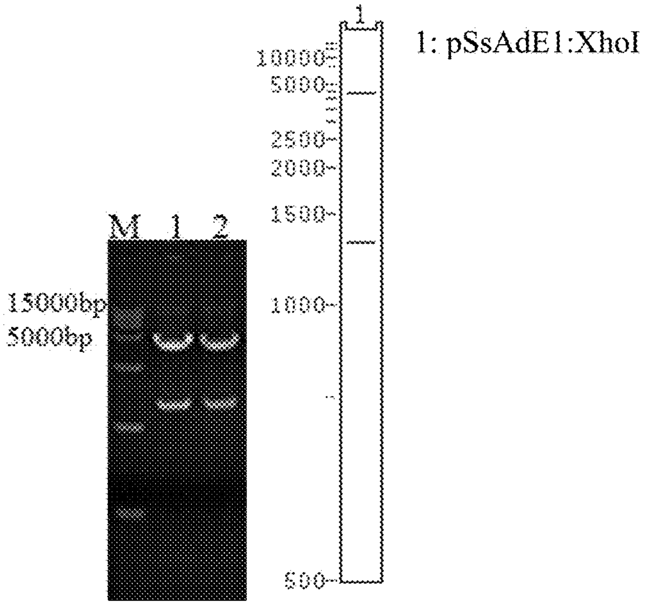
FIG. 19 is the results of enzyme digestion identification electrophoresis of the shuttle plasmid pSsAdE1 constructed in example 5.

After screening, the extracted plasmid was digested and identified; Results As shown in FIG. 19, the shuttle plasmid pSsAdE1 was successfully obtained.

5.2 Adding WPRE Element to Shuttle Plasmid to Obtain pSsAdE1-WPRE Element

WPRE can keep the mRNA stable and increase the viral yield

① PCR Amplification of WPRE Element

Primer Design

```
WPRE-NotI-F:
                                          (SEQ ID: 58)
ATATCCAGCACAGTGGCGGCCGGGCCGCTCGACAATCAACCTCTGGATT

A

WPRE-NotI-R:
                                          (SEQ ID: 59)
TAAACGGGCCCTCTAGACTCGAGGCGGCCGCCGGGGGGGGGGGGGGGG

GGGGGGGGGGGGGGGCGCCA
```

PCR Amplification of WPRE Fragment

③ NotI enzyme digestion of shuttle plasmid pSsAdE1, and enzyme digestion reaction system: vector pSsAdE1, NotI 1 ul; 10×cutsmart buffer 5 ul; Replenish water to 50 ul.

The WPRE and the digested pSsAdE1 gum were recovered and purified;

It was cloned seamlessly with BM Smealess cloning kit;

Reaction system: pSsAdE1-UCOE0.65, WPRE fragment 2 ul; 2×BM smealess10 ul; Replenish water to 20 ul. Reaction conditions: 50° C., 40 min.

Figure 20:
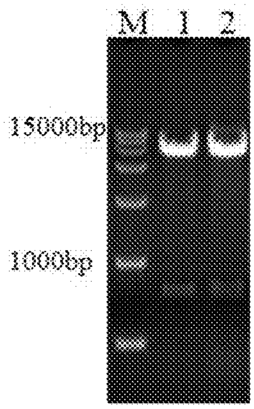
FIG. 20 is the enzyme digestion identification electrophoresis results of the pSsAdE1-WPRE element constructed in example 5, where M: 15000 bp Marker; 1, 2 were identified by pSsAdE1-WPRE NotI enzyme digestion; The pSsAdE1-WPRE component was successfully built.

⑥ Transformed DH5 a competent cells, coated on LB solid medium (ampicillin resistance), cultured overnight at 37° C., screened, extracted plasmid digested and identified; As shown in FIG. 20: M: 15000 bp Marker; 1, 2 were identified by pSsAdE1-WPRE NotI enzyme digestion; The pSsAdE1-WPRE component was successfully built.

5.3 Construction of Shuttle Plasmid pSsAdE1-WPRE-S Expressing Complete S Protein Gene of COVID-19 in Novel Coronavirus ① The COVID-19 S protein gene was amplified by PCR, and the primers were designed as follows:

```
S-EcoRV-F:
                                          (SEQ ID: 60)
TCCCTGATCACTGCAGAATTCGATATCgccaccATGTTCGTTTTCTGGT

GCTG

S-WPRE-HindIII-R:
                                          (SEQ ID: 61)
ATTGTCGAGCGGCCGCAATCGATAAGCTTtcaGGTGTAGTGCAGCTTCA

C
```

② pSsAdE1-WPRE was digested by EcoRV and HindIII, and the enzyme digestion reaction system was pSsAdE1-WPRE, EcoRV and HindIII 1 ul; 10×cut smart buffer 5 ul; Replenish water to 50 ul.

Collecting and purifying S and pSsAdE1 gum after enzyme digestion;

It was cloned seamlessly by using BM Smealess cloning kit;

Reaction system: pSsAdE1-WPRE, S fragment 2 ul; 2×BM smealess 10 ul; Replenish water to 20 ul. Reaction conditions: 50° C., 40 min.

Figure 21:
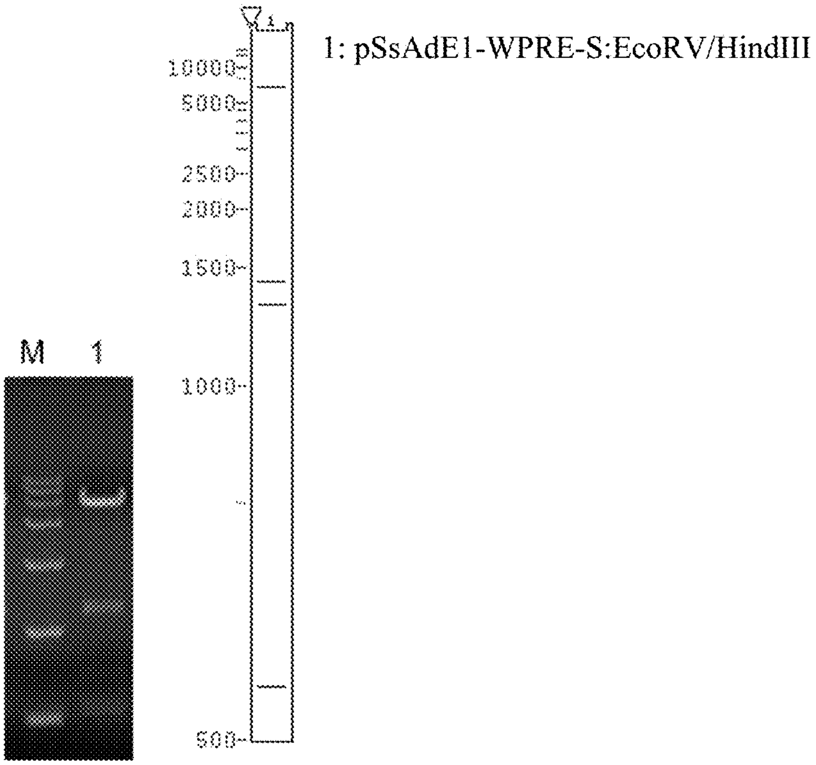
FIG. 21 is the electrophoresis result of enzyme digestion identification of shuttle plasmid pSsAdE1-WPRE-S constructed in example 5, in which M: 2000 bp Marker; 1 and 2 are pSsAdE1-WPRE-S EcoRV & HindIII.

⑤ Transformed DH5 a competent cells, coated on LB solid medium (ampicillin resistance), cultured overnight at 37° C., screened, extracted plasmid digested and identified; As shown in FIG. 21: M: 2000 bp Marker; 1, 2 were identified by pSsAdE1-WPRE-S EcoRV & HindIII enzyme digestion; The results were correct, and the shuttle plasmid pSsAdE1-WPRE-S was successfully constructed.

Example 6 Homologous Recombination to Obtain a New Recombinant Chimpanzee Adenovirus Vector psAd-S 6.1 Homologous recombination of shuttle plasmid pSsAdE1-WPRE-S and adenovirus vector plasmid psAd ΔE1ΔE3

1) PacI and PsiI digested the shuttle plasmid pSsAdE1-WPRE-S and the adenovirus vector plasmid psAd ΔE1ΔE3. The enzyme digestion system was as follows: A, shuttle plasmid pSsAdE1-WPRE-S 3 μg; PacI 2 μL; Buffer cutsmart 4 μL; Replenish water to 40 μl.

B, adenovirus vector plasmid psAdΔE1ΔE3 3 ug; PsiI 2μ; Buffer cutsmart 4 μL; Replenish water to 40 μl.

The reaction condition is 37° C., 1 h; 65° C., 20 min inactivation.

2) Dephosphorylation of Digested Products

Reaction system: Enzyme digestion solution 37.5 μL; Dephosphorylase 1 μL;

Dephosphorylated buffer 5 μL; Replenish water to 50 μL. The reaction condition is 37° C., 1 h; 65° C., 5 min inactivation.

3) Vectors and fragments were recovered using the OMEGA Ultra-Deep Gel Extraction Kit.

4) Competent BJ5183 cells were co-transformed with 100 ng of purified shuttle plasmid and 100 ng of purified adenovirus vector. The transformed products were coated with LB plate containing Kan and cultured at 37° C. for 12~16 h.

5) The colonies were cultured in 5 mL LB liquid medium containing Kan at 37° C. for 12~16 h, and the plasmids were extracted for XhoI digestion.

Figure 22:
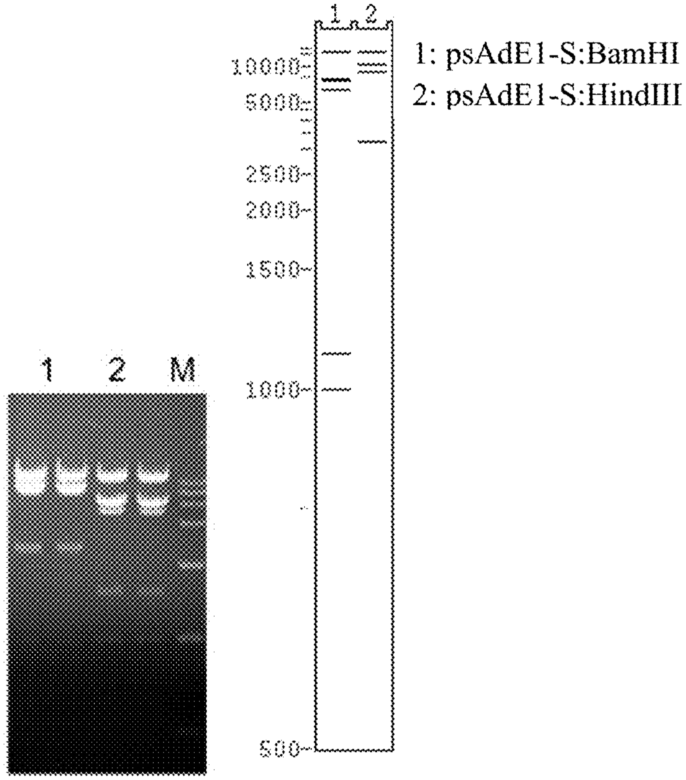
FIG. 22 is the results of enzyme digestion identification electrophoresis of the recombinant novel chimpanzee adenovirus vector psAd-S constructed in example 6, in which M: 15000 bp Marker; 1: psAd-S HindIII digestion; 2: psAd-S BamHI.

6) Transforming the positive plasmid into DH5a competence, picking a colony in 5 mL LB liquid medium containing kanamycin, shaking culture at 37° C. for 12~16 h, and extracting the plasmid for HindIII and BamHI digestion verification again. As shown in FIG. 22: M: 15000 bp Marker; 1: psAd-S HindIII digestion identification; 2: psAd-S BamHI digestion identification; successfully constructing a new recombinant chimpanzee adenovirus vector psAd-S.

Example 7 Packaging of the Novel Recombinant Chimpanzee Adenovirus psAd-S

The psAd-S vector plasmid was packaged using 293 cells (purchased from ATCC, lot number 70009859) as follows:

① Preparation of 293 cells: The day before transfection, the cells to be transfected were prepared and inoculated into a 6-well plate, $0.5\times10^6$/well, and cultured at 37° C. and 5% $CO_2$ for 24 hours. On the day of transfection, the confluence rate of cells was 40-50%.

② Linearization of plasmid psAd-S: The plasmid to be transfected was digested with I-sceI enzyme, incubated at 37° C. for 40 min, and then inactivated at 65° C. for 20 min.

Transfection: The linearized 2 μg plasmid and PEI were diluted with 100 μL serum-free medium respectively; Plasmid diluent was added to PEI diluent, and then absorbed repeatedly for 5 times or swirled for 10 seconds, and then incubated at room temperature for 10 minutes to form transfection complex. During incubation, the cell culture medium was gently sucked from the culture plate, and 2 mL of fresh growth medium was added. After 10 minutes, the transfection complex was added to the cells changed from fresh medium.

Cell culture: 293 cells after transfection were cultured in 37° C., 5% $CO_2$ incubator for 72-96 hours; After 72-96 hours of viral plasmid transfection, 6-well plate cell suspension was collected and placed in 15 ml centrifuge tube, i.e. TP0.

⑤ Continuous inoculation: freeze-thaw the collected cell suspension at −80° C. for 3 times, centrifuge at 4° C. and 2000 g for 10 minutes, infect 293 cells with 500 μL supernatant (293 cells need to be prepared one day in advance), incubate at 37° C. and 5% $CO_2$ for 60 minutes, supplement 2 mL FBS culture medium, culture at 37° C. and 5% $CO_2$ for 72 hours, and collect cell suspension, namely TP1; Repeat the previous steps to collect cell suspension, namely TP2. Continue to inoculate until the cells appear pathological changes.

Figure 23:
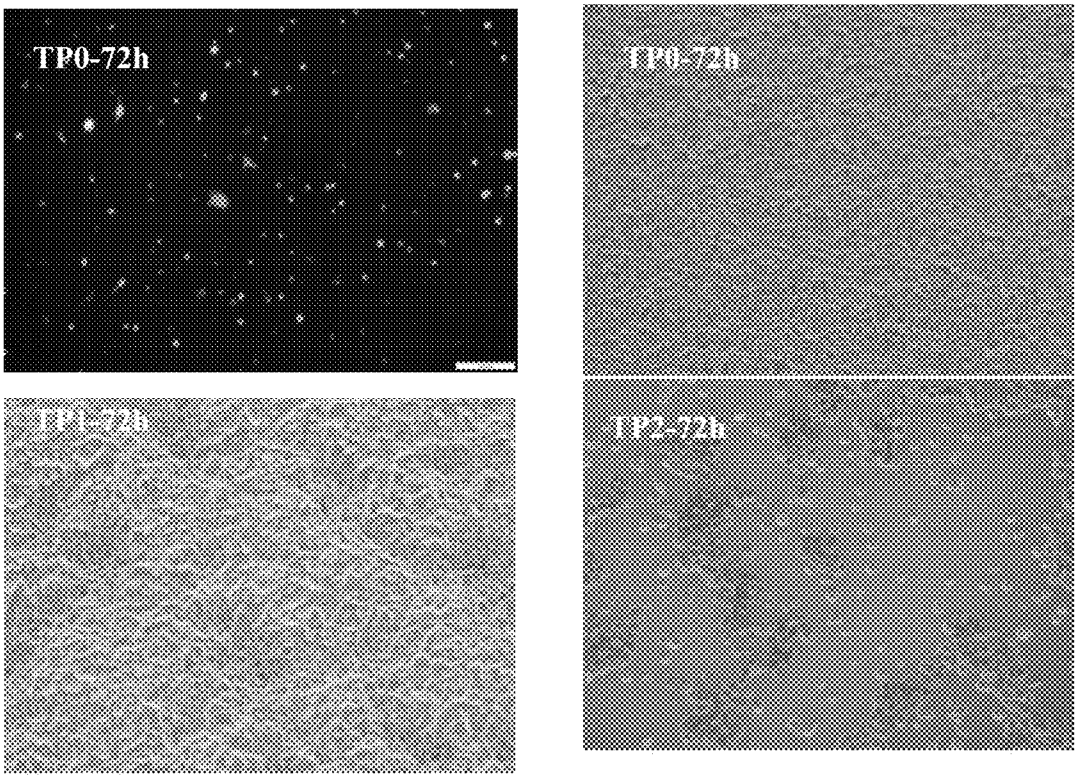
FIG. 23 is the e microscope photograph of cytopathic changes caused by TP0 to TP2 in example 7.

⑥ Cytopathic changes: When 293 cells were cultured from TP0 to TP2, the cells gradually became pathological changes until 293 cells became completely pathological changes. The cytopathic changes caused by TP0 to TP2 are shown in FIG. 23, respectively, and TP2 has completely changed.

Example 8 Titer Detection of Recombinant New Chimpanzee Adenovirus psAd-S Vaccine 8.1 HVR antigen protein of hypervariable region of hexon protein of new chimpanzee adenovirus (hexon)

Figure 24:
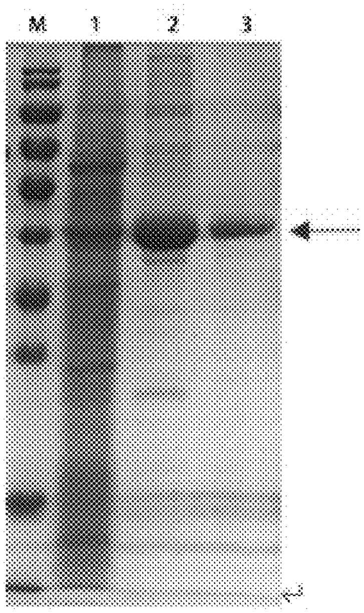
FIG. 24 is the e results of purification of the sAd-HVR protein obtained by NI column in example 8, where M: protein Maker; 1. supernatant of sAd-HVR bacteria liquid; 2: purified sAd-HVR protein; 3. Purified sAd-HVR protein diluent.

① Construct prokaryotic expression pET28b-sAd-HVR, and pET28b plasmid was donated by Beijing Bomade Gene Technology Co., Ltd.;

Transformation of PET-28a-sAd-HVR plasmid into BL21 (DE3) strain;

③ Overnight expression of IPTG at 24° C.;

Harvesting the bacteria liquid, centrifuging, and ultrasonic crushing the bacteria precipitate with PBS re-suspension; Ultra-speed centrifugation to obtain supernatant;

⑤ purifying the supernatant by NI column to obtain sAd-HVR protein, and the result is shown in FIG. 24, in which M: protein Marker; 1. supernatant of sAd-HVR bacteria liquid; 2: purified sAd-HVR protein; 3. purified sAd-HVR protein diluent;

8.2 Preparation of HVR antibody against hexon protein (hexon) hypermutation region of chimpanzee adenovirus Dissolve HVR protein in normal saline;

2. Mix with equal volume Freund's complete adjuvant by double push method (antigen concentration is about 0.1 mg/ml);

BALB/C mice were immunized by subcutaneous multipoint injection with 0.2 ml;

④ After 3 weeks, the same amount of antigen and incomplete Freund's adjuvant were mixed evenly and immunized;

⑤ After 4 weeks, the above methods were used to strengthen immunization once a week (incomplete Freund's adjuvant) for 3 times in total;

⑥ Three days after the last immunization, the serum titer was measured by cutting off the tail. If the expected purpose was achieved, the antiserum could be collected by bloodletting.

⑦ After indirect ELISA detection, the concentration of HVR antibody reached 1:200,000, which met the conditions and was finally released;

8.3 Detection of Titer with HVR Antibody of New Chimpanzee Adenovirus 293 cells were prepared. The cells grew well in T75 culture flask, discarded the supernatant, washed with PBS, digested with 0.25% trypsin, then added 10 ml DMEM fresh medium containing 10% fetal bovine serum to stop digestion, then blew and mixed evenly, inoculated into 6-well plate ($5\times10^5$/ml, 2 ml per well), and stood in a 5% $CO_2$ and $CO_2$ incubator at 37° C. After 24 hours, when the cells grew into monolayer cells, the culture medium was discarded, and the recombinant adenovirus was continuously diluted by 10-2~10-6 times with serum-free DMEM maintenance solution. Each dilution was inoculated into 2 wells with 250 μL per well. After 1 hour of infection, the supernatant was discarded, and the complete culture medium was supplemented, and then the culture was static in a 5% $CO_2$ and $CO_2$ incubator at 37° C. After 24 hours, the supernatant was discarded and the cells were washed with PBS, 1 mL per well. After discarding PBS, the cells were fixed with 1 mL cold formaldehyde at room temperature for 10 min. After discarding formaldehyde, the cells were washed with PBS, 1 mL per well, and then incubated with chimpanzee adenovirus HVR antibody, 1 ml per well. After 1 h at room temperature, the cells were washed with PBS again, 1 mL per well, and the sheep anti-rabbit-FITC second antibody was incubated. After 1 h at room temperature, the supernatant was discarded and the cells were washed with PBS again, and counted under fluorescence microscope (200 times, 10 continuous visual fields). Calculation: Virus titer (FFU/mL)=average×1013×4×10 (−n). The FFU of psAd-S virus is 5×108 FFU/ml.

8.4 Comparison of Titers of Different Adenovirus Vectors

The adenovirus stored by our company and HAd26, HAd5 and HAd28 produced in the market are used to detect the virus titer. The results are shown in Table 1. sAd-AY01 is a new chimpanzee adenovirus provided by the invention, and its titer is the highest, which can reach 5×108 FFU/ml, providing the most basic guarantee for the industrial production of chimpanzee adenovirus vaccine.

TABLE 1

Comparison of titers of adenovirus vectors

| Virus type | SAd-AY01 | HAd5 | HAd26 | HAd28 | Simian Adenovirus 40.1 |
|---|---|---|---|---|---|
| Titer FFU/mL | $5 \times 10^8$ | $1 \times 10^8$ | $5 \times 10^7$ | $4 \times 10^7$ | $1 \times 10^8$ |

Example 9 Detection of Stability of Recombinant New Chimpanzee Adenovirus psAd-S Vaccine The 293 cells were prepared. The cells grew well in T75 culture flask, discarded the supernatant, washed with PBS, digested with 0.25% trypsin, then added 10 ml of DMEM fresh medium containing 10% fetal bovine serum to stop digestion. Then, the 293 cells were planted in a 6-well plate ($5\times10^5$ cells/ml, 2 ml/well), incubated at room temperature for 1 hour to make them adhere to the wall. After incubation, the adherence degree was examined under microscope. The infection was carried out with psAd-S virus particles, and the titer of infection was 2 MOI/well. After the 293 cells became pathological changes 48 hours later, the cells were collected, frozen and thawed repeatedly for 3 times, then centrifuged at 2000 g, and the supernatant was collected. FFU was detected in the collected supernatant, and then the new 293 cells were re-infected until 30 generations. The virus fluids collected from the 5th, 10th, 15th, 20th, 25th and 30th generations were detected, and it was found that the virus genome was still intact, which indicated that replication-defective psAd-S virus could be stably packaged in 293 cells.

Example 10 Detection of psAd-S Recovery Mutation (RCA) in Recombinant Novel Chimpanzee Adenovirus The psAd-S virus RCA detection method is as follows:

1. Prepare psAd-S virus solution, measure its virus titer and determine the concentration of virus particles. The virus solution was mixed with 1% Universal Nuclease (virus solution with the concentration of 7.5-15 units/mL) to digest the DNA of the host cells, and the water bath was kept at 37 C for 40 min. The virus particles were collected using a 300 Kd ultrafiltration centrifuge tube after centrifugation at 1000 g for 30 min, followed by elution with 1×PBS. A260 was measured as the particle concentration=A260×1.1×$10^{12}$ VP/mL.

2. For virus infection, six-well plates of A549 cells were prepared, with each well cell being $2.5\times10^5$/well. The medium was discarded and washed with PBS once. Adenovirus was inoculated with virus at $1\times10^9$ vp/well to infect A549 cells. Wild-type sAd-AY01 adenovirus was used as the control at 37° C. and 5% $CO_2$. After 1 h, the virus solution was discarded and made up of 5% complete medium. The cells were cultured at 37° cand 5% $CO_2$ for 48 h.

3. Immunostaining was performed, and the cell supernatant was discarded. The cells were surface washing cells in PBS, fixed with ice formaldehyde, placed at −20° C. for 20 min, and washed with 1×PBS for three times, each time for 5 min. Then 2 ml 1% BSA-PBS solution was added into each well, placed in a shaker, and incubated for 1 h. After the supernatant was discarded, adenovirus type 5 fluorescent antibody (1:500 dilution) was added and incubated for 1 h, followed by washing with 1×PBS for three times, 5 min each time.

RCA was calculated using the equation as observed under a 10-fold fluorescence microscope $$RCA = (\text{average positive cell field}) \times (374\ \text{field/well}) \times (\text{dilution factor}))/\ \text{Total}\ VPs\ \text{in 0.5 ml viral sample}$$

The judging standard was that the level of RCA was less than 1RCA/3×$10^{10}$ vp. After statistics, the RCA level of psAd-S is less than 1RCA/3×$10^{10}$ vp, which indicates that the replication-defective psAd-S virus prepared by the invention can be stably packaged in 293 cells and cannot be converted into wild type or has low probability of being converted into wild type.

Figure 25:
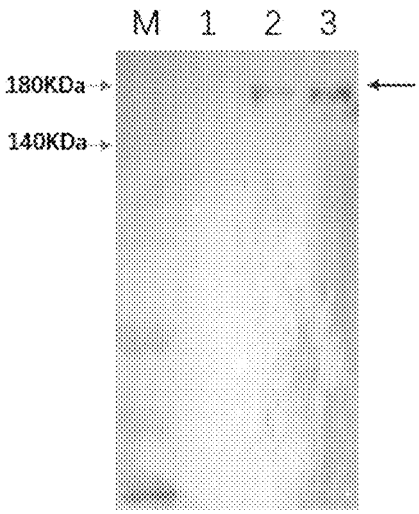
FIG. 25 is the Western Blot detection result of expression of psAd-S protein of recombinant novel chimpanzee adenovirus in example 11, wherein: M: 180 kda maker; 1, 293 blank cell control; 2, 3: Samples of 293 cells infected with psAd-S virus.

Example 11 Detection of Expression of Recombinant Novel Chimpanzee Adenovirus psAd-S Protein The 293 cells were prepared one day in advance and placed in a 12-well cell culture plate. The 293 cells were infected with psAd-S virus and the cells became diseased 48 hours later. All 1 ml of cells were collected and washed with PBS for sample preparation for Western Blot test. Spike's RBD protein antibody was used as the secondary antibody to detect the target protein. The RBD protein antibody was purchased from Beijing Yiqiao Shenzhou Technology Co., Ltd. The results of Western Blot test are shown in FIG. 25: M: 180 kDa marker. 1, 293 blank cell control; 2, 3: a sample of 293 cells infected with pSAd-S virus; The results showed that the S protein expressed by the chimpanzee adenovirus vector could be efficiently expressed in 293 cells.

Example 12 Chimpanzee Adenovirus Pre-Stored Immune Detection

Neutralizing antibody against AdHu5 is common in the population, and about one-third of the population has been immunized against AdHu5 in adulthood, while the population does not have the antibody against the novel chimpanzee adenovirus. Therefore, injection of the novel chimpanzee adenovirus vector vaccine into human body will not be neutralized by pre-existing immunity, and sufficient antibody can be produced. The result can be verified by neutralize antibody experiments. The experimental design was shown in Table 1, and the experimental steps were as follows:

(1) One day before, 96-well plates were paved for the preparation of A549 cell suspension, so that the cell concentration was about $4.8\times10^5$ cells/mL (each 96-well plate was prepared according to 4.8×106 cells). The cells were added into 96-well cell culture plates with 100 μl per well by 8-way guns in a 5% $CO_2$ incubator at 37 C for static culture;

(2) On the second day, wild-type virus (sAd-AY01-TP5, Ad5-Wild-F2) was inoculated, and 1.5 ml of sterilized EP tube was taken and diluted in accordance with 10-1, 10-2, 10-3, 10-4, 10-5, 10-6, 10-7, 10-8 (900 μl serum-free medium+100 μl virus solution) at a multiple ratio. Note that Tip is replaced for each dilution, and it is mixed evenly on a vortex oscillator for 5s for standby.

(3) For cells in 96-well plate, 200 μl tip was connected by vacuum pump to discard the supernatant, followed by cell washing with 1×PBS, and the supernatant was discarded again;

(4) Sensitized cells were treated with 100 L/well for 2 h, the supernatant was discarded, and the complete medium supplemented with 5% FBS was added at 200 μl/well, 37 C and 5% $CO_2$ for static culture. After the lesions were observed on days 5-7, the TCID50; was calculated according to the Reed-Muench method.

Neutralization Experiment (1) Human serum 1200 μl/1.5 EP tube and rabbit serum 500 μl/1.5 EP tube were separately packaged and inactivated in a water bath at 56° C. for 30 min.

(2) Dilution of serum: 8-channel pipette sucks 110 μl of serum-free F12K medium into a 96-well plate, where the first column and the seventh column are empty. After the serum is inactivated, 110 μl of serum is taken into the first column and the second column, respectively. After the second column is mixed evenly, 110 μl is taken into the third column, and diluted into the sixth column by analogy ratio. The last 110 μl of diluent is discarded, and six dilutions of 2-1, 2-2, 2-3, 2-4, 2-5, 2-6 are total, as described above (3) Dilution of virus: 50/100 μL of 200 TCID was used to prepare the virus solution.

(4) Mix: virus and serum. The diluted virus solution was sucked into a 10 cm plate, and 110 μl virus solution was sucked into the diluted serum to be examined by eight rows of guns (110 μl serum+110 μl virus), 37° C., 5% CO2, 1 hour;

(5) After 2 hours, 200 μl Tip was connected with a vacuum pump, the cell supernatant from the 96-well plate was discarded, and 200 μL of cells washed with 1×PBS were aspirated. Then 100 μl of the above mixture was aspirated as the sensory cells. Two wells were parallel. A total of four wells (37° cand 5% $CO_2$) were used for each serum dilution, and the reaction lasted for 2 hrs.

(6) After 2 hours, connect 200 μl Tip with vacuum pump, discard the above mixture, and supplement 200 μL 5% FBS at 37° C. and 5% CO2 for incubation. The results were judged on days 3-7, with the serum dilution causing 50% cytopathic effects as the neutralization titer.

(7) Yin, positive control and blank control were set in the experiment. The positive serum control this time was rabbit serum immunized with wild type sAd-AY01 and Ad5.

Figure 26:
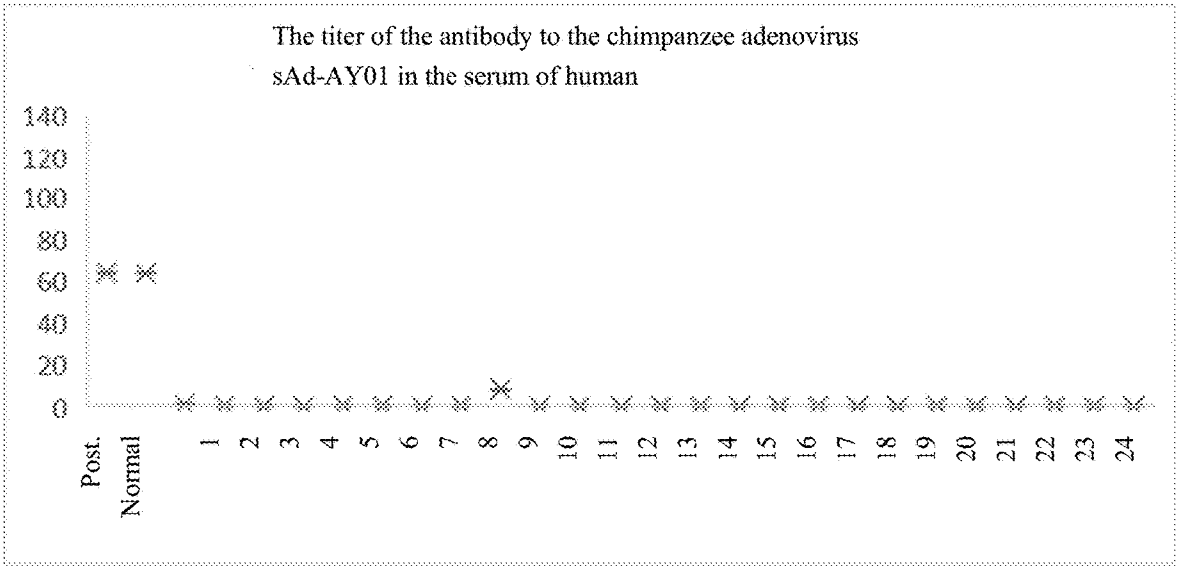
FIG. 26 is the schematic diagram of cytopathic changes in example 12 using sAd-AY01 neutralizing antibody.
Figure 27:
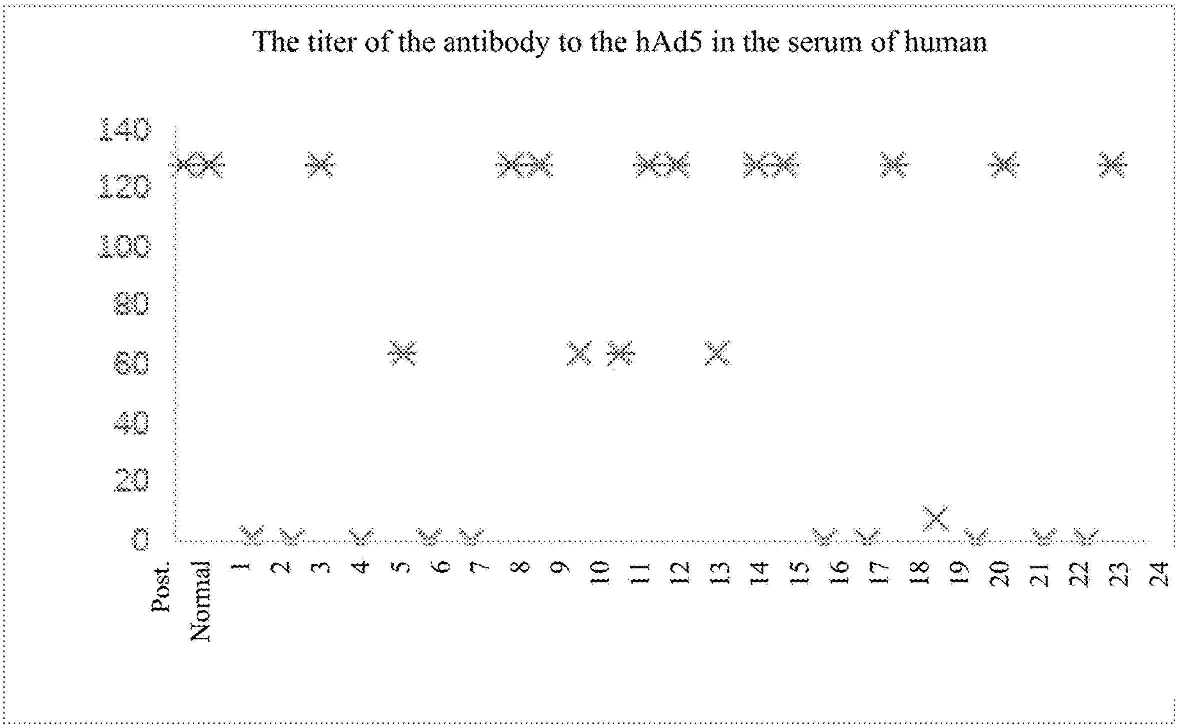
FIG. 27 is the schematic diagram of cytopathic changes in an experiment using an antibody neutralizing hAd5 in example 12.

The neutralizing antibody experiments were conducted with chimpanzee adenovirus sAd-AY01 and human adenovirus type 5, respectively. The results showed that none of the dilutions of the positive serum sickness venom was pathological changes, and all of the dilutions of the negative serum sickness venom were pathological changes. The experiments were established. The specific results are shown in Table 2 and Table 3, FIG. 26 and FIG. 27, where Table 2 and FIG. 26 are pathological changes of sAd-AY01 neutralizing antibody experimental cells, and Table 3 and FIG. 27 are pathological changes of hAd5 neutralizing antibody experimental cells.

TABLE 2

Pathological Changes of 2: sAd-AY01 Neutralizing Antibody Experimental Cells

| sAd-AY01 | 1:2 | 1:4 | 1:8 | 1:16 | 1:32 | 1:64 |
|---|---|---|---|---|---|---|
| Positive sample | – | – | – | – | – | – |
| Inactive virus | + | + | – | – | – | – |
| Blank cell | – | – | – | – | – | – |
| Sample 1 | + | + | + | + | + | + |
| Sample 2 | + | + | + | + | + | + |
| Sample 3 | + | + | + | + | + | + |
| Sample 4 | + | + | + | + | + | + |
| Sample 5 | + | + | + | + | + | + |
| Sample 6 | + | + | + | + | + | + |
| Sample 7 | + | + | + | + | + | + |
| Sample 8 | – | – | + | + | + | + |
| Sample 9 | + | + | + | + | + | + |
| Sample 10 | + | + | + | + | + | + |
| Sample 11 | + | + | + | + | + | + |
| Sample 12 | + | + | + | + | + | + |
| Sample 13 | + | + | + | + | + | + |
| Sample 14 | + | + | + | + | + | + |
| Sample 15 | + | + | + | + | + | + |
| Sample 16 | + | + | + | + | + | + |
| Sample 17 | + | + | + | + | + | + |
| Sample 18 | + | + | + | + | + | + |
| Sample 19 | + | + | + | + | + | + |
| Sample 20 | + | + | + | + | + | + |
| Sample 21 | + | + | + | + | + | + |
| Sample 22 | + | + | + | + | + | + |
| Sample 23 | + | + | + | + | + | + |
| Sample 24 | + | + | + | + | + | + |

TABLE 3 cytopathic condition in 3: hAd5 neutralizing antibody experiment

| Ad5 | 1:4 | 1:8 | 1:16 | 1:32 | 1:64 | 1:128 |
|---|---|---|---|---|---|---|
| Positive sample | – | – | – | – | – | – |
| Inactive virus | + | – | – | – | – | – |
| Blank cell | – | – | – | – | – | – |
| Sample 1 | + | + | + | + | + | + |
| Sample 2 | – | – | – | – | – | – |
| Sample 3 | + | + | + | + | + | + |
| Sample 4 | – | – | – | – | – | + |
| Sample 5 | + | + | + | + | + | + |
| Sample 6 | + | + | + | + | + | + |
| Sample 7 | – | – | – | – | – | – |
| Sample 8 | – | – | – | – | – | – |
| Sample 9 | – | – | – | – | – | + |
| Sample 10 | – | – | – | – | – | + |
| Sample 11 | – | – | – | – | – | – |
| Sample 12 | – | – | – | – | – | – |
| Sample 13 | – | – | – | – | – | + |
| Sample 14 | – | – | – | – | – | – |
| Sample 15 | – | – | – | – | – | – |
| Sample 16 | + | + | + | + | + | + |
| Sample 17 | + | + | + | + | + | + |

TABLE 3-continued

| cytopathic condition in 3: hAd5 neutralizing antibody experiment | | | | | | |
|---|---|---|---|---|---|---|
| Ad5 | 1:4 | 1:8 | 1:16 | 1:32 | 1:64 | 1:128 |
| Sample 18 | – | – | – | – | – | – |
| Sample 19 | – | – | + | + | + | + |
| Sample 20 | + | + | + | + | + | + |
| Sample 21 | – | – | – | – | – | – |
| Sample 22 | + | + | + | + | + | + |
| Sample 23 | + | + | + | + | + | + |
| Sample 24 | – | – | – | – | – | – |
| result | Among the 24 subjects, 15 subjects had neutralizing antibodies with the titer of 1:8 to 1:128 or above, accounting for 62.5% | | | | | |

The results showed that, as shown in Table 2 and FIG. 26, the use of the novel chimpanzee adenovirus sAd-AY01 produced no neutralizing antibody in 24 serum samples of the population, indicating that there was no antibody against the novel chimpanzee adenovirus in the population. As shown in Table 3 and FIG. 27, using human adenovirus type 5, 15 of 24 serum samples had neutralizing antibody with the neutralization titer of 1:8-1:128 or above, accounting for 62.5% of the total number. This indicates that if the novel chimpanzee adenovirus sAd-AY01 is used as a vaccine vector, pre-existing antibodies in the population can be avoided and a better immune effect can be achieved.

Example 13 Immunological Evaluation of Recombinant Novel Chimpanzee Adenovirus psAd-S Vaccine in a Mouse Model 13.1 Detection of Vaccine Humoral Immune Response Twenty SPF-grade mice (6-8 weeks of age) were randomly divided into three groups, five for each group. Mice were immunized with psAd-S vaccine according to the groupings shown in Table 4. The injection method was as follows: intramuscular injection was performed on the medial aspect of the posterior thigh. Injection dose: 100 ul.

TABLE 4

| Groups of Vaccinated Mice | | | | |
|---|---|---|---|---|
| group | Vector vaccine | dosage | Immune mode | Number of mice |
| High dose | psAd-S | 1 * 10^8 FFU | intramuscular injection | five |
| low dose | psAd-S | 1 * 10^7 FFU | intramuscular injection | five |
| control | psAdΔE1ΔE3 | 1 * 10^7 FFU | intramuscular injection | five |

Blood was collected 14 days after immunization and serum was separated from SARS-CoV-2(2019-nCOV)Spike S1 antibody titer detection kit (mouse), Art.No. KIT007, for detecting anti-SARS-CoV-2 (2019-nCOV) Spikes1 antibody level in mouse serum samples.

The detection principle was as follows: an indirect ELSA method was used to coat novel coronavirus S1 protein on a solid phase carrier, and a sample to be detected was added for incubation. The anti-novel coronavirus antibody in the sample was combined with the protein on the solid phase carrier, and after plate washing, the anti-mouse IgG antibody labeled with horseradish peroxidase (HRP) was added to form an antigen-antibody-enzyme labeled antibody complex. After coloration with the substrate TMB, TMB is converted to blue under the catalysis of peroxidase and finally yellow under the action of acid, and the absorbance (OD value) at 450 m is read, and the OD value at 450 m is positively correlated with the anti-novel coronavirus antibody content in the sample.

Calculate an enzyme label strip required for detect a sample, taking out that enzyme label strip from the aluminum foil bag, putting the rest of the enzyme label strip back into the aluminum foil bag and seal the bag mouth, preserving at low temperature, washing the plate with 1*washing buffer solution and soaking Imin at 300 mu/hole, patting the enzyme label plate for the next cleaning, adding the sample to be detected into the plate for five times of washing, diluting serum with 1*dilution buffer solution at 1:2000, incubating at 100/hole for 2 hours at room temperature, discarding the liquid in the hole, patting the enzyme label plate for drying, washing the plate with 1*washing buffer solution and soaking at 300 μL/hole for 1 min, and patting for drying The anti-mouse IgG antibody, –HRP1:100, was diluted with 1× dilution buffer, and 100 μl/well was added to the ELISA plate, mixed, and incubated for 1 hour at room temperature. The liquid in the wells was discarded, and the ELISA plate was pat dry. The plate was washed with 1× washing buffer solution, and Imin was immersed in 300 μl/well. The ELISA plate was pat dry for the next washing, and the plate was washed five times in total. The pre-prepared substrate solution was added into the ELISA plate at 200 μl/well, mixed evenly, and incubated for 20 minutes at room temperature in the dark. Add 50/well stop solution to the ELISA plate and gently shake the plate until uniform color development is achieved. Read the light absorption value for OD450 mm.

Figure 28:
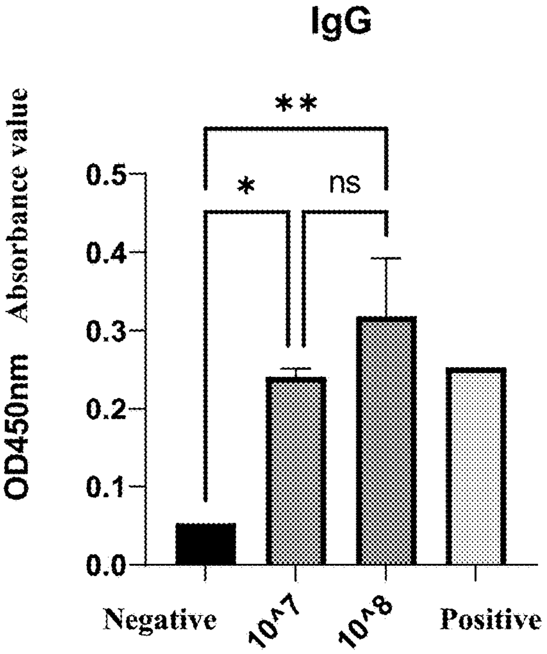
FIG. 28 is the results of IgG antibody titer after intramuscular injection of psAd-S vaccine by ELISA in example 13.

The test results are shown in FIG. 28. Two weeks after the intramuscular injection of psAd-S vaccine, the mice were able to produce high concentrations of IgG antibodies against spike protein. The serum of mice injected with 1*10 8 FFU dose was significantly different from that of the negative control group, and the serum of mice injected with 1*10 7 FFU dose was also significantly different from that of the control, and the humoral immune response induced by the high dose group was higher. (ns, P≥0.05; *, P<0.05; , P<0.01; *, P<0.001; ****, P<0.0001)

13.2 Detection of Cellular Immune Response

Ten SPF-grade mice (6-8 weeks of age) were randomly divided into two groups, five for each group. Mice were immunized with psAd-S vaccine according to the groupings shown in Table 5. The injection method was as follows: intramuscular injection was performed on the medial aspect of the posterior thigh. Injection dose: 100 ul.

TABLE 5

| Groups of Vaccinated Mice | | | | |
|---|---|---|---|---|
| group | Vector vaccine | dosage | Immune mode | Number of mice |
| experimental group | psAd-S | 1 * 10^7 FFU | intramuscular injection | five |
| Control group | psAdΔE1ΔE3 | 1 * 10^7 FFU | intramuscular injection | five |

Figure 29:
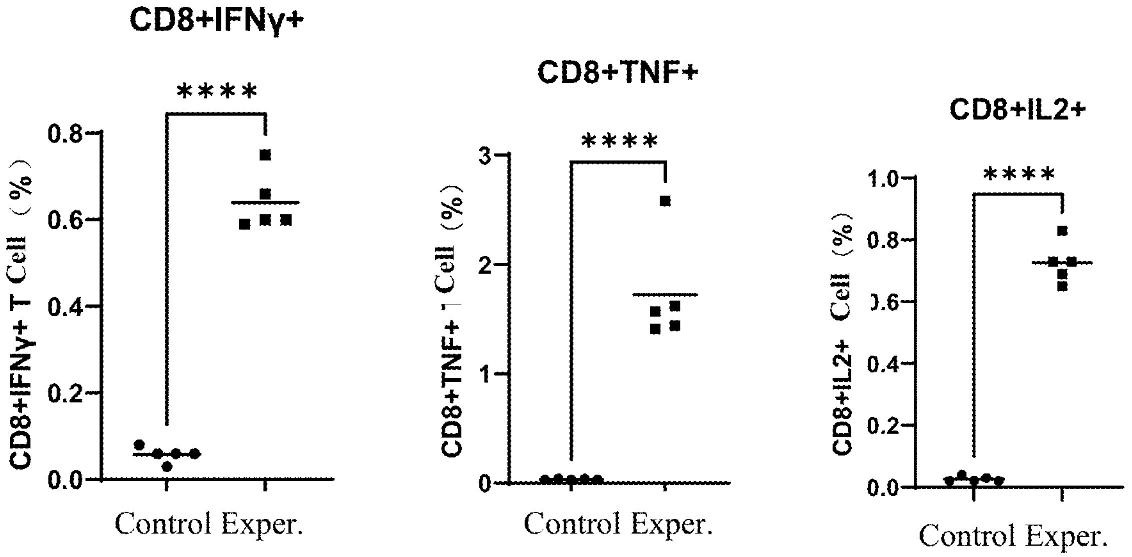
FIG. 29 is the results of CD8+ T cell response induced by the vaccine psAd-S of example 13.
Figure 30:
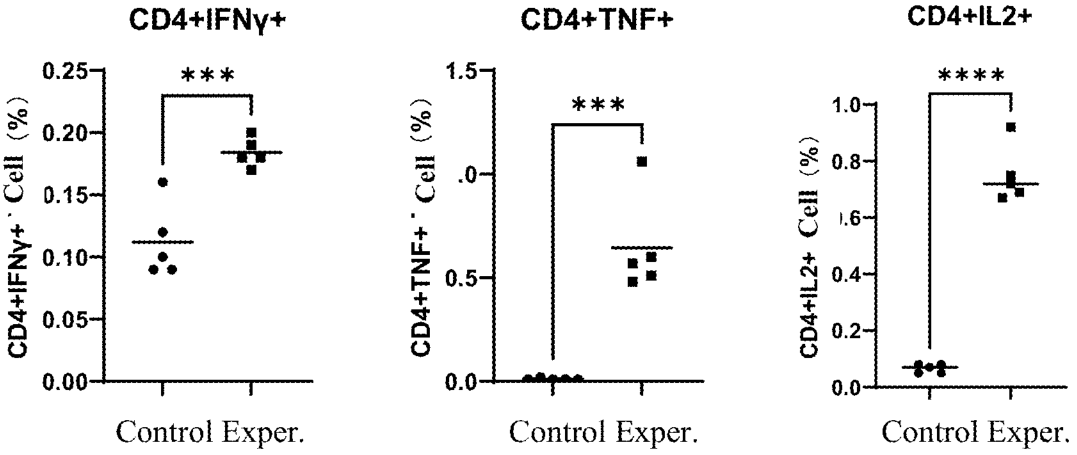
FIG. 30 is the results of CD4+ T cell response induced by the vaccine psAd-S of example 13.
Figure 31:
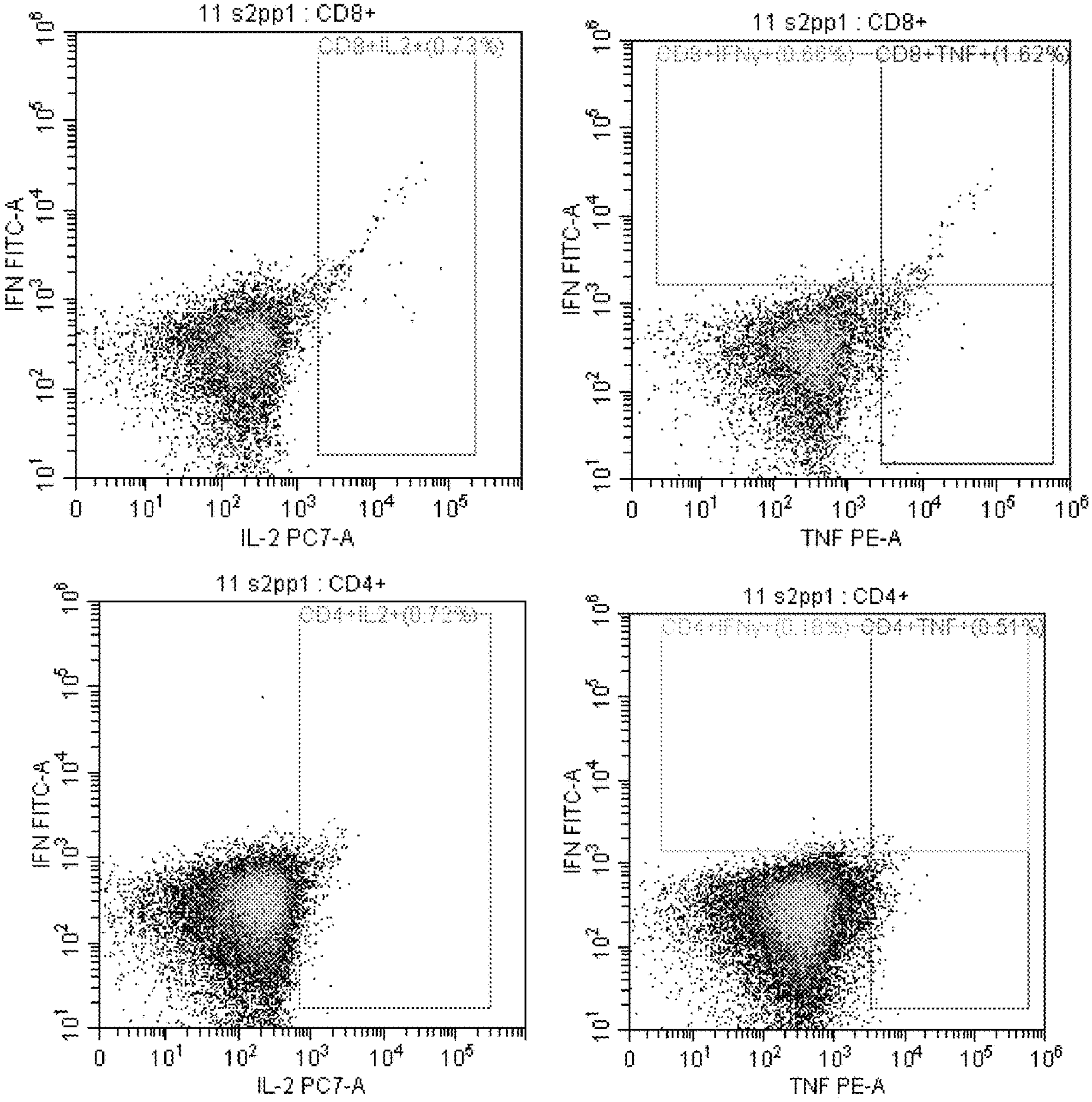
FIG. 31 is the results of cellular immune response after intramuscular injection of vaccine psAd-S according to example 13.
Figure 32:
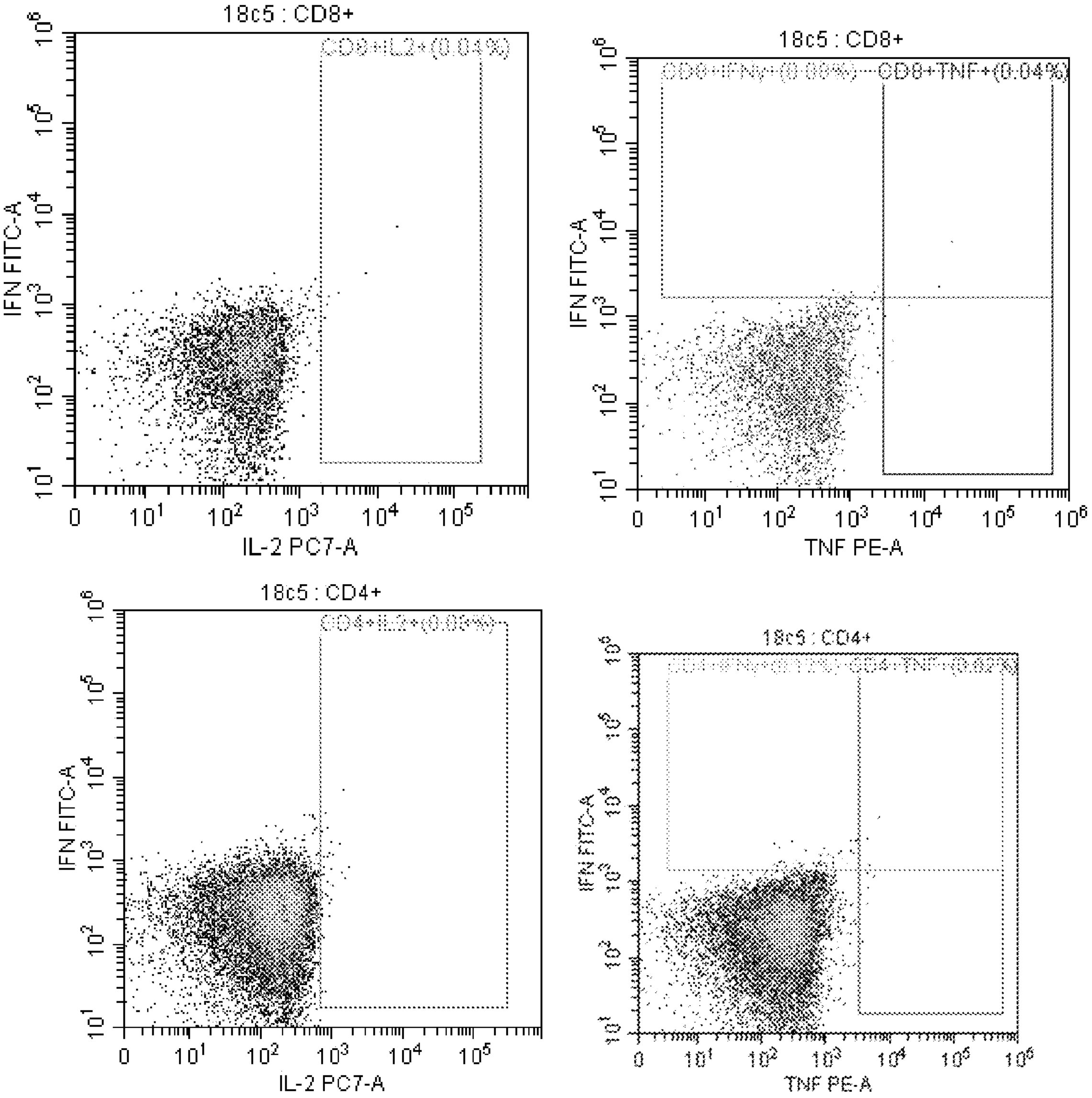
FIG. 32 is A blank control immune response representative diagram of Example 13.

The mice were sacrificed 14 days after immunization, and the splenic lymphocytes were isolated. BHK21 cells transfected with the shuttle plasmid pSsAdE1-WPRE-S were stimulated and cultured for 6 hours, and cytokine secretion was blocked by adding a protein secretion blocker. After 6 hours, Fc receptors were blocked, dead cells and cell surface molecular markers were stained, and intracellular cytokines were stained after the cells were fixed and perforated. Cell surface markers included CD4 and CD8, and intracellular cytokines included IFNγ, IL2 and TNF. The expression levels of IFNγ, IL2 and TNF in CD4+ T cells and CD8+ T cells stimulated by the target protein were analyzed by flow cytometry (CyExpert).

psAd-S-induced CD8+ T-cell and CD4+ T-cell immune responses are shown in FIGS. 29 and 30, and representative results are shown in FIGS. 31 and 32. FIG. 31 is a representative diagram of cellular immune response after intramuscular injection of psAd-S, and FIG. 32 is a representative diagram of blank control immune response. The results showed that, 14 days after immunization, after the spleen cells were stimulated by Spike protein, the levels of IFNγ, TNFα and IL2 expressed in CD8+ T cells were significantly higher than those in the psAdΔE1ΔE3 vehicle control group (Control) ($P<0.05$). After stimulation, the expression levels of IFNγ, TNFα and IL2 in CD4+ T cells were also significantly higher than those in the PSAD Δ E1 Δ E3 vehicle control group (Control) ($P<0.05$).

13.3 SARS-COV-2 Pseudovirus Simulated Neutralization Antibody Experiment

SARS-COV-2 pseudovirus neutralization test kit is purchased from Nanjing Kingsri Biotechnology Co., Ltd. on the principle that the envelope glycoprotein in the lentivirus vector is replaced by Covid-19 S protein to form a pseudovirus simulating Covid-19 infection. Pseudoviruses infect target cells through surface S proteins and express reporter luciferase genes. Neutralizing agents (such as antibodies) can block the binding of S protein and ACE2, thereby preventing pseudovirus infection of the host cells. By detecting the expression level of the reporter gene luciferase, the degree to which the virus is blocked can be deduced for screening or verification of the neutralizing agent.

The experimental steps were as follows: The mouse serum, positive control and negative control collected in the cell immune response test were diluted and mixed with the diluted HRP-RBD in a 1:1 manner and incubated at 37 C for 30 minutes. Incubate 100 U of the mixture in the corresponding well plate for 15 minutes at 37 C; Wash the well plates 4 times with 260 ul of 1× Wash buffer; Then 100 ul TMB buffer was added and incubated for 15 min at 20-25 C in the dark. Adding 50 ul of termination buffer; OD450 reads the absorbance. The result are shown in table 6:

TABLE 6

Simulated Neutralization Antibody Test of SARS-CoV-2 Pseudovirus

| serum | OD450 | suppression ratio | Dilution multiple | result |
|---|---|---|---|---|
| 10 8 1 | 0.2672 | 81.9% | 256 | positive |
| 10 8 2 | 0.5680 | 61.6% | 256 | positive |
| 10 8 3 | 0.6779 | 54.1% | 256 | positive |
| 10 8 4 | 0.4522 | 69.4% | 256 | positive |
| 10 8 5 | 0.6728 | 54.5% | 256 | positive |
| 10 7 1 | 0.9243 | 37.5% | 256 | positive |
| 10 7 2 | 1.0025 | 32.2% | 256 | positive |
| 10 7 3 | 0.9389 | 36.5% | 256 | positive |
| 10 7 4 | 1.0420 | 29.5% | 256 | positive |
| 10 7 5 | 0.9300 | 37.1% | 256 | positive |
| positive control | 0.0816 | \ | 10 | \ |
| negative control | 1.4780 | \ | 10 | \ |

Among them: quality control: positive control <0.3, negative control>1.0; Inhibition rate=(1−sample OD value/negative control OD value)*100%; Judgement: Positive inhibition rate ≥20% and negative inhibition rate <20%.

In summary, after mice were injected with the total dose of 10^8 FFU vaccine (diluted with PBS buffer) and 10^7 FFU (diluted with PBS buffer), they could induce strong humoral and cellular immune responses, which were significantly different from those in the control group. At the same time, the collected serum can play a blocking role in the simulated neutralization antibody experiment. The results showed that our psad-S vaccine could protect Covid-19, which had guiding significance for the development of vaccine in COVID-19.

Although the present invention has been disclosed as above, the present invention is not limited thereto. Various changes and modifications may be made by those skilled in the art without departing from the spirit and scope of the present invention, and the scope of the present invention should be determined by the scope of the appended claims.

The invention claimed is:

1. A chimpanzee adenovirus having a nucleotide sequence, wherein the chimpanzee adenovirus comprises a conserved region, E1 and E3 genes are deleted in the conserved region, and the nucleotide sequence after deletion is represented by SEQ ID NO. 4.

2. The chimpanzee adenovirus according to claim 1, wherein the chimpanzee adenovirus further comprises a target gene.

3. The chimpanzee adenovirus according to claim 2, wherein the target gene is a virus, a bacterium, a tumor gene or a gene fragment thereof.

4. The chimpanzee adenovirus according to claim 2, wherein the target gene is located in the E1 gene of the chimpanzee adenovirus.

* * * * *

SEQUENCE LISTING

```
<160> NUMBER OF SEQ ID NOS: 61

<210> SEQ ID NO 1
<211> LENGTH: 36686
<212> TYPE: DNA
<213> ORGANISM: Chimpanzee Adenovirus

<400> SEQUENCE: 1

atcatcaata atatacctca aacttttggt gcgcgttaat atgcaaatga ggtgtttgaa      60

tttggggatg cggggctgtg attggccgag agacgggcga ccgttagggg cggggcgggt     120

gacgttttga tgacgtggcc gtgaggcgga gccggtttgc aagttctcgt gggaaaagtg     180

acgtcaaacg aggtgtggtt tgaacacgga aatactcaat tttcccgcgc tctctgacag     240

gaaatgaggt gtttctgggc ggatgcaagt gaaaacgggc cattttcgcg cgaaaactga     300

atgaggaagt gaaaatctga gtaatttcgc gtttatggca gggaggagta tttgccgagg     360

gccgagtaga ctttgaccga ttacgtgggg gtttcgatta ccgtattttt cacctaaatt     420

tccgcgtacg gtgtcaaagt ccggtgtttt tacgtaggtg tcagctgatc gccagggtat     480
```

```
ttaaacctgc gctctctagt caagaggcca ctcttgagtg ccagcgagta gagttttctc    540
ctccgcgccg cgagtcagat ctacactttg aaagatgagg cacctgagag acctgcccgg    600
taatgttttc ctggctactg ggaacgagat tctggaactg gtggtggacg ccatgatggg    660
tgacgaccct cctgagcccc ctaccccatt tgaggcgcct tcgctgtacg atttgtatga    720
tctggaggtg gatgtgcccg agaacgaccc caacgaggag gcggtgaatg atttgtttag    780
cgatgccgcg ctgctggctg ccgagcaggc taatacggac tctggctcag acagcgattc    840
ctctctccat accccgagac ccggcagagg tgagaaaaag atccccgagc ttaaagggga    900
agagctcgac ctgcgctgct atgaggaatg cttgcctccg agcgatgatg aggaggacga    960
ggaggcgatt cgagctgcag cgagcgaggg agtgaaagct gcgggcgaga gctttagcct   1020
ggactgtcct actctgcccg gacacggctg taagtcttgt gaatttcatc gcatgaatac   1080
tggagataag aatgtgatgt gtgccctgtg ctatatgaga gcttacaacc attgtgttta   1140
cagtaagtgt gattaacttt agctgggaag gcagagggtg actgggtgct gactggttta   1200
tttatgtatg tattctttat gtgtaggtcc cgtctctgac gcagatgaga cccccacttc   1260
agagtgcatt tcatcacccc cagaaattgg cgaggaaccg cccgaagata ttattcatag   1320
accagttgca gtgagagtca ccgggcggag agcagctgtg gagagtttgg atgacttgct   1380
acagggtggg gatgaacctt tggacttgtg tacccggaaa cgccccaggc actaagtgcc   1440
acacatgtgt gtttacttaa ggtgatgtca gtatttatag ggtgtggagt gcaataaaaa   1500
tatgtgttga ctttaagtgc gtggtttatg actcaggggt ggggactgtg ggtatataag   1560
caggtgcaga cctgtgtggt cagttcagag caggactcat ggagatctgg acggtcttgg   1620
aagactttca ccagactaga cagctgctag agaactcatc ggagggagtc tcttacctgt   1680
ggagattctg cttcggtggg gctctagcta agctagtcca tagggccaaa caggattata   1740
aggatcaatt tgaggatatt ttgagagagt gtcctggtat tttgactctt ctcaacttgg   1800
gccatcagtc tcactttaac cagagtattc tgagagccct tgacttttct actcctggca   1860
gaactaccgc cgcggtagcc ttttttgcct ttattcttga caaatggagt caagaaaccc   1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaggaggat cgagaagaga acccgagagc cggtctggac cctccggtgg   2160
cggaggagga ggagtagctg acttgtttcc cgagctgcgc cgggtgctga ctaggtcttc   2220
cagtggacgg gagagggggga ttaagcggga gaggcatgag gagactagtc acagaactga   2280
actgactgtc agtctgatga gccgcaggcg cccagaatcg gtgtggtggc atgaggtgca   2340
gtcgcagggg atagatgagg tctcggtgat gcatgagaaa tattccctag aacaagtcaa   2400
gacttgttgg ttggagcctg aggatgattg ggaggtagcc atcaggaatt atgccaagtt   2460
ggctctgaag ccagataaga agtacaagat taccaaactg attaatatca gaaattcctg   2520
ctacatttcg gggaatgggg ccgaggtgga gatcagtacc caggagaggg tggccttcag   2580
atgctgcatg atgaatatgt acccgggagt ggtgggcatg gagggagtca cctttatgaa   2640
cgcgaggttc aggggtgatg ggtataatgg ggtggtcttt atggccaaca ccaagctgac   2700
agtgcacgga tgctccttct ttggcttcaa taacatgtgc atcgaggcct ggggcagtgt   2760
ttcagtgagg ggatgcagct tttcagccaa ctggatgggg gtcgtgggca gaaccaagag   2820
caaggtgtca gtgaagaaat gcctgttcga gaggtgccac ctgggggtga tgagcgaggg   2880
```

```
cgaagccaaa gtcaaacact gcgcctctac cgagacgggc tgctttgtgc tgatcaaggg   2940
caatgccaaa gtcaagcata atatgatctg tggggcctcg gatgagcgcg gctaccagat   3000
gctgacctgc gccggtggga acagccatat gctggccacc gtgcatgtgg cctcgcaccc   3060
ccgcaagaca tggcccgagt tcgagcacaa cgtcatgacc cgctgcaatg tgcacctggg   3120
ttcccgccga ggcatgttca tgccctacca gtgcaacatg caatttgtga aggtgctgct   3180
ggagcccgat gccatgtcca gagtgagcct gacgggggtg tttgacatga atgtggagct   3240
gtggaaaatt ctgagatatg atgaatccaa gaccaggtgc cgggcctgcg aatgcggagg   3300
caagcacgcc aggcttcagc ccgtgtgtgt ggaggtgacg gaggacctgc gacccgatca   3360
tttggtgttg tcctgcaacg ggacggagtt cggctccagc ggggaagaat ctgactagag   3420
tgagtagtgt ttgggggtgg gtgggagcct gcatgagggg cagaatgact aaaatctgtg   3480
tttttctgtg tgttgcagca gcatgagcgg aagcgcctcc tttgagggag gggtattcag   3540
cccttatctg acggggcgtc tcccctcctg ggctggagtg cgtcagaatg tgatgggatc   3600
cacggtggac ggccggcccg tgcagcccgc gaactcttca accctgacct acgcgaccct   3660
gagctcctcg tccgtggacg cagctgccgc cgcagctgct gcttccgccg ccagcgccgt   3720
gcgcggaatg gccctgggtg ccggctacta cagctctctg gtggccaact cgagttccac   3780
caataatccc gccagcctga acgaggagaa gctgctgctg ctgatggccc agctcgaggc   3840
cctgacccag cgcctgggcg agctgaccca gcaggtggct cagctgcagg cggagacgcg   3900
ggccgcggtt gccacggtga aaaccaaata aaaaatgaat caataaataa acggagacgg   3960
ttgttgattt taacacagag tcttgaatct ttatttgatt tttcgcgcgc ggtaggccct   4020
ggaccaccgg tctcgatcat tgagcacccg gtggattttt tccaggaccc ggtagaggtg   4080
ggcttggatg ttgaggtaca tgggcatgag cccgtcccgg gggtggaggt agctccattg   4140
cagggcctcg tgctcggggg tggtgttgta aatcacccag tcatagcagg ggcgcagggc   4200
gtggtgctgc acgatgtcct tgaggaggag actgatggcc acgggcagcc ccttggtgta   4260
ggtgttgacg aacctgttga gctgggaggg atgcatgcgg ggggagatga gatgcatctt   4320
ggcctggatc ttgagattgg cgatgttccc gcccagatcc cgccgggggt tcatgttgtg   4380
caggaccacc agcacggtgt atccggtgca cttggggaat ttgtcatgca acttggaagg   4440
gaaggcatga aagaatttgg agacgccctt gtgaccgccc aggttttcca tgcactcatc   4500
catgatgatg gcaatgggcc cgtgggcggc ggcctgggca aagacgtttc gggggtcgga   4560
cacatcgtag ttgtggtcct gggtgagctc gtcataggcc attttaatga atttgggacg   4620
gagggtgccc gattggggga cgaaggtgcc ctcgatcccg gggcgtagt tgccctcgca   4680
gatctgcatc tcccaggcct tgagctcgga ggggggggatc atgtccacct gcggggcgat   4740
gaaaaaaacg gtttccgggg cgggggagat gagctgcgcc gaaagcaggt tccggagcag   4800
ctgggacttg ccgcagccgg tgggaccgta gatgaccccg atgaccggct gcaggtggta   4860
gttgagggag agacagctgc cgtcctcgcg gaggaggggg gccacctcgt tcatcatctc   4920
gcgcacatgc atgttctcgc gcacgagttc cgccaggagg cgctcgcccc ccagcgagag   4980
gagctcttgc agcgaggcga agtttttcag cggcttgagc ccgtcggcca tgggcatttt   5040
ggagagggtc tgttgcaaga gttccagacg gtcccagagc tcggtgatgt gctctagggc   5100
atctcgatcc agcagacctc ctcgtttcgc gggttggggc gactgcggga gtagggcacc   5160
aggcgatggg cgtccagcga ggccagggtc cggtccttcc agggccgcag ggtccgcgtc   5220
```

agcgtggtct ccgtcacggt gaaggggtgc gcgccgggct gggcgcttgc gagggtgcgc 5280
ttcaggctca tccggctggt cgagaaccgc tcccggtcgg cgccctgcgc gtcggccagg 5340
tagcaattga gcatgagttc gtagttgagc gcctcggccg cgtggccctt ggcgcggagc 5400
ttacctttgg aagtgtgtcc gcagacggga cagaggaggg acttgagggc gtagagcttg 5460
ggggcgagga agacggactc gggggcgtag gcgtccgcgc cgcagctggc gcagacggtc 5520
tcgcactcca cgagccaggt gaggtcgggc cggtcggggt caaaaacgag gtttcctccg 5580
tgctttttga tgcgtttctt acctctggtc tccatgagct cgtgtccccg ctgggtgaca 5640
aagaggctgt ccgtgtcccc gtagaccgac tttatgggtc ggtcctcgag cggggtgccg 5700
cggtcctcgt cgtagaggaa ccccgcccac tccgagacga aggcccgggt ccaggccagc 5760
acgaaggagg ccacgtggga ggggtagcgg tcgttgtcca ccagcgggtc caccttctcc 5820
agggtatgca agcacatgtc cccctcgtcc acatccagga aggtgattgg cttgtaagtg 5880
taggccacgt gaccgggggt cccggccggg ggggtataaa agggggcggg cccctgctcg 5940
tcctcactgt cttccggatc gctgtccagg agcgccagct gttggggtag gtattccctc 6000
tcgaaggcgg gcatgacctc ggcactcagg ttgtcagttt ctagaaacga ggaggatttg 6060
atattgacgg tgccgttgga gacgcctttc atgagcccct cgtccatctg gtcagaaaag 6120
acgatctttt tgttgtcgag cttggtggcg aaggagccgt agagggcgtt ggagagcagc 6180
ttggcgatgg agcgcatggt ctggttcttt tccttgtcgg cgcgctcctt ggcggcgatg 6240
ttgagctgta cgtactcgcg cgccacgcac ttccattcgg ggaagacggt ggtgagctcg 6300
tcgggcacga ttctgacccg ccagccgcgg ttgtgcaggg tgatgaggtc cacgctggtg 6360
gccacctcgc cgcgcagggg ctcgttggtc cagcagaggc gcccgccctt gcgcgagcag 6420
aaggggggca gcgggtccag catgagctcg tcgggggggt cggcgtccac ggtgaagatg 6480
ccgggcagga gctcggggtc aaagtagctg atgcaggtgc ccagatcgtc cagcgccgct 6540
tgccagtcgc gcacggccag cgcgcgctcg taggggctga ggggcgtgcc ccagggcatg 6600
gggtgcgtga gcgcggaggc gtacatgccg cagatgtcgt agacgtagag gggctcctcg 6660
aggacgccga tgtaggtggg gtagcagcgc cccccgcgga tgctggcgcg cacgtagtcg 6720
tacagctcgt gcgagggcgc gaggagcccc gtgccgagat tggagcgctg cggcttttcg 6780
gcgcggtaga cgatctggcg gaagatggcg tgggagttgg aggagatggt gggcctctgg 6840
aagatgttga agtgggcgtg gggcaggccg accgagtccc tgatgaagtg ggcgtaggag 6900
tcctgcagct tggcgacgag ctcggcggtg acgaggacgt ccagggcgca gtagtcgagg 6960
gtctcttgga tgatgtcata cttgagctgg cccttctgct tccacagctc gcggttgaga 7020
aggaactctt cgcggtcctt ccagtactct tcgagggggga acccgtcctg atcggcacgg 7080
taagagccca ccatgtagaa ctggttgacg gccttgtagg cgcagcagcc cttctccacg 7140
gggagggcgt aagcttgcgc ggccttgcgc agggaggtgt gggtgagggc gaaggtgtcg 7200
cgcaccatga ccttgaggaa ctggtgcttg aagtcgaggt cgtcgcagcc gccctgctcc 7260
cagagttgga agtccgtgcg cttcttgtag gcggggttgg gcaaagcgaa agtaacatcg 7320
ttgaagagga tcttgcccgc gcggggcatg aagttgcgag tgatgcggaa aggctggggc 7380
acctcggccc ggttgttgat gacctgggcg gcgaggacga tctcgtcgaa gccgttgatg 7440
ttgtgcccga cgatgtagag ttccacgaat cgcgggcggc ccttgacgtg gggcagcttc 7500
ttgagctcgt cgtaggtgag ctcggcgggg tcgctgaggc cgtgctgctc gagggcccag 7560
tcggcgacgt gggggttggc gctgaggaag gaagtccaga gatccacggc cagggcggtc 7620
tgcaagcggt cccggtactg acggaactgc tggcccacgg ccatttttttc gggggtgacg 7680
cagtagaagg tgcgggggtc gccgtgccag cggtcccact tgagctggag ggcgaggtcg 7740
tgggcgagct cgacgagcgg cgggtccccg gagagtttca tgaccagcat gaaggggacg 7800
agctgcttgc cgaaggaccc catccaggtg taggtttcca catcgtaggt gaggaagagc 7860
ctttcggtgc gaggatgcga gccgatgggg aagaactgga tctcctgcca ccagttggag 7920
gaatggctgt tgatgtgatg gaagtagaaa tgccgacggc gcgccgagca ctcgtgcttg 7980
tgtttataca agcgtccgca gtgctcgcaa cgctgcacgg gatgcacgtg ctgcacgagc 8040
tgtacctgag ttcctttgac gaggaatttc agtgggcagt ggagcgctgg cggctgcatc 8100
tggtgttgta ctacgtcctg gccatcggcg tggccatcgt ctgcctcgat ggtggtcatg 8160
ctgacgaggc cgcgcgggag gcaggtccag acctcggctc ggacgggtcg gagagcgagg 8220
acgagggcgc gcaggccgga gctgtccagg gtcctgagac gctgcggagt caggtcagtg 8280
ggcagcggcg gcgcgcggtt gacttgcagg agcttttcca gggcgcgcgg gaggtccaga 8340
tggtacttga tctccacggc gccgttggtg gcaacgtcca cggcttgcag ggtgccgtgc 8400
ccctggggcg ccaccaccgt gccccgtttc tttttgggcg ctggcggcgg cggctccatg 8460
cttagaatcg gcggcgagga cgcgcgccgg gcggcagggg cggctcgggg cccggaggca 8520
ggggcggcag gggcacgtcg gcgccgcgcg cgggcaggtt ctggtactgc gcccggagaa 8580
gactggcgtg agcgacgacg cgacggttga cgtcctggat ctgacgcctc tgggtgaagg 8640
ccacgggacc cgtgagtttg aacctgaaag agagttcgac agaatcaatc tcggtatcgt 8700
tgacggcagc ctgccgcagg atctcttgca cgtcgcccga gttgtcctgg taggcgatct 8760
cggtcatgaa ctgctcgatc tcctcctcct gaaggtctcc gcggccggcg cgctcgacgg 8820
tggccgcgag gtcgttggag atgcggccca tgagctgcga gaaggcgttc atgccggcct 8880
cgttccagac gcggctgtag accacggctc cgtcggggtc gcgcgcgcgc atgaccacct 8940
gggcgaggtt gatctccacg tggcgcgtga agaccgcgta gttgcagagg cgctggtaga 9000
ggtagttgag cgtggtggcg atgtgctcgg tgacgaagaa gtacatgatc cagcggcgga 9060
gcggcatctc gctgacgtcg cccagggctt ccaagcgctc catggcctcg tagaagtcca 9120
cggcgaagtt gaaaaactgg gagttgcgcg ccgagacggt caactcctcc tccagaagac 9180
ggatgagctc ggcgatggtg gcgcgcacct cgcgctcgaa ggccccgggg ggctcctctt 9240
cttccatctc ctcctcctct tcctcctcct ccactaacat ctcttctact tcctcctcag 9300
gaggcggcgg cgggggaggg gccctgcgtc gccggcggcg cacgggcaga cggtcgatga 9360
agcgctcgat ggtctccccg cgccggcgac gcatggtctc ggtgacggcg cgcccgtcct 9420
cgcggggccg cagcgtgaag acgccgccgc gcatctccag gtggccgccg ggggggtctc 9480
cgttgggcag ggagagggcg ctgacgatgc atcttatcaa ttggcccgta gggactccgc 9540
gcaaggacct gagcgtctcg agatccacgg gatccgaaaa ccgctgaacg aaggcttcga 9600
gccagtcgca gtcgcaaggt aggctgagcc cggtttcttg ttcttcgggt atttggtcgg 9660
gaggcgggcg ggcgatgctg ctggtgatga agttgaagta ggcggtcctg agacggcgga 9720
tggtggcgag gagcaccagg tccttgggcc cggcttgctg gatgcgcaga cggtcggcca 9780
tgccccaggc gtggtcctga cacctggcga ggtccttgta gtagtcctgc atgagccgct 9840
ccacgggcac ctcctcctcg cccgcgcggc cgtgcatgcg cgtgagcccg aacccgcgct 9900
ggggctggac gagcgccagg tcggcgacga cgcgctcggc gaggatggcc tgctggatct 9960

-continued gggtgagggt ggtctggaag tcgtcgaagt cgacgaagcg gtggtaggct ccggtgttga 10020
tggtgtagga gcagttggcc atgacggacc agttgacggt ctggtggccg gggcgcacga 10080
gctcgtggta cttgaggcgc gagtaggcgc gcgtgtcgaa gatgtagtcg ttgcaggtgc 10140
gcacgaggta ctggtatccg acgaggaagt gcggcggcgg ctggcggtag agcggccatc 10200
gctcggtggc gggggcgccg ggcgcgaggt cctcgagcat gaggcggtgg tagccgtaga 10260
tgtacctgga catccaggtg atgccggcgg cggtggtgga ggcgcgcggg aactcgcgga 10320
cgcggttcca gatgttgcgc agcggcagga agtagttcat ggtggccgcg gtctggcccg 10380
tgaggcgcgc gcagtcgtgg atgctctaga catacgggca aaaacgaaag cggtcagcgg 10440
ctcgactccg tggcctggag gctaagcgaa cgggttgggc tgcgcgtgta ccccggttcg 10500
agtccctgct cgaatcaggc tggagccgca gctaacgtgg tactggcact cccgtctcga 10560
cccaagcctg ctaacgaaac ctccaggata cggaggcggg tcgttttggc aattttcgtc 10620
aggccggaaa tgaaactagt aagcgcggaa agcggccgcc cgcgatggct cgctgccgta 10680
gtctggagaa agaatcgcca gggttgcgtt gcggtgtgcc ccggttcgag cctcggcgct 10740
cgtgccggcc ggattccgcg gctaacgtgg gcgtggctgc cccgtcgttt ccaagacccc 10800
ttagccagcc gacttctcca gttacggagc gagcccctct tttttttttt tcttgtgttt 10860
ttgccagatg catcccgtac tgcggcagat gcgcccccac cctccaccac aaccgcccct 10920
accgcagcag cagcaacagc cggcgcttct gcccccgccc cagcagcagc agccagccac 10980
taccgcggcg gccgccgtga gcggagccgg cgttcagtat gacctggcct tggaagaggg 11040
cgaggggctg gcgcggctgg gggcgtcgtc gccggagcgg cacccgcgcg tgcagatgaa 11100
aagggacgct cgcgaggcct acgtgcccaa gcagaacctg ttcagagaca ggagcggcga 11160
ggagcccgag gagatgcgcg cctcccgctt ccacgcgggg cgggagctgc ggcgcggcct 11220
ggaccgaaag cgggtgctga gggacgagga tttcgaggcg gacgagctga cggggatcag 11280
ccccgcgcgc gcgcacgtgg ccgcggccaa cctggtcacg gcgtacgagc agaccgtgaa 11340
ggaggagagc aacttccaaa aatccttcaa caaccacgtg cgcacgctga tcgcgcgcga 11400
ggaggtgacc ctgggcctga tgcacctgtg ggacctgctg gaggccatcg tgcagaaccc 11460
cacgagcaag ccgctgacgg cgcagctgtt tctggtggtg cagcacagtc gggacaacga 11520
gacgttcagg gaggcgctgc tgaatatcac cgagcccgag ggccgctggc tcctggacct 11580
ggtgaacatt ctgcagagca tcgtggtgca ggagcgcggg ctgccgctgt ccgagaagct 11640
ggcggccatc aacttctcgg tgctgagcct gggcaagtac tacgctagga agatctacaa 11700
gaccccgtac gtgcccatag acaaggaggt gaagatcgac gggttttaca tgcgcatgac 11760
cctgaaagtg ctgaccctga gcgacgatct gggggtgtac cgcaacgaca ggatgcaccg 11820
cgcggtgagc gccagccgcc ggcgcgagct gagcgaccag gagctgatgc acagcctgca 11880
gcgggccctg accggggccg ggaccgaggg ggagagctac tttgacatgg gcgcggacct 11940
gcgctggcag cccagccgcc gggccttgga agctgccggc ggttccccct acgtggagga 12000
ggtggacgat gaggaggagg agggcgagta cctggaagac tgatggcgcg accgtatttt 12060
tgctagatgc agcaacagcc accgccgcct cctgatcccg cgatgcgggc ggcgctgcag 12120
agccagccgt ccggcattaa ctcctcggac gattggaccc aggccatgca acgcatcatg 12180
gcgctgacga cccgcaatcc cgaagccttt agacagcagc ctcaggccaa ccggctctcg 12240
gccatcctgg aggccgtggt gccctcgcgc tcgaacccca cgcacgagaa ggtgctggcc 12300
atcgtgaacg cgctggtgga gaacaaggcc atccgcggcg acgaggccgg gctggtgtac 12360
aacgcgctgc tggagcgcgt ggcccgctac aacagcacca acgtgcagac gaacctggac 12420
cgcatggtga ccgacgtgcg cgaggcggtg tcgcagcgcg agcggttcca ccgcgagtcg 12480
aacctgggct ccatggtggc gctgaacgcc ttcctgagca cgcagcccgc caacgtgccc 12540
cggggccagg aggactacac caacttcatc agcgcgctgc ggctgatggt ggccgaggtg 12600
ccccagagcg aggtgtacca gtcggggccg gactacttct tccagaccag tcgccagggc 12660
ttgcagaccg tgaacctgag ccaggctttc aagaacttgc agggactgtg gggcgtgcag 12720
gccccggtcg gggaccgcgc gacggtgtcg agcctgctga cgccgaactc gcgcctgctg 12780
ctgctgctgg tggcgccctt cacggacagc ggcagcgtga gccgcgactc gtacctgggc 12840
tacctgctta acctgtaccg cgaggccatc gggcaggcgc acgtggacga gcagacctac 12900
caggagatca cccacgtgag ccgcgcgctg ggccaggagg acccgggcaa cctggaggcc 12960
accctgaact tcctgctgac caaccggtcg cagaagatcc cgccccagta cgcgctgagc 13020
accgaggagg agcgcatcct gcgctacgtg cagcagagcg tggggctgtt cctgatgcag 13080
gagggggcca cgcccagcgc cgcgctcgac atgaccgcgc gcaacatgga gcccagcatg 13140
tacgcccgca accgcccgtt catcaataag ctgatggact acttgcatcg ggcggccgcc 13200
atgaactcgg actactttac caacgccatc ttgaacccgc attggctccc gccgcccggg 13260
ttctacacgg gcgagtacga catgcccgac cccaacgacg ggttcctgtg ggacgacgtg 13320
gacagcagcg tgttctcgcc gcgccccacc gccaccaccg tgtggaagaa agagggcggg 13380
gaccggcggc cgtcctcggc gctgtccggt cgcgcgggtg ctgccgcggc ggtgcccgag 13440
gccgccagcc ccttcccgag cctgcccttt tcgctgaaca gcgtgcgcag cagcgagctg 13500
ggtcggctga cgcggccgcg cctgctgggc gaggaggagt acctgaacga ctccttgttg 13560
aggcccgagc gcgagaagaa cttccccaat aacgggatag agagcctggt ggacaagatg 13620
agccgctgga agacgtacgc gcacgagcac agggacgagc cccgagctag cagcagcgcc 13680
acccgtagac gccagcggca cgacaggcag cggggactgg tgtgggacga tgaggattcc 13740
gccgacgaca gcagcgtgtt ggacttgggt gggagtggtg gtaacccgtt cgctcacttg 13800
cgcccccgta tcgggcgcct gatgtaagaa tctgaaaaaa taaaaaacgg tactcaccaa 13860
ggccatggcg accagcgtgc gttcttctct gttgtttgta gtagtatgat gaggcgcgtg 13920
tacccggagg gtcctcctcc ctcgtacgag agcgtgatgc agcaggcggt ggcggcggcg 13980
atgcagcccc cgctggaggc gccttacgtg cccccgcggt acctggcgcc tacggagggg 14040
cggaacagca ttcgttactc ggagctggca cccttgtacg ataccacccg gttgtacctg 14100
gtggacaaca agtcggcgga catcgcctcg ctgaactacc agaacgacca cagcaacttc 14160
ctgaccaccg tggtgcagaa caacgatttc acccccacgg aggccagcac ccagaccatc 14220
aactttgacg agcgctcgcg gtggggcggc cagctgaaaa ccatcatgca caccaacatg 14280
cccaacgtga acgagttcat gtacagcaac aagttcaagg cgcgggtgat ggtctcgcgc 14340
aagaccccca acggggtgac ggtaggggat gattatgatg gtagtcagga cgagctgacc 14400
tacgagtggg tggagtttga gctgcccgag ggcaacttct cggtgaccat gaccatcgat 14460
ctgatgaaca acgccatcat cgacaactac ttggcggtgg ggcggcagaa cggggtgctg 14520
gagagcgaca tcggcgtgaa gttcgacacg cgcaacttcc ggctgggctg ggaccccgtg 14580
accgagctgg tgatgccggg cgtgtacacc aacgaggcct tccaccccga catcgtcctg 14640
ctgcccggct gcggcgtgga cttcaccgag agccgcctca gcaacctgct gggcatccgc 14700

```
aagcggcagc ccttccagga gggcttccag atcctgtacg aggacctgga ggggggcaac  14760
atccccgcgc tgctggacgt ggacgcctat gagaaaagca aggaggatag cgccgccgcg  14820
gcgaccgcag ccgtggccac cgcctctacc gaggtgcggg gcgataattt tactagcgcc  14880
gcagcagtgg ccgaggcggc tgaaaccgaa agtaagatag tgatccagcc ggtggagaag  14940
gacagcaagg acaggagcta caacgtgctc gcggacaaga aaaacaccgc ctaccgcagc  15000
tggtacctgg cctacaacta cggcgacccc gagaagggcg tgcgctcctg gacgctgctc  15060
accacctcgg acgtcacctg cggcgtggag caagtctact ggtcgctgcc cgacatgatg  15120
caagacccgg tcaccttccg ctccacgcgt caagttagca actacccggt ggtgggcgcc  15180
gagctcctgc ccgtctactc caagagcttc ttcaacgagc aggccgtcta ctcgcagcag  15240
ctgcgcgcct tcacctcgct cacgcacgtt ttcaaccgct tccccgagaa ccagatcctc  15300
gttcgcccgc ccgcgcccac cattaccacc gtcagtgaaa acgttcctgc tctcacagat  15360
cacgggaccc tgccgctgcg cagcagtatc cggggagtcc agcgcgtgac cgtcactgac  15420
gccagacgcc gcacctgccc ctacgtctac aaggccctgg gcgtagtcgc gccgcgcgtc  15480
ctctcgagcc gcaccttcta aaaaatgtcc attctcatct cgcccagtaa taacaccggt  15540
tggggcctgc gcgcgcccag caagatgtac ggaggcgctc gccaacgctc cacacaacac  15600
cccgtgcgcg tgcgcgggca cttccgcgct ccctggggcg ccctcaaggg ccgcgtgcgc  15660
tcgcgcacca ccgtcgacga cgtgatcgac caggtggtgg ccgacgcgcg caactacacg  15720
cccgccgccg cgcccgtctc caccgtggac gccgtcatcg acagcgtggt ggccgacgcg  15780
cgccggtacg cccgcgccaa gagccggcgg cggcgcatcg cccggcggca ccggagcacc  15840
cccgccatgc gcgcggcgcg agccttgctg cgcagggcca ggcgcacggg acgcagggcc  15900
atgctcaggg cggccagacg cgcggcctcc ggcagcagca gcgccggcag aacccgcaga  15960
cgcgcggcca cggcggcggc ggcggccatc gccagcatgt cccgcccgcg gcgcggcaac  16020
gtgtactggg tgcgcgacgc cgccaccggt gtgcgcgtgc ccgtgcgcac ccgccccccct  16080
cgcacttgaa gatgctgact tcgcgatgtt gatgtgtccc agcggcgagg aggatgtcca  16140
agcgcaaata caaggaagag atgctccagg tcatcgcgcc tgagatctac ggccccgcgg  16200
cggcggtgaa ggaggaaaga aagccccgca aactgaagcg ggtcaaaaag gacaaaaagg  16260
aggaggaaga tgacggactg gtggagtttg tgcgcgagtt cgccccccgg cggcgcgtgc  16320
agtggcgcgg gcggaaagtg aaaccggtgc tgcggcccgg caccacggtg gtcttcacgc  16380
ccggcgagcg ttccggctcc gcctccaagc gctcctacga cgaggtgtac ggggacgagg  16440
acatcctcga gcaggcggtc gagcgtctgg gcgagtttgc ttacggcaag cgcagccgcc  16500
ccgcgccctt gaaagaggag gcggtgtcca tcccgctgga ccacggcaac cccacgccga  16560
gcctgaagcc ggtgaccctg cagcaggtgc taccgagcgc ggcgccgcgc cggggcttca  16620
agcgcgaggg cggcgaggat ctgtacccga ccatgcagct gatggtgccc aagcgccaga  16680
agctggagga cgtgctggag cacatgaagg tggaccccga ggtgcagccc gaggtcaagg  16740
tgcggcccat caagcaggtg gctccgggcc tgggcgtgca gaccgtggac atcaagatcc  16800
ccacggagcc catggaaacg cagaccgagc ccgtgaagcc cagcaccagc accatggagg  16860
tgcagacgga tccctggatg ccagcggctt ccaccaccac cacccgccga agacgcaagt  16920
acggcgcgac cagcctgctg atgcccaact acgcgctgca tccttccatc atccccacgc  16980
cgggctaccg cggcacgcgc ttctaccgcg gctacagcag ccgccgcaag accaccaccc  17040
gccgccgccg tcgtcgcacc cgccgcagca gcaccgcgac ttccgccgcc gccttggtgc  17100
```

ggagagtgta ccgcagcggg cgcgagcctc tgaccctgcc gcgcgcgcgc taccacccga 17160
gcatcgccat ttaactctgc cgtcgcctcc ttgcagatat ggccctcaca tgccgcctcc 17220
gcgtccccat tacgggctac cgaggaagaa agccgcgccg tagaaggctg acggggaacg 17280
ggctgcgtcg ccatcaccac cggcggcggc gcgccatcag caagcggttg gggggaggct 17340
tcctgcccgc gctgatcccc atcatcgccg cggcgatcgg ggcgatcccc ggcatagctt 17400
ccgtggcggt gcaggcctct cagcgccact gagacacagc ttggaaaatt tgtaataaaa 17460
aatggactga cgctcctggt cctgtgatgt gtgtttttag atggaagaca tcaatttttc 17520
gtccctggca ccgcgacacg gcacgcggcc gtttatgggc acctggagcg acatcggcaa 17580
cagccaactg aacgggggcg ccttcaattg gagcagtctc tggagcgggc ttaagaattt 17640
cgggtccacg ctcaaaacct atggcaacaa ggcgtggaac agcagcacag ggcaggcgct 17700
gagggaaaag ctgaaagagc agaacttcca gcagaaggtg gtcgatggcc tggcctcggg 17760
catcaacggg gtggtggacc tggccaacca ggccgtgcag aaacagatca acagccgcct 17820
ggacgcggtc ccgcccgcgg ggtccgtgga gatgccccag gtggaggagg agctgcctcc 17880
cctggacaag cgcggcgaca agcgaccgcg tcccgacgcg gaggagacgc tgctgacgca 17940
cacggacgag ccgcccccgt acgaggaggc ggtgaaactg ggtctgccca ccacgcggcc 18000
cgtggcgcct ctggccaccg gggtgctgaa acccagcagc agcagcagcc agcccgcgac 18060
cctggacttg cctccgcctg cttcccgccc ctccacagtg gctaagcccc tgccgccggt 18120
ggccgtcgcg tcgcgcgccc cccgaggccg cccccaggcg aactggcaga gcactctgaa 18180
cagcatcgtg ggtctgggag tgcagagtgt gaagcgccgc cgctgctatt aaaagacact 18240
gtagcgctta acttgcttgt ctgtgtgtat atgtatgtcc gccgaccaga aggaggagga 18300
agaggcgcgt cgccgagttg caagatggcc accccatcga tgctgcccca gtgggcgtac 18360
atgcacatcg ccggacagga cgcttcggag tacctgagtc cgggtctggt gcagttcgcc 18420
cgcgccacag acacctactt cagtctgggg aacaagttta ggaaccccac ggtggcgccc 18480
acgcacgatg tgaccaccga ccgcagccag cggctgacgc tgcgcttcgt gcccgtggac 18540
cgcgaggaca acacctactc gtacaaagtg cgctacacgc tggccgtggg cgacaaccgc 18600
gtgctggaca tggccagcac ctactttgac atccgcggcg tgctggaccg gggccccagc 18660
ttcaaaccct actccggcac cgcctacaac agtctggctc ccaagggagc gcccaacacc 18720
tcacagtgga taaccaaaga caatggaact gataagacat acagttttgg aaatgctcca 18780
gtcagaggat tggacattac agaagagggt ctccaaatag gaaccgatga gtcagggggt 18840
gaaagcaaga aaatttttgc agacaaaacc tatcagcctg aacctcagct tggagatgag 18900
gaatggcatg atactattgg agctgaagac aagtatggag gcagagcgct taaacctgcc 18960
accaacatga aaccctgcta tgggtctttc gccaagccaa ctaatgctaa gggaggtcag 19020
gctaaaagca gaaccaagga cgatggcact actgagcctg atattgacat ggccttcttt 19080
gacgatcgca gtcagcaagc tagtttcagt ccagaacttg ttttgtatac tgagaatgtc 19140
gatctggaca ccccggatac ccacattatt tacaaacctg gcactgatga aacaagttct 19200
tctttcaact tgggtcagca gtccatgccc aacagaccca actacattgg gttcagagac 19260
aactttatcg gtctcatgta ctacaacagc actggcaata tgggtgtgct ggctggacag 19320
gcctcccagc tgaatgctgt ggtggacttg caggacagaa acactgaact gtcctaccag 19380
ctcttgcttg actctctggg tgacagaact aggtatttca gtatgtggaa tcaggcggtg 19440

```
gacagctacg accccgatgt gcgcattatt gaaaatcacg gtgtggagga tgaactcccc  19500
aactattgct tccctttgaa tggtgtgggc tttacagata cattccaggg aattaaggtt  19560
aaaactacca ataacggaac agcaaatgct acagagtggg aatctgatac ctctgtcaat  19620
aatgctaatg agattgccaa gggcaatcct ttcgccatgg agatcaacat ccaggccaac  19680
ctgtggcgga acttcctcta cgcgaacgtg gcgctgtacc tgcccgactc ctacaagtac  19740
acgccggcca acatcacgct gcccaccaac accaacacct acgattacat gaacggccgc  19800
gtggtggcgc cctcgctggt ggacgcctac atcaacatcg ggcgcgctg gtcgctggac  19860
cccatggaca acgtcaaccc cttcaaccac caccgcaacg cgggcctgcg ctaccgctcc  19920
atgctcctgg gcaacgggcg ctacgtgccc ttccacatcc aggtgcccca aaagtttttc  19980
gccatcaaga gcctcctgct cctgcccggg tcctacacct acgagtggaa cttccgcaag  20040
gacgtcaaca tgatcctgca gagctccctc ggcaacgacc tgcgcacgga cggggcctcc  20100
atcgccttca ccagcatcaa cctctacgcc accttcttcc ccatggcgca caacaccgcc  20160
tccacgctcg aggccatgct gcgcaacgac accaacgacc agtccttcaa cgactacctc  20220
tcggcggcca acatgctcta ccccatcccg gccaacgcca ccaacgtgcc catctccatc  20280
ccctcgcgca actgggccgc cttccgcgga tggtccttca cgcgcctcaa gacccgcgag  20340
acgccctcgc tcggctccgg gttcgacccc tacttcgtct actcgggctc catcccctac  20400
cttgacggca ccttctacct caaccacacc ttcaagaagg tctccatcac cttcgactcc  20460
tccgtcagct ggcccggcaa cgaccgcctc ctgacgccca acgagttcga aatcaagcgc  20520
accgtcgacg gagaggggta caacgtggcc cagtgcaaca tgaccaagga ctggttcctg  20580
gtccagatgc tggcccacta caacatcggc taccagggct tctacgtgcc cgagggctac  20640
aaggaccgca tgtactcctt cttccgcaac ttccagccca tgagccgcca ggtcgtggac  20700
gaggtcaact acaaggacta ccaggccgtc accctggcct accagcacaa caactcgggc  20760
ttcgtcggct acctcgcgcc caccatgcgc cagggccagc cctaccccgc caactacccc  20820
tacccgctca tcggcaagag cgccgtcgcc agcgtcaccc agaaaaagtt cctctgcgac  20880
cgggtcatgt ggcgcatccc cttctccagc aacttcatgt ccatgggcgc gctcaccgac  20940
ctcggccaga acatgctcta cgccaactcc gcccacgcgc tagacatgaa tttcgaagtc  21000
gaccccatgg atgagtccac ccttctctat gttgtcttcg aagtcttcga cgtcgtccga  21060
gtgcaccagc cccaccgcgg cgtcatcgag gccgtctacc tgcgcacgcc cttctcggcc  21120
ggcaacgcca ccacctaagc ctcttgcttc ttgcaagata tggcctgtgc gggctccggc  21180
gagcaggagc tcagggccat cctccgcgac ctgggctgcg ggccctgctt cctgggcacc  21240
ttcgacaagc gcttcccggg attcatggcc ccgcacaagc tggcctgcgc cattgtcaac  21300
acggccggcc gcgagaccgg gggcgagcac tggctggcct tcgcctggaa cccgcgctcc  21360
cacacctgct acctcttcga cccctttggg ttctcggacg agcgcctcaa gcagatctac  21420
cagttcgagt acgagggcct gctgcgtcgc agcgccctgg ccaccgagga ccgctgcgtc  21480
accctggaaa agtccaccca gaccgtgcag ggtccgcgct cggccgcctg cgggctcttc  21540
tgctgcatgt tcctgcacgc cttcgtgcac tggcccgacc gccccatgga caagaacccc  21600
accatgaact tgctgacggg ggtgcccaac ggcatgctcc agtcgcccca ggtggaaccc  21660
accctgcgcc gcaaccagga ggcgctctac cgcttcctca acgcccactc cgcctacttt  21720
cgatcccacc gcgcgcgcat cgagaaggcc accgccttcg accgcatgaa tcaagacatg  21780
taaaccgtgt gtgtatgtga atgctttatt cataataaac agcacatgtt tatgccacct  21840
```

tctctgaggc tctgacttta tttagaaatc gaaggggttc tgccggctct cggcgtgccc 21900
cgcgggcagg gatacgttgc ggaactggta cttgggcagc cacttgaact cggggatcag 21960
cagcttgggc acggggaggt cggggaacga gtcgctccac agcttgcgcg tgagttgcag 22020
ggcgcccagc aggtcgggcg cggagatctt gaaatcgcag ttgggacccg cgttctgcgc 22080
gcgagagttg cggtacacgg ggttgcagca ctggaacacc atcagggccg ggtgcttcac 22140
gctcgccagc accgtcgcgt cggtgatgcc ctccacgtcc agatcctcgg cgttggccat 22200
cccgaagggg gtcatcttgc aggtctgccg ccccatgctg ggcacgcagc cgggcttgtg 22260
gttgcaatcg cagtgcaggg ggatcagcat catctgggcc tgctcggagc tcatgcccgg 22320
gtacatggcc ttcatgaaag cctccagctg gcggaaggcc tgctgcgcct tgccgccctc 22380
ggtgaagaag accccgcagg acttgctaga gaactggttg gtggcgcagc cggcgtcgtg 22440
cacgcagcag cgcgcgtcgt tgttggccag ctgcaccacg ctgcgccccc agcggttctg 22500
ggtgatcttg gcccggtcgg ggttctcctt cagcgcgcgc tgcccgttct cgctcgccac 22560
atccatctcg atcgtgtgct ccttctggat catcacggtc ccgtgcaggc accgcagctt 22620
gccctcggcc tcggtgcagc cgtgcagcca cagcgcgcag ccggtgctct cccagttctt 22680
gtgggcgatc tgggagtgcg agtgcacgaa gccctgcagg aagcggccca tcatcgcggt 22740
cagggtcttg ttgctggtga aggtcagcgg gatgccgcgg tgctcctcgt tcacatacag 22800
gtggcagatg cggcggtaca cctcgccctg ctcgggcatc agctggaagg cggacttcag 22860
gtcgctctcc acgcggtacc ggtccatcag cagcgtcatc acttccatgc ccttctccca 22920
ggccgaaacg atcggcaggc tcaggggttt cttcaccgcc attgtcatct tagtcgccgc 22980
cgccgaagtc agggggtcgt tctcgtccag ggtctcaaac actcgcttgc cgtccttctc 23040
ggtgatgcgc acggggggga aggcgaagcc cacggccgcc agctcctcct cggcctgcct 23100
ttcgtcctcg ctgtcctggc tgatgtcttg caaaggcaca tgcttggtct tgcggggttt 23160
ctttttgggc ggcagaggcg gcggcggaga cgtgctgggc gagcgcgagt tctcgctcac 23220
cacgactatt tcttctcctt ggccgtcgtc cgagaccacg cggcggtagg catgcctctt 23280
ctggggcaga ggcggaggcg acgggctctc gcggttcggc gggcggctgg cagagcccct 23340
tccgcgttcg gggtgcgct cctggcggcg ctgctctgac tgacttcctc cgcggccggc 23400
cattgtgttc tcctagggag caagcatgga gactcagcca tcgtcgccaa catcgccatc 23460
tgcccccgcc gccgccgacg agaaccagca gaatgaaagc ttaaccgccc cgccgcccag 23520
ccccacctcc gacgcggccc cagacatgca agagatggag gaatccatcg agattgacct 23580
gggctacgtg acgcccgcgg agcacgagga ggagctggca gcgcgctttt cagccccgga 23640
agagaaccac caagagcagc cagagcagga agcagagagc gagcagcagc aggctgggct 23700
cgagcatggc gactacctga gcggggcaga ggacgtgctc atcaagcatc tggcccgcca 23760
atgcatcatc gtcaaggacg cgctgctcga ccgcgccgag gtgcccctca gcgtggcgga 23820
gctcagccgc gcctacgagc gcaacctctt ctcgccgcgc gtgcccccca agcgccagcc 23880
caacggcacc tgcgagccca acccgcgcct caacttctac ccggtcttcg cggtgcccga 23940
ggccctggcc acctaccacc tctttttcaa gaaccaaagg atccccgtct cctgccgcgc 24000
caaccgcacc cgcgccgacg ccctgctcaa cctgggcccc ggcgcccgcc tacctgatat 24060
cgcctccttg gaagaggttc ccaagatctt cgagggtctg ggcagcgacg agactcgggc 24120
cgcgaacgct ctgcaaggaa gcggagagga gcatgagcac cacagcgccc tggtggagtt 24180

```
ggaaggcgac aacgcgcgcc tggcggtgct caagcgcacg gtcgagctga cccacttcgc  24240
ctacccggcg ctcaacctgc cccccaaggt catgagcgcc gtcatggacc aggtgctcat  24300
caagcgcgcc tcgcccctct cggaggagga gatgcaggac cccgagagct cggacgaggg  24360
caagcccgtg gtcagcgacg agcagctggc gcgctggctg ggagcgagta gcacccccca  24420
gagcctggaa gagcggcgca agctcatgat ggccgtggtc ctggtgaccg tggagctgga  24480
gtgtctgcgc cgcttcttcg ccgacgcgga gaccctgcgc aaggtcgagg agaacctgca  24540
ctacctcttc aggcacgggt tcgtgcgcca ggcctgcaag atctccaacg tggagctgac  24600
caacctggtc tcctacatgg gcatcctgca cgagaaccgc ctggggcaga acgtgctgca  24660
caccaccctg cgcggggagg cccgccgcga ctacatccgc gactgcgtct acctgtacct  24720
ctgccacacc tggcagacgg gcatgggcgt gtggcagcag tgcctggagg agcagaacct  24780
gaaagagctc tgcaagctcc tgcagaagaa cctcaaggcc ctgtggaccg ggttcgacga  24840
gcgcaccacc gcctcggacc tggccgacct catcttcccc gagcgcctgc ggctgacgct  24900
gcgcaacggg ctgcccgact ttatgagcca aagcatgttg caaaactttc gctctttcat  24960
cctcgaacgc tccgggatcc tgcccgccac ctgctccgcg ctgccctcgg acttcgtgcc  25020
gctgaccttc cgcgagtgcc ccccgccgct ctggagccac tgctacctgc tgcgcctggc  25080
caactacctg gcctaccact cggacgtgat cgaggacgtc agcggcgagg gcctgctcga  25140
gtgccactgc cgctgcaacc tctgcacgcc gcaccgctcc ctggcctgca acccccagct  25200
gctgagcgag acccagatca tcggcacctt cgagttgcaa ggcccccggcg acagcgaggg  25260
caaggggggt ctcaaactca ccccggggct gtggacctcg gcctacttgc gcaagttcgt  25320
gcccgaggac taccatccct tcgagatcag gttctacgag gaccaatccc agccgcccaa  25380
ggccaagctg tcggcctgcg tcatcaccca gggggccatc ctggcccaat tgcaagccat  25440
ccagaaatcc cgccaagaat ttctgctgaa aaagggccac ggggtctact tggaccccca  25500
gaccggagag gagctcaacc ccagcttccc ccaggatgcc ccgaggaagc agcaagaagc  25560
tgaaagtgga gctgccgccg ccggaggatt tggaggaaga ctgggagagc agtcaggcag  25620
aggagatgga agactgggac agcactcagg cagaggagga cagcctgcaa gacagtctgg  25680
aggaggaaga cgaggtggag gaggaggcag aggaagaagc agccgccgcc agaccgtcgt  25740
cctcggcgga ggagaaagca agcagcacgg ataccatctc cgctccgggt cggggtcgcg  25800
gcggccgggc ccacagtagg tgggacgaga ccgggcgctt cccgaacccc accacccaga  25860
ccggtaagaa ggagcggcag ggatacaagt cctggcgggg gcacaaaaac gccatcgtct  25920
cctgcttgca agcctgcggg ggcaacatct ccttcacccg gcgctacctg ctcttccacc  25980
gcggggtgaa cttccccccgc aacatcttgc attactaccg tcacctccac agcccctact  26040
actgtttcca agaagaggca gaaacccagc agcagcagca gaaaaccagc gacagctaga  26100
aaatccacag cggcggcggc aggtggactg aggatcgcgg cgaacgagcc agcgcagacc  26160
cgggagctga ggaaccggat ctttcccacc ctctatgcca tcttccagca gagtcggggg  26220
caggagcagg aactgaaagt caagaaccgt tctctgcgct cgctcacccg cagttgtctg  26280
tatcacaaga gcgaagacca acttcagcgc actctcgagg acgccgaggc tctcttcaac  26340
aagtactgcg cgctcactct taaagagtag cccgcgcccg cccacacacg gaaaaaggcg  26400
ggaattacgt caccacctgc gcccttcgcc cgaccatcat gagcaaagag attcccacgc  26460
cttacatgtg gagctaccag ccccagatgg gcctggccgc cggcgccgcc caggactact  26520
ccacccgcat gaactggctc agtgccgggc ccgcgatgat ctcacgggtg aatgacatcc  26580
```

```
gcgcccaccg aaaccagata ctcctagaac agtcagcgat caccaccacg ccccgccatc  26640
accttaatcc gcgtaattgg cccgccgccc tggtgtacca ggaaattccc cagcccacga  26700
ccgtactact tccgcgagac gcccaggccg aagtccagct gactaactca ggtgtccagc  26760
tggccggcgg cgccgccctg tgtcgtcacc gccccgctca gggtataaag cggctggtga  26820
tccgaggcag aggcacacag ctcaacgacg aggtggtgag ctcttcgctg ggtctgcgac  26880
ctgacggagt cttccaactc gccggatcgg ggagatcttc cttcacgcct cgtcaggccg  26940
tcctgacttt ggagagttcg tcctcgcagc cccgctcggg cggcatcggc actctccagt  27000
tcgtggagga gttcactccc tcggtctact tcaacccctt ctccggctcc cccggccact  27060
acccggacga gttcatcccg aacttcgacg ccatcagcga gtcggtggac ggctacgatt  27120
gaatgtccca tggtggcgca gctgacctag ctcggcttcg acacctggac cactgccgcc  27180
gcttccgctg cttcgctcgg gatctcgccg agtttgccta ctttgagctg cccgaggagc  27240
accctcaggg cccggcccac ggagtgcgga tcgtcgtcga agggggcctc gactcccacc  27300
tgcttcggat cttcagccag cgaccgatcc tggtcgagcg cgagcaagga cagacccgtc  27360
tgaccctgta ctgcatctgc aaccaccccg gcctgcatga aagtctttgt tgtctgctgt  27420
gtactgagta taataaaagc tgagatcagc gactactccg gacttccgtg tgttcctgaa  27480
tccatcaacc agtctttgtt cttcaccggg aacgagaccg agctccagct ccagtgtaag  27540
ccccacaaga agtacctcac ctggctgttc cagggctctc cgatcgccgt tgtcaaccac  27600
tgcgacaacg acggagtcct gctgagcggc cctgccaacc ttactttttc cacccgcaga  27660
agcaagctcc agctcttcca acccttcctc cccgggacct atcagtgcgt ctcgggaccc  27720
tgccatcaca ccttccacct gatcccgaat accacagcgg cgctccccgc tactaacaac  27780
caaactaccc accaacgaca ccgtcgcgac ctttcctctg ggtctaatac cactaccgga  27840
ggtgagctcc gaggtcaacc aacctctggg atttactacg gcccctggga ggtggtaggg  27900
ttaatagcgc taggcctagt tgcgggtggg cttttggctc tctgctacct atacctccct  27960
tgctgttcgt acttagtggt gctgtgttgc tggtttaaga aatggggaag atcaccctag  28020
tgagctgcgg tgcgctggtg gcggtggtgc tttcgattgt gggactgggc agcgcggctg  28080
tagtgaagga gaaggccgat ccctgcttgc atttcaatcc cgacaaatgc cagctgagtt  28140
ttcagcccga tggcaatcgg tgcgcggtgc tgatcaagtg cggatgggaa tgcgagaacg  28200
tgagaatcga gtacaataac aagactcgga acaatactct cgcgtccgtg tggcagcccg  28260
gggaccccga gtggtacacc gtctctgtcc ccggtgctga cggctccccg cgcaccgtga  28320
ataatacttt catttttgcg cacatgtgcg acacggtcat gtggatgagc aagcagtacg  28380
atatgtggcc ccccacgaag gagaacatcg tggtcttctc catcgcttac agcgtgtgca  28440
cggtgctaat caccgctatc gtgtgcctga gcattcacat gctcatcgct attcgcccca  28500
gaaataatgc cgaaaaagag aaacagccat aacacgtttt ttcacacacc tttttcagac  28560
catggcctct gttactgccc tatttatttt tttgggcctt gtgggcacta gcagcacttt  28620
tgatcataaa aacctaactg tttttgttgg ttctgatgtt acactacctg ggcatcaatc  28680
gcaccagagg gtttcatggt atcattttaa taaacagaac acagcttata cactttgcaa  28740
aggttatcag caagccacat atcgcagtgg tctttattac agatgcaata acaataacct  28800
cacactactc tcagttaatg caaattattc tggcacatac tatggaacca attttaacgc  28860
aaaacaggac acttactata gtgtcaaagt attgaatcca acctctccta gaactaccac  28920
```

```
taagcctacc accaccacta ctactgcgaa acccactaca cctaaaacta ccaagaaaac  28980
cactgtgaaa actacaacaa ctaggaccac cacaactaca gaggctacca ccagcacaac  29040
acttgctacc actacacaca cacacactga gctaacctta cagaccacta atgatttgat  29100
cgccctgttg caaaaggggg ataacagcac cacttccaat gaggagatac ccaaatccat  29160
gattggcatt attgttgctg tagtggtgtg catgttgatc atcgccttgt gcatggtgta  29220
ctatgccttc tgctacagaa agcacagact gaacgacaag ctggaacact tactaagtgt  29280
tgaattttaa tttttagaa ccatgaagat cctaggcctt ttagtttttt ctatcattac  29340
ctctgctcta tgcaattctg acaatgagga cgttactgtc gttgtcggat caaattatac  29400
actaaaaggt ccagcaaaag gtatgctttc gtggtattgt tggttcggaa ctgacgagca  29460
acagacagaa ctttgcaatg ctcaaaaagg caaaacctca aattctaaaa tctctaatta  29520
tcaatgcaat ggcactgact tagtattgct caatgtcacg aaagcatatg ctggcagtta  29580
cacctgccct ggagatgatg ccgacaatat gatttttac aaagtggaag tggttgatcc  29640
cactactcca ccgcccacca ccacaactac tcataccaca cacacagaac aaacaccaga  29700
ggcagcagaa gcagagttgg ccttccaggt tcacggagat tcctttgctg tcaatacccc  29760
tacacccgat cagcggtgtc cggggctgct cgtcagcggc attgtcggtg tgctttcggg  29820
attagcagtt ataatcatct gcatgttcat ttttgcttgc tgctatagaa ggctttaccg  29880
acaaaaatca gacccactgc tgaacctcta tgtttaattt tttccagagc catgaaggca  29940
gttagcactc tagtttttg ttctttgatt ggcattgttt tttgcaatcc tattcctaga  30000
gttagcttta ttaaagatgt gaatgttact gagggggca atgtgacact ggtaggtgta  30060
gagggtgctg aaaacaccac ctggacaaaa taccacctca atgggtggaa agatatttgc  30120
aattggagtg tattagttta tacatgtgag ggagttaatc ttaccattgt caatgccacc  30180
tcagctcaaa atggtagaat tcaaggacaa agtgtcagtg tatctaatgg gtattttacc  30240
caacatactt ttatctatga cgttaaagtc ataccactgc ctacgcctag cccacctagc  30300
actaccacac agacaaccac atacagtaca tcaaatcagc ctaccaccac tacagcagca  30360
gaggttgcca gctcgtctgg ggtccgagtg gcatttttga tgttggcccc atctagcagt  30420
cccactgcta gtaccaatga gcagactact gaatttttgt ccactgtcga gagccacacc  30480
acagctacct cgagtgcctt ctctagcacc gccaatctct cctcgctttc ctctacacca  30540
atcagtcccg ctactactcc tagccccgct cctcttccca ctcccctgaa gcaaactgag  30600
gacagcggca tgcaatggca gatcaccctg ctcattgtga tcgggttggt catcctggcc  30660
gtgttgctct actacatctt ctgccgccgc attcccaacg cgcaccgcaa gccggcctac  30720
aagcccatcg ttatcgggca gccggagccg cttcaggtgg aagggggtct aaggaatctt  30780
ctcttctctt ttacagtatg gtgattgaac tatgattcct agacaattct tgatcactat  30840
tcttatctgc ctcctccaag tctgtgccac cctcgctctg gtggccaacg ccagtccaga  30900
ctgtattggg cccttcgcct cctacgtgct ctttgccttc atcacctgca tctgctgctg  30960
tagcatagtc tgcctgctta tcaccttctt ccagttcatt gactggatct ttgtgcgcat  31020
cgcctacctg cgccaccacc cccagtaccg cgaccagcga gtggcgcggc tgctcaggct  31080
cctctgataa gcatgcgggc tctgctactt ctcgcgcttc tgctgttagt gctcccccgt  31140
cccgtcgacc cccggtcccc cactcagtcc cccgaggagg tccgcaaatg caaattccaa  31200
gaaccctgga aattcctcaa atgctaccgc caaaaatcag acatgcatcc cagctggatc  31260
atgatcattg ggatcgtgaa cattctggcc tgcaccctca tctcctttgt gatttacccc  31320
```

tgctttgact ttggttggaa ctcgccagag gcgctctatc tcccgcctga acctgacaca 31380
ccaccacagc agcaacctca ggcacacgca ctaccaccac cacagcctag gccacaatac 31440
atgcccatat tagactatga ggccgagcca cagcgaccca tgctccccgc tattagttac 31500
ttcaatctaa ccggcggaga tgactgaccc actggccaac aacaacgtca acgaccttct 31560
cctggacatg gacggccgcg cctcggagca gcgactcgcc caacttcgca ttcgccagca 31620
gcaggagaga gccgtcaagg agctgcagga cggcatagcc atccaccagt gcaagaaagg 31680
catcttctgc ctggtgaaac aggccaagat ctcctacgag gtcacccaga ccgaccatcg 31740
cctctcctac gagctcctgc agcagcgcca gaagttcacc tgcctggtcg gagtcaaccc 31800
catcgtcatc acccagcagt cgggcgatac caaggggtgc atccactgct cctgcgactc 31860
ccccgactgc gtccacactc tgatcaagac cctctgcggc ctccgcgacc tcctccccat 31920
gaactaatca ccccccttatc cagtgaaata aagatcatat tgatgatgat ttaaataaaa 31980
aaaaaaaaaa aataatcatt tgatttgaaa taaagataca atcatattga tgatttgagt 32040
tttaaaaaaa taaagaatca cttacttgaa atctgatacc aggtctctgt ccatgttttc 32100
tgccaacacc acttcactcc cctcttccca gctctggtac tgcaggcccc ggcgggctgc 32160
aaacttcctc cacacgctga aggggatgtc aaattcctcc tgtccctcaa tcttcatttt 32220
atcttctatc agatgtccaa aaagcgcgtc cgggtggatg atgacttcga ccccgtctac 32280
ccctacgatg cagacaacgc accgaccgtg cccttcatca acccccccctt cgtctcttca 32340
gatggattcc aagagaagcc cctgggggtg ctgtccctgc gactggccga ccccgtcacc 32400
accaagaacg gggaaatcac cctcaagctg ggagaggggg tggacctcga ctcctcggga 32460
aaactcatct ccaacacggc caccaaggcc gccgcccctc tcagtttttc caacaaattt 32520
cccttaacat ggatacccct ttttacacca aagatggaaa attaaccatg caggtcactg 32580
caccgctaaa gttagcaaac acagccatat tgaacacact agccatggca tatggaaatg 32640
gattagggct aagcaacaac gctcttaccg ttcagttaca atctccactc acctttaaca 32700
acagcaaggt tgctatcaac ctggaaaatg gaccactaaa cgtgacatca aatagactta 32760
gcattaattg caagaggggt gtctatgtca ccaccacagg agatgcaatc gaaaccaaca 32820
taagttggcc aaatgctatt aaatttatag gaaatgcaat gggtgtcaat attgatacaa 32880
acaaaggctt gcaatttggc accaccagca ctgtcacaga tgtgaccgat gctttcccca 32940
tacaagtcaa acttggggct ggtcttgcat ttgatagcac tggagctatt gttgcatgga 33000
acaaagagga tgacagtctc actttgtgga ctacaccaga tccatctcca aattgcaaga 33060
tagcatctga caaagatgct aaactcacac tttgcttgac aaagtgtgga agtcaaattc 33120
tgggtactgt gactgtattg gcagtgaata atggaagtct caacccaatc acaaacacag 33180
taagcactgc ccttgtatca cttaaattcg acgccaatgg agcactcttg gaaaaatcaa 33240
ccctaaacag agaatattgg aactacagac aaggagatct cattccaggt acaccatata 33300
cccatgcagt aggtttcatg cccaacaaga aagcctaccc taaaaacaca actgcagctt 33360
ccaaaagcca cattgtgggg gacgtctatc tagacgggga tgtagataag cccctatctc 33420
tcataatcac ttttaatgaa actgatgatg aatcatgtga ctattgcatg aactttcaat 33480
ggaaatgggg tgctgatcaa tacaaggaca aaacactcgc taccagctcc ttcaccttct 33540
cctacatcgc ccaagaatga acactgtatc ccaccctgca tgccaaccct tcccacccca 33600
ctctgtctgt ggaaaaaact ctgaaacaca aaataaaata aagttcaagt gttttattga 33660
ttcaacagtt ttacaggatt cgagcagtta tttttcctcc accctcccag gacatggaat 33720
acaccaccct ctccccccgc acagccttga acatctgaat gccattggtg atggacatgc 33780
ttttggtctc cacgttccac acagtttcag agcgagccag tctcgggtcg gtcagggaga 33840
tgaaaccctc cgggcactcc cgcatctgca cctcacagct caacagctga ggattgtcct 33900
cggtggtcgg gatcacggtt atctggaaga agcagaagag cggcggtggg aatcatagtc 33960
cgcgaacggg atcggccggt ggtgccgcat caggccccgc agcagtcgct gccgccgccg 34020
ctccgtcaag ctgctgctca gggggtccgg gtccagggac tccctcagca tgatgcccac 34080
ggccctcagc atcagtcgtc tggtgcggcg ggcgcagcag cgcatgcgga tctcgctcag 34140
gtcgctgcag tacgtgcaac acaggaccac caggttgttc aacagtccat agttcaacac 34200
gctccagccg aaactcatcg cgggaaggat gctacccacg tggccgtcgt accagatcct 34260
caggtaaatc aagtggcgcc ccctccagaa cacgctgccc acgtacatga tctccttggg 34320
catgtggcgg ttcaccacct cccggtacca catcaccctt tggttgaaca tgcagccccg 34380
gatgatcctg cggaaccaca gggccagcac cgccccgccc gccatgcagc gaagagaccc 34440
cgggtcccga caatggcaat ggaggaccca ccgctcgtac ccgtggatca tctgggagct 34500
gaacaagtct atgttggcac agcacaggca cacgctcatg catctcttca gcactctcag 34560
ctcctcgggg gtcaaaacca tatcccaggg cacggggaac tcttgcagga cagcgaaccc 34620
cgcagaacag ggcaatcctc gcacataact tacattgtgc atggacaggg tatcgcaatc 34680
aggcagcacc gggtgatcct ccaccagaga agcgcgggtc tcggtctcct cacagcgtgg 34740
taagggggcc ggccgatacg ggtgatggcg ggacgcggct gatcgtgttc gcgaccgtgt 34800
catgatgcag ttgctttcgg acattttcgt acttgctgta gcagaacctg gtccgggcgc 34860
tgcacaccga tcgccggcgg cggtctcggc gcttggaacg ctcggtgttg aaattgtaaa 34920
acagccactc tctcagaccg tgcagcagat ctagggcctc aggagtgatg aagatcccat 34980
catgcctgat ggctctgatc acatcgacca ccgtggaatg ggccagaccc agccagatga 35040
tgcaattttg ttgggtttcg gtgacggcgg gggagggaag aacaggaaga accatgatta 35100
acttttaatc caaacggtct cggagtactt caaaatgaag atcgcggaga tggcacctct 35160
cgcccccgct gtgttggtgg aaaataacag ccaggtcaaa ggtgatacgg ttctcgagat 35220
gttccacggt ggcttccagc aaagcctcca cgcgcacatc cagaaacaag acaatagcga 35280
aagcgggagg gttctctaat tcctcaatca tcatgttaca ctcctgcacc atccccagat 35340
aattttcatt tttccagcct tgaatgattc gaactagttc ctgaggtaaa tccaagccag 35400
tcatgataaa gagctcgcgc agagcgccct ccaccggcat tcttaagcac accctcataa 35460
ttccaagata ttctgctcct ggttcacctg cagcagattg acaagcggaa tatcaaaatc 35520
tctgccgcga tccctgagct cctccctcag caataactgt aagtactctt tcatatcctc 35580
tccgaaattt ttagccatag gaccaccagg aataagatta gggcaagcca cagtacagat 35640
aaaccgaagt cctccccagt gagcattgcc aaatgcaaga ctgctataag catgctggct 35700
agacccggtg atatcttcca gataactgga cagaaaatca cccaggcaat ttttaagaaa 35760
atcaacaaaa gaaaaatcct ccaggtgcac gtttagggcc tcgggaacaa cgatggagta 35820
aacgcaagcg gtgcgttcca gcatggttag ttagctgatc tgtaaaaaaa caaaaaataa 35880
aacattaaac catgctagcc tggcgaacag gtgggtaaat cgttctctcc agcaccaggc 35940
aggccacggg gtctccggcg cgaccctcgt aaaaattgtc gctatgattg aaaaccatca 36000
cagagagacg ttcccggtgg ccggcgtgaa tgattcgaca agatgaatac acccccggaa 36060

```
cattggcgtc cgcgagtgaa aaaaagcgcc cgaggaagca ataaggcact acaatgctca  36120
gtctcaagtc cagcaaagcg atgccatgcg gatgaagcac aaaattctca ggtgcgtaca  36180
aaatgtaatt actcccctcc tgcacaggca gcaaagcccc cgatccctcc aggtacacat  36240
acaaagcctc agcgtccata gcttaccgag cagcagcaca caacaggcgc aagagtcaga  36300
gaaaggctga gctctaacct gtccacccgc tctctgctca atatatagcc cagatctaca  36360
ctgacgtaaa ggccaaagtc taaaaatacc cgccaaataa tcacacacgc ccaacacacg  36420
cccagaaacc ggtgacacac tcagaaaaat acgcgcactt cctcaaacgc ccaaactgcc  36480
gtcatttccg ggttcccacg ctacgtcatc agaattcgac tttcaaattc cgtcgaccgt  36540
taaaaacgtc acccgccccg cccctaacgg tcgcccgtct ctcggccaat cacagccccg  36600
catccccaaa ttcaaacacc tcatttgcat attaacgcgc accaaaagtt tgaggtatat  36660
tattgatgat gttaattaat tggttc                                       36686
```

```
<210> SEQ ID NO 2
<211> LENGTH: 40224
<212> TYPE: DNA
<213> ORGANISM: Artificial Sequence
<220> FEATURE:
<223> OTHER INFORMATION: Synthesized

<400> SEQUENCE: 2
```

```
ttaattaatt ggttccactg agcgtcagac cccttaataa gatgatcttc ttgagatcgt     60
tttggtctgc gcgtaatctc ttgctctgaa aacgaaaaaa ccgccttgca gggcggtttt    120
tcgaaggttc tctgagctac caactctttg aaccgaggta actggcttgg aggagcgcag    180
tcaccaaaac ttgtcctttc agtttagcct taaccggcgc atgacttcaa gactaactcc    240
tctaaatcaa ttaccagtgg ctgctgccag tggtgctttt gcatgtcttt ccgggttgga    300
ctcaagacga tagttaccgg ataaggcgca gcggtcggac tgaacggggg gttcgtgcat    360
acagtccagc ttggagcgaa ctgcctaccc ggaactgagt gtcaggcgtg gaatgagaca    420
aacgcggcca taacagcgga atgacaccgg taaaccgaaa ggcaggaaca ggagagcgca    480
cgagggagcc gccaggggga aacgcctggt atctttatag tcctgtcggg tttcgccacc    540
actgatttga gcgtcagatt tcgtgatgct tgtcaggggg gcggagccta tggaaaaacg    600
gctttgccgc ggccctctca cttccctgtt aagtatcttc ctggcatctt ccaggaaatc    660
tccgccccgt tcgtaagcca tttccgctcg ccgcagtcga acgaccgagc gtagcgagtc    720
agtgagcgag gaagcggaat atatcctgta tcacatattc tgctgacgca ccggtgcagc    780
ctttttctc ctgccacatg aagcacttca ctgacaccct catcagtgcc aacatagtaa    840
gccagtatac actccgctag cgctgaggtc tgcctcgtga agaaggtgtt gctgactcat    900
accaggcctg aatcgcccca tcatccagcc agaaagtgag ggagccacgg ttgatgagag    960
ctttgttgta ggtggaccag ttggtgattt tgaacttttg ctttgccacg gaacggtctg   1020
cgttgtcggg aagatgcgtg atctgatcct tcaactcagc aaaagttcga tttattcaac   1080
aaagccacgt tgtgtctcaa aatctctgat gttacattgc acaagataaa aatatatcat   1140
catgaacaat aaaactgtct gcttacataa acagtaatac aaggggtgtt atgagccata   1200
ttcaacggga aacgtcttgc tcgaggccgc gattaaattc caacatggat gctgatttat   1260
atgggtataa atgggctcgc gataatgtcg ggcaatcagg tgcgacaatc tatcgattgt   1320
atgggaagcc cgatgcgcca gagttgtttc tgaaacatgg caaaggtagc gttgccaatg   1380
```

-continued

```
atgttacaga tgagatggtc agactaaact ggctgacgga atttatgcct cttccgacca   1440
tcaagcattt tatccgtact cctgatgatg catggttact caccactgcg atccccggga   1500
aaacagcatt ccaggtatta gaagaatatc ctgattcagg tgaaaatatt gctgatgcgc   1560
tggcagtgtt cctgcgccgg ttgcattcga ttcctgtttg taattgtcct tttaacagcg   1620
atcgcgtatt tcgtctcgct caggcgcaat cacgaatgaa taacggtttg gttgatgcga   1680
gtgattttga tgacgagcgt aatggctggc ctgttgaaca agtctggaaa gaaatgcata   1740
agcttttgcc attctcaccg gattcagtcg tcactcatgg tgatttctca cttgataacc   1800
ttatttttga cgaggggaaa ttaataggtt gtattgatgt tggacgagtc ggaatcgcag   1860
accgatacca ggatcttgcc atcctatgga actgcctcgg tgagttttct ccttcattac   1920
agaaacggct ttttcaaaaa tatggtattg ataatcctga tatgaataaa ttgcagtttc   1980
atttgatgct cgatgagttt ttctaatcag aattggttaa ttggttgtaa cactggcaga   2040
gcattacgct gacttgacgg gacggcttag ggttaggcgt tttgcgctgc ttcgcgatgt   2100
acgggccaga tatacgcaat gtagtcttat gcaatactct tgtagtcttg caacatggta   2160
acgatgagtt agcaacatgc cttacaagga gagaaaaagc accgtgcatg ccgattggtg   2220
gaagtaaggt ggtacgatcg tgccttatta ggaaggcaac agacgggtct gacatggatt   2280
ggacgaacca ctgaattgcc gcattgcaga gatattgtat ttaagtgcct agctcgatac   2340
ataaacctct ggctaactag agaacccact gcttactggc ttatcgaaat taatacgact   2400
cactataggg agacccagcc accatggtga gcaagggcga ggagctgttc accggggtgg   2460
tgcccatcct ggtcgagctg gacggcgacg taaacggcca caagttcagc gtgtccggcg   2520
agggcgaggg cgatgccacc tacggcaagc tgaccctgaa gttcatctgc accaccggca   2580
agctgcccgt gccctggccc accctcgtga ccaccctgac ctacggcgtg cagtgcttca   2640
gccgctaccc cgaccacatg aagcagcacg acttcttcaa gtccgccatg cccgaaggct   2700
acgtccagga gcgcaccatc ttcttcaagg acgacggcaa ctacaagacc cgcgccgagg   2760
tgaagttcga gggcgacacc ctggtgaacc gcatcgagct gaagggcatc gacttcaagg   2820
aggacggcaa catcctgggg cacaagctgg agtacaacta caacagccac aacgtctata   2880
tcatggccga caagcagaag aacggcatca aggtgaactt caagatccgc cacaacatcg   2940
aggacggcag cgtgcagctc gccgaccact accagcagaa cacccccatc ggcgacggcc   3000
ccgtgctgct gcccgacaac cactacctga gcacccagtc cgccctgagc aaagacccca   3060
acgagaagcg cgatcacatg gtcctgctgg agttcgtgac cgccgccggg atcactctcg   3120
gcatggacga gctgtacaag taaagcggcc gctcgagtct agagggcccg tttaaacccg   3180
ctgatcagcc tcgactgtgc cttctagttg ccagccatct gttgtttgcc cctcccccgt   3240
gccttccttg accctggaag gtgccactcc cactgtcctt tcctaataaa atgaggaaat   3300
tgcatcgcat tgtctgagta ggtgtcattc tattctgggg ggtggggtgg ggcaggacag   3360
caagggggag gattgggaag acaatagcag gcatgctggg gatgcggtgg gctctatggc   3420
ttctgaggcg gaaagaacca gctggggctc tagggggtat ccccacgcgc cctgtagcgg   3480
cgcattaata gggataacag ggtaatatac aaacgaggcc ctttcgtctt taattaacat   3540
catcaataat atacctcaaa cttttggtgc gcgttaatat gcaaatgagg tgtttgaatt   3600
tggggatgcg gggctgtgat tggccgagag acgggcgacc gttaggggcg gggcgggtga   3660
cgttttgatg acgtggccgt gaggcggagc cggtttgcaa gttctcgtgg gaaaagtgac   3720
gtcaaacgag gtgtggtttg aacacggaaa tactcaattt tcccgcgctc tctgacagga   3780
```

-continued

```
aatgaggtgt ttctgggcgg atgcaagtga aaacgggcca ttttcgcgcg aaaactgaat   3840
gaggaagtga aaatctgagt aatttcgcgt ttatggcagg gaggagtatt tgccgagggc   3900
cgagtagact ttgaccgatt acgtggggt ttcgattacc gtatttttca cctaaatttc   3960
cgcgtacggt gtcaaagtcc ggtgttttta cgtaggtgtc agctgatcgc cagggtattt   4020
aaacctgcgc tctctagtca agaggccact cttgagtgcc agcgagtaga gttttctcct   4080
ccgcgccgcg agtcagatct acactttgaa agatgaggca cctgagagac ctgcccggta   4140
atgttttcct ggctactggg aacgagattc tggaactggt ggtggacgcc atgatgggtg   4200
acgaccctcc tgagccccct accccatttg aggcgccttc gctgtacgat ttgtatgatc   4260
tggaggtgga tgtgcccgag aacgaccccca acgaggaggc ggtgaatgat ttgtttagcg   4320
atgccgcgct gctggctgcc gagcaggcta atacggactc tggctcagac agcgattcct   4380
ctctccatac cccgagaccc ggcagaggtg agaaaaagat ccccgagctt aaaggggaag   4440
agctcgacct gcgctgctat gaggaatgct tgcctccgag cgatgatgag gaggacgagg   4500
aggcgattcg agctgcagcg agcgagggag tgaaagctgc gggcgagagc tttagcctgg   4560
actgtcctac tctgcccgga cacggctgta agtcttgtga atttcatcgc atgaatactg   4620
gagataagaa tgtgatgtgt gccctgtgct atatgagagc ttacaaccat tgtgtttaca   4680
gtaagtgtga ttaactttag ctgggaaggc agagggtgac tgggtgctga ctggtttatt   4740
tatgtatgta ttctttatgt gtaggtcccg tctctgacgc agatgagacc cccacttcag   4800
agtgcatttc atcaccccca gaaattggcg aggaaccgcc cgaagatatt attcatagac   4860
cagttgcagt gagagtcacc gggcggagag cagctgtgga gagtttggat gacttgctac   4920
agggtgggga tgaacctttg gacttgtgta cccggaaacg ccccaggcac taagtgccac   4980
acatgtgtgt ttacttaagg tgatgtcagt atttataggg tgtggagtgc aataaaaata   5040
tgtgttgact ttaagtgcgt ggtttatgac tcaggggtgg ggactgtggg tatataagca   5100
ggtgcagacc tgtgtggtca gttcagagca ggactcatgg agatctggac ggtcttggaa   5160
gactttcacc agactagaca gctgctagag aactcatcgg agggagtctc ttacctgtgg   5220
agattctgct tcggtggggc tctagctaag ctagtccata gggccaaaca ggattataag   5280
gatcaatttg aggatatttt gagagagtgt cctggtattt ttgactctct caacttgggc   5340
catcagtctc actttaacca gagtattctg agagcccttg acttttctac tcctggcaga   5400
actaccgccg cggtagcctt ttttgccttt attcttgaca aatggagtca agaaacccat   5460
ttcagcaggg attaccgtct ggactgctta gcagtagctt tgtggagaac atggaggtgc   5520
cagcgcctga atgcaatctc cggctacttg ccagtacagc cggtagacac gctgaggatc   5580
ctgagtctcc agtcacccca ggaacaccaa cgccgccagc agccgcagca ggagcagcag   5640
caagaggagg aggaggatcg agaagagaac ccgagagccg gtctggaccc tccggtggcg   5700
gaggaggagg agtagctgac ttgtttcccg agctgcgccg ggtgctgact aggtcttcca   5760
gtggacggga gagggggatt aagcgggaga ggcatgagga gactagtcac agaactgaac   5820
tgactgtcag tctgatgagc cgcaggcgcc cagaatcggt gtggtggcat gaggtgcagt   5880
cgcaggggat agatgaggtc tcggtgatgc atgagaaata ttccctagaa caagtcaaga   5940
cttgttggtt ggagcctgag gatgattggg aggtagccat caggaattat gccaagttgg   6000
ctctgaagcc agataagaag tacaagatta ccaaactgat taatatcaga aattcctgct   6060
acatttcggg gaatggggcc gaggtggaga tcagtaccca ggagagggtg gccttcagat   6120
```

-continued

```
gctgcatgat gaatatgtac ccgggagtgg tgggcatgga gggagtcacc tttatgaacg   6180
cgaggttcag ggtgatgggg tataatgggg tggtctttat ggccaacacc aagctgacag   6240
tgcacggatg ctccttcttt ggcttcaata acatgtgcat cgaggcctgg ggcagtgttt   6300
cagtgagggg atgcagcttt tcagccaact ggatgggggt cgtgggcaga accaagagca   6360
aggtgtcagt gaagaaatgc ctgttcgaga ggtgccacct gggggtgatg agcgagggcg   6420
aagccaaagt caaacactgc gcctctaccg agacgggctg ctttgtgctg atcaagggca   6480
atgccaaagt caagcataat atgatctgtg gggcctcgga tgagcgcggc taccagatgc   6540
tgacctgcgc cggtgggaac agccatatgc tggccaccgt gcatgtggcc tcgcaccccc   6600
gcaagacatg gcccgagttc gagcacaacg tcatgacccg ctgcaatgtg cacctgggtt   6660
cccgccgagg catgttcatg ccctaccagt gcaacatgca atttgtgaag gtgctgctgg   6720
agcccgatgc catgtccaga gtgagcctga cgggggtgtt tgacatgaat gtggagctgt   6780
ggaaaattct gagatatgat gaatccaaga ccaggtgccg ggcctgcgaa tgcggaggca   6840
agcacgccag gcttcagccc gtgtgtgtgg aggtgacgga ggacctgcga cccgatcatt   6900
tggtgttgtc ctgcaacggg acggagttcg gctccagcgg ggaagaatct gactagagtg   6960
agtagtgttt gggggtgggt gggagcctgc atgaggggca gaatgactaa aatctgtgtt   7020
tttctgtgtg ttgcagcagc atgagcggaa gcgcctcctt tgagggaggg gtattcagcc   7080
cttatctgac ggggcgtctc ccctcctggg ctggagtgcg tcagaatgtg atgggatcca   7140
cggtggacgg ccggcccgtg cagcccgcga actcttcaac cctgacctac gcgaccctga   7200
gctcctcgtc cgtggacgca gctgccgccg cagctgctgc ttccgccgcc agcgccgtgc   7260
gcggaatggc cctgggtgcc ggctactaca gctctctggt ggccaactcg agttccacca   7320
ataatcccgc cagcctgaac gaggagaagc tgctgctgct gatggcccag ctcgaggccc   7380
tgacccagcg cctgggcgag ctgacccagc aggtggctca gctgcaggcg gagacgcggg   7440
ccgcggttgc cacggtgaaa accaaataaa aaatgaatca ataaataaac ggagacggtt   7500
gttgatttta acacagagtc ttgaatcttt atttgatttt tcgcgcgcgg taggccctgg   7560
accaccggtc tcgatcattg agcacccggt ggatttttc caggacccgg tagaggtggg   7620
cttggatgtt gaggtacatg ggcatgagcc cgtcccgggg gtggaggtag ctccattgca   7680
gggcctcgtg ctcgggggtg gtgttgtaaa tcacccagtc atagcagggg cgcagggcgt   7740
ggtgctgcac gatgtccttg aggaggagac tgatggccac gggcagcccc ttggtgtagg   7800
tgttgacgaa cctgttgagc tgggagggat gcatgcgggg ggagatgaga tgcatcttgg   7860
cctggatctt gagattggcg atgttcccgc ccagatcccg ccgggggttc atgttgtgca   7920
ggaccaccag cacggtgtat ccggtgcact tggggaattt gtcatgcaac ttggaaggga   7980
aggcatgaaa gaatttggag acgcccttgt gaccgcccag gttttccatg cactcatcca   8040
tgatgatggc aatgggcccg tgggcggcgg cctgggcaaa gacgtttcgg gggtcggaca   8100
catcgtagtt gtggtcctgg gtgagctcgt cataggccat tttaatgaat ttgggacgga   8160
gggtgcccga ttgggggacg aaggtgccct cgatcccggg ggcgtagttg ccctcgcaga   8220
tctgcatctc ccaggccttg agctcggagg gggggatcat gtccacctgc ggggcgatga   8280
aaaaaacggt ttccggggcg ggggagatga gctgcgccga aagcaggttc cggagcagct   8340
gggacttgcc gcagccggtg ggaccgtaga tgaccccgat gaccggctgc aggtggtagt   8400
tgagggagag acagctgccg tcctcgcgga ggagggggc cacctcgttc atcatctcgc   8460
gcacatgcat gttctcgcgc acgagttccg ccaggaggcg ctcgcccccc agcgagagga   8520
```

```
gctcttgcag cgaggcgaag tttttcagcg gcttgagccc gtcggccatg ggcattttgg   8580
agagggtctg ttgcaagagt tccagacggt cccagagctc ggtgatgtgc tctagggcat   8640
ctcgatccag cagacctcct cgtttcgcgg gttggggcga ctgcgggagt agggcaccag   8700
gcgatgggcg tccagcgagg ccagggtccg gtccttccag ggccgcaggg tccgcgtcag   8760
cgtggtctcc gtcacggtga aggggtgcgc gccgggctgg gcgcttgcga gggtgcgctt   8820
caggctcatc cggctggtcg agaaccgctc ccggtcggcg ccctgcgcgt cggccaggta   8880
gcaattgagc atgagttcgt agttgagcgc ctcggccgcg tggcccttgg cgcggagctt   8940
acctttggaa gtgtgtccgc agacgggaca gaggagggac ttgagggcgt agagcttggg   9000
ggcgaggaag acggactcgg gggcgtaggc gtccgcgccg cagctggcgc agacggtctc   9060
gcactccacg agccaggtga ggtcgggccg gtcggggtca aaaacgaggt ttcctccgtg   9120
ctttttgatg cgtttcttac ctctggtctc catgagctcg tgtccccgct gggtgacaaa   9180
gaggctgtcc gtgtccccgt agaccgactt tatgggtcgg tcctcgagcg gggtgccgcg   9240
gtcctcgtcg tagaggaacc ccgcccactc cgagacgaag gcccgggtcc aggccagcac   9300
gaaggaggcc acgtgggagg ggtagcggtc gttgtccacc agcgggtcca ccttctccag   9360
ggtatgcaag cacatgtccc cctcgtccac atccaggaag gtgattggct tgtaagtgta   9420
ggccacgtga ccgggggtcc cggccggggg ggtataaaag gggcgggcc cctgctcgtc    9480
ctcactgtct tccggatcgc tgtccaggag cgccagctgt tggggtaggt attccctctc   9540
gaaggcgggc atgacctcgg cactcaggtt gtcagtttct agaaacgagg aggatttgat   9600
attgacggtg ccgttggaga cgcctttcat gagcccctcg tccatctggt cagaaaagac   9660
gatctttttg ttgtcgagct tggtggcgaa ggagccgtag agggcgttgg agagcagctt   9720
ggcgatggag cgcatggtct ggttcttttc cttgtcggcg cgctccttgg cggcgatgtt   9780
gagctgtacg tactcgcgcg ccacgcactt ccattcgggg aagacggtgg tgagctcgtc   9840
gggcacgatt ctgacccgcc agccgcggtt gtgcagggtg atgaggtcca cgctggtggc   9900
cacctcgccg cgcaggggct cgttggtcca gcagaggcgc ccgcccttgc gcgagcagaa   9960
ggggggcagc gggtccagca tgagctcgtc ggggggtcg gcgtccacgg tgaagatgcc   10020
gggcaggagc tcggggtcaa agtagctgat gcaggtgccc agatcgtcca gcgccgcttg  10080
ccagtcgcgc acggccagcg cgcgctcgta ggggctgagg ggcgtgcccc agggcatggg  10140
gtgcgtgagc gcggaggcgt acatgccgca gatgtcgtag acgtagaggg gctcctcgag  10200
gacgccgatg taggtggggt agcagcgccc cccgcggatg ctggcgcgca cgtagtcgta  10260
cagctcgtgc gagggcgcga ggagccccgt gccgagattg gagcgctgcg gcttttcggc  10320
gcggtagacg atctggcgga agatggcgtg ggagttggag gagatggtgg gcctctggaa  10380
gatgttgaag tgggcgtggg gcaggccgac cgagtccctg atgaagtggg cgtaggagtc  10440
ctgcagcttg gcgacgagct cggcggtgac gaggacgtcc agggcgcagt agtcgagggt  10500
ctcttggatg atgtcatact tgagctggcc cttctgcttc cacagctcgc ggttgagaag  10560
gaactcttcg cggtccttcc agtactcttc gagggggaac ccgtcctgat cggcacggta  10620
agagcccacc atgtagaact ggttgacggc cttgtaggcg cagcagccct tctccacggg  10680
gagggcgtaa gcttgcgcgg ccttgcgcag ggaggtgtgg gtgagggcga aggtgtcgcg  10740
caccatgacc ttgaggaact ggtgcttgaa gtcgaggtcg tcgcagccgc cctgctccca  10800
gagttggaag tccgtgcgct tcttgtaggc ggggttgggc aaagcgaaag taacatcgtt  10860
```

gaagaggatc ttgcccgcgc ggggcatgaa gttgcgagtg atgcggaaag gctggggcac 10920
ctcggcccgg ttgttgatga cctgggcggc gaggacgatc tcgtcgaagc cgttgatgtt 10980
gtgcccgacg atgtagagtt ccacgaatcg cgggcggccc ttgacgtggg gcagcttctt 11040
gagctcgtcg taggtgagct cggcggggtc gctgaggccg tgctgctcga gggcccagtc 11100
ggcgacgtgg gggttggcgc tgaggaagga agtccagaga tccacggcca gggcggtctg 11160
caagcggtcc cggtactgac ggaactgctg gcccacggcc attttttcgg gggtgacgca 11220
gtagaaggtg cgggggtcgc cgtgccagcg gtcccacttg agctggaggg cgaggtcgtg 11280
ggcgagctcg acgagcggcg ggtccccgga gagtttcatg accagcatga aggggacgag 11340
ctgcttgccg aaggacccca tccaggtgta ggtttccaca tcgtaggtga ggaagagcct 11400
ttcggtgcga ggatgcgagc cgatggggaa gaactggatc tcctgccacc agttggagga 11460
atggctgttg atgtgatgga agtagaaatg ccgacggcgc gccgagcact cgtgcttgtg 11520
tttatacaag cgtccgcagt gctcgcaacg ctgcacggga tgcacgtgct gcacgagctg 11580
tacctgagtt cctttgacga ggaatttcag tgggcagtgg agcgctggcg gctgcatctg 11640
gtgttgtact acgtcctggc catcggcgtg gccatcgtct gcctcgatgg tggtcatgct 11700
gacgaggccg cgcgggaggc aggtccagac ctcggctcgg acgggtcgga gagcgaggac 11760
gagggcgcgc aggccggagc tgtccagggt cctgagacgc tgcggagtca ggtcagtggg 11820
cagcggcggc gcgcggttga cttgcaggag cttttccagg gcgcgcggga ggtccagatg 11880
gtacttgatc tccacggcgc cgttggtggc aacgtccacg gcttgcaggg tgccgtgccc 11940
ctggggcgcc accaccgtgc cccgtttctt tttgggcgct ggcggcggcg gctccatgct 12000
tagaatcggc ggcgaggacg cgcgccgggc ggcaggggcg gctcggggcc cggaggcagg 12060
ggcggcaggg gcacgtcggc gccgcgcgcg ggcaggttct ggtactgcgc ccggagaaga 12120
ctggcgtgag cgacgacgcg acggttgacg tcctggatct gacgcctctg ggtgaaggcc 12180
acgggacccg tgagtttgaa cctgaaagag agttcgacag aatcaatctc ggtatcgttg 12240
acggcagcct gccgcaggat ctcttgcacg tcgcccgagt tgtcctggta ggcgatctcg 12300
gtcatgaact gctcgatctc ctcctcctga aggtctccgc ggccggcgcg ctcgacggtg 12360
gccgcgaggt cgttggagat gcggcccatg agctgcgaga aggcgttcat gccggcctcg 12420
ttccagacgc ggctgtagac cacggctccg tcggggtcgc gcgcgcgcat gaccacctgg 12480
gcgaggttga tctccacgtg gcgcgtgaag accgcgtagt tgcagaggcg ctggtagagg 12540
tagttgagcg tggtggcgat gtgctcggtg acgaagaagt acatgatcca gcggcggagc 12600
ggcatctcgc tgacgtcgcc cagggcttcc aagcgctcca tggcctcgta gaagtccacg 12660
gcgaagttga aaaactggga gttgcgcgcc gagacggtca actcctcctc cagaagacgg 12720
atgagctcgg cgatggtggc gcgcacctcg cgctcgaagg ccccgggggg ctcctcttct 12780
tccatctcct cctcctcttc ctcctcctcc actaacatct cttctacttc ctcctcagga 12840
ggcggcggcg gggdgagggc cctgcgtcgc cggcggcgca cgggcagacg gtcgatgaag 12900
cgctcgatgg tctccccgcg ccggcgacgc atggtctcgg tgacggcgcg cccgtcctcg 12960
cggggccgca gcgtgaagac gccgccgcgc atctccaggt ggccgccggg ggggtctccg 13020
ttgggcaggg agagggcgct gacgatgcat cttatcaatt ggcccgtagg gactccgcgc 13080
aaggacctga gcgtctcgag atccacggga tccgaaaacc gctgaacgaa ggcttcgagc 13140
cagtcgcagt cgcaaggtag gctgagcccg gtttcttgtt cttcgggtat ttggtcggga 13200
ggcgggcggg cgatgctgct ggtgatgaag ttgaagtagg cggtcctgag acggcggatg 13260

```
gtggcgagga gcaccaggtc cttgggcccg gcttgctgga tgcgcagacg gtcggccatg  13320
ccccaggcgt ggtcctgaca cctggcgagg tccttgtagt agtcctgcat gagccgctcc  13380
acgggcacct cctcctcgcc cgcgcggccg tgcatgcgcg tgagcccgaa cccgcgctgg  13440
ggctggacga gcgccaggtc ggcgacgacg cgctcggcga ggatggcctg ctggatctgg  13500
gtgagggtgg tctggaagtc gtcgaagtcg acgaagcggt ggtaggctcc ggtgttgatg  13560
gtgtaggagc agttggccat gacggaccag ttgacggtct ggtggccggg gcgcacgagc  13620
tcgtggtact tgaggcgcga gtaggcgcgc gtgtcgaaga tgtagtcgtt gcaggtgcgc  13680
acgaggtact ggtatccgac gaggaagtgc ggcggcggct ggcggtagag cggccatcgc  13740
tcggtggcgg gggcgccggg cgcgaggtcc tcgagcatga ggcggtggta gccgtagatg  13800
tacctggaca tccaggtgat gccggcggcg gtggtggagg cgcgcgggaa ctcgcggacg  13860
cggttccaga tgttgcgcag cggcaggaag tagttcatgg tggccgcggt ctggcccgtg  13920
aggcgcgcgc agtcgtggat gctctagaca tacgggcaaa aacgaaagcg gtcagcggct  13980
cgactccgtg gcctggaggc taagcgaacg ggttgggctg cgcgtgtacc ccggttcgag  14040
tccctgctcg aatcaggctg gagccgcagc taacgtggta ctggcactcc cgtctcgacc  14100
caagcctgct aacgaaacct ccaggatacg gaggcgggtc gttttggcaa ttttcgtcag  14160
gccggaaatg aaactagtaa gcgcggaaag cggccgcccg cgatggctcg ctgccgtagt  14220
ctggagaaag aatcgccagg gttgcgttgc ggtgtgcccc ggttcgagcc tcggcgctcg  14280
tgccggccgg attccgcggc taacgtgggc gtggctgccc cgtcgtttcc aagacccctt  14340
agccagccga cttctccagt tacggagcga gcccctcttt tttttttttc ttgtgttttt  14400
gccagatgca tcccgtactg cggcagatgc gcccccaccc tccaccacaa ccgcccctac  14460
cgcagcagca gcaacagccg gcgcttctgc ccccgcccca gcagcagcag ccagccacta  14520
ccgcggcggc cgccgtgagc ggagccggcg ttcagtatga cctggccttg gaagagggcg  14580
aggggctggc gcggctgggg gcgtcgtcgc cggagcggca cccgcgcgtg cagatgaaaa  14640
gggacgctcg cgaggcctac gtgcccaagc agaacctgtt cagagacagg agcggcgagg  14700
agcccgagga gatgcgcgcc tcccgcttcc acgcggggcg ggagctgcgg cgcggcctgg  14760
accgaaagcg ggtgctgagg gacgaggatt tcgaggcgga cgagctgacg gggatcagcc  14820
ccgcgcgcgc gcacgtggcc gcggccaacc tggtcacggc gtacgagcag accgtgaagg  14880
aggagagcaa cttccaaaaa tccttcaaca accacgtgcg cacgctgatc gcgcgcgagg  14940
aggtgaccct gggcctgatg cacctgtggg acctgctgga ggccatcgtg cagaacccca  15000
cgagcaagcc gctgacggcg cagctgtttc tggtggtgca gcacagtcgg gacaacgaga  15060
cgttcaggga ggcgctgctg aatatcaccg agcccgaggg ccgctggctc ctggacctgg  15120
tgaacattct gcagagcatc gtggtgcagg agcgcgggct gccgctgtcc gagaagctgg  15180
cggccatcaa cttctcggtg ctgagcctgg gcaagtacta cgctaggaag atctacaaga  15240
ccccgtacgt gcccatagac aaggaggtga agatcgacgg gttttacatg cgcatgaccc  15300
tgaaagtgct gaccctgagc gacgatctgg gggtgtaccg caacgacagg atgcaccgcg  15360
cggtgagcgc cagccgccgg cgcgagctga gcgaccagga gctgatgcac agcctgcagc  15420
gggccctgac cggggccggg accgaggggg agagctactt tgacatgggc gcggacctgc  15480
gctggcagcc cagccgccgg gccttggaag ctgccggcgg ttccccctac gtggaggagg  15540
tggacgatga ggaggaggag ggcgagtacc tggaagactg atggcgcgac cgtatttttg  15600
```

-continued

```
ctagatgcag caacagccac cgccgcctcc tgatcccgcg atgcgggcgg cgctgcagag  15660

ccagccgtcc ggcattaact cctcggacga ttggacccag gccatgcaac gcatcatggc  15720

gctgacgacc cgcaatcccg aagcctttag acagcagcct caggccaacc ggctctcggc  15780

catcctggag gccgtggtgc cctcgcgctc gaaccccacg cacgagaagg tgctggccat  15840

cgtgaacgcg ctggtggaga acaaggccat ccgcggcgac gaggccgggc tggtgtacaa  15900

cgcgctgctg gagcgcgtgg cccgctacaa cagcaccaac gtgcagacga acctggaccg  15960

catggtgacc gacgtgcgcg aggcggtgtc gcagcgcgag cggttccacc gcgagtcgaa  16020

cctgggctcc atggtggcgc tgaacgcctt cctgagcacg cagcccgcca acgtgccccg  16080

gggccaggag gactacacca acttcatcag cgcgctgcgg ctgatggtgg ccgaggtgcc  16140

ccagagcgag gtgtaccagt cggggccgga ctacttcttc cagaccagtc gccagggctt  16200

gcagaccgtg aacctgagcc aggctttcaa gaacttgcag ggactgtggg gcgtgcaggc  16260

cccggtcggg gaccgcgcga cggtgtcgag cctgctgacg ccgaactcgc gcctgctgct  16320

gctgctggtg gcgcccttca cggacagcgg cagcgtgagc cgcgactcgt acctgggcta  16380

cctgcttaac ctgtaccgcg aggccatcgg gcaggcgcac gtggacgagc agacctacca  16440

ggagatcacc cacgtgagcc gcgcgctggg ccaggaggac ccgggcaacc tggaggccac  16500

cctgaacttc ctgctgacca accggtcgca gaagatcccg ccccagtacg cgctgagcac  16560

cgaggaggag cgcatcctgc gctacgtgca gcagagcgtg gggctgttcc tgatgcagga  16620

gggggccacg cccagcgccg cgctcgacat gaccgcgcgc aacatggagc ccagcatgta  16680

cgcccgcaac cgcccgttca tcaataagct gatggactac ttgcatcggg cggccgccat  16740

gaactcggac tactttacca acgccatctt gaacccgcat tggctcccgc cgcccgggtt  16800

ctacacgggc gagtacgaca tgcccgaccc caacgacggg ttcctgtggg acgacgtgga  16860

cagcagcgtg ttctcgccgc gccccaccgc caccaccgtg tggaagaaag agggcgggga  16920

ccggcggccg tcctcggcgc tgtccggtcg cgcgggtgct gccgcggcgg tgcccgaggc  16980

cgccagcccc ttcccgagcc tgccctttc gctgaacagc gtgcgcagca gcgagctggg  17040

tcggctgacg cggccgcgcc tgctgggcga ggaggagtac ctgaacgact ccttgttgag  17100

gcccgagcgc gagaagaact tccccaataa cgggatagag agcctggtgg acaagatgag  17160

ccgctggaag acgtacgcgc acgagcacag ggacgagccc cgagctagca gcagcgccac  17220

ccgtagacgc cagcggcacg acaggcagcg gggactggtg tgggacgatg aggattccgc  17280

cgacgacagc agcgtgttgg acttgggtgg gagtggtggt aacccgttcg ctcacttgcg  17340

cccccgtatc gggcgcctga tgtaagaatc tgaaaaaata aaaaacggta ctcaccaagg  17400

ccatggcgac cagcgtgcgt tcttctctgt tgtttgtagt agtatgatga ggcgcgtgta  17460

cccggagggt cctcctccct cgtacgagag cgtgatgcag caggcggtgg cggcggcgat  17520

gcagcccccg ctggaggcgc cttacgtgcc cccgcggtac ctggcgccta cggaggggcg  17580

gaacagcatt cgttactcgg agctggcacc cttgtacgat accacccggt tgtacctggt  17640

ggacaacaag tcggcggaca tcgcctcgct gaactaccag aacgaccaca gcaacttcct  17700

gaccaccgtg gtgcagaaca acgatttcac ccccacggag gccagcaccc agaccatcaa  17760

ctttgacgag cgctcgcggt ggggcggcca gctgaaaacc atcatgcaca ccaacatgcc  17820

caacgtgaac gagttcatgt acagcaacaa gttcaaggcg cgggtgatgg tctcgcgcaa  17880

gacccccaac ggggtgacgg taggggatga ttatgatggt agtcaggacg agctgaccta  17940

cgagtgggtg gagtttgagc tgcccgaggg caacttctcg gtgaccatga ccatcgatct  18000
```

gatgaacaac gccatcatcg acaactactt ggcggtgggg cggcagaacg gggtgctgga 18060
gagcgacatc ggcgtgaagt tcgacacgcg caacttccgg ctgggctggg accccgtgac 18120
cgagctggtg atgccgggcg tgtacaccaa cgaggccttc caccccgaca tcgtcctgct 18180
gcccggctgc ggcgtggact tcaccgagag ccgcctcagc aacctgctgg gcatccgcaa 18240
gcggcagccc ttccaggagg gcttccagat cctgtacgag gacctggagg ggggcaacat 18300
ccccgcgctg ctggacgtgg acgcctatga gaaaagcaag gaggatagcg ccgccgcggc 18360
gaccgcagcc gtggccaccg cctctaccga ggtgcggggc gataatttta ctagcgccgc 18420
agcagtggcc gaggcggctg aaaccgaaag taagatagtg atccagccgg tggagaagga 18480
cagcaaggac aggagctaca acgtgctcgc ggacaagaaa aacaccgcct accgcagctg 18540
gtacctggcc tacaactacg gcgaccccga gaagggcgtg cgctcctgga cgctgctcac 18600
cacctcggac gtcacctgcg gcgtggagca agtctactgg tcgctgcccg acatgatgca 18660
agacccggtc accttccgct ccacgcgtca agttagcaac tacccggtgg tgggcgccga 18720
gctcctgccc gtctactcca agagcttctt caacgagcag gccgtctact cgcagcagct 18780
gcgcgccttc acctcgctca cgcacgtttt caaccgcttc cccgagaacc agatcctcgt 18840
tcgcccgccc gcgcccacca ttaccaccgt cagtgaaaac gttcctgctc tcacagatca 18900
cgggaccctg ccgctgcgca gcagtatccg gggagtccag cgcgtgaccg tcactgacgc 18960
cagacgccgc acctgcccct acgtctacaa ggccctgggc gtagtcgcgc cgcgcgtcct 19020
ctcgagccgc accttctaaa aaatgtccat tctcatctcg cccagtaata acaccggttg 19080
gggcctgcgc gcgcccagca agatgtacgg aggcgctcgc caacgctcca cacaacaccc 19140
cgtgcgcgtg cgcgggcact tccgcgctcc ctggggcgcc ctcaagggcc gcgtgcgctc 19200
gcgcaccacc gtcgacgacg tgatcgacca ggtggtggcc gacgcgcgca actacacgcc 19260
cgccgccgcg cccgtctcca ccgtggacgc cgtcatcgac agcgtggtgg ccgacgcgcg 19320
ccggtacgcc cgcgccaaga gccggcggcg gcgcatcgcc cggcggcacc ggagcacccc 19380
cgccatgcgc gcggcgcgag ccttgctgcg cagggccagg cgcacgggac gcagggccat 19440
gctcagggcg gccagacgcg cggcctccgg cagcagcagc gccggcagaa cccgcagacg 19500
cgcggccacg gcggcggcgg cggccatcgc cagcatgtcc cgcccgcggc gcggcaacgt 19560
gtactgggtg cgcgacgccg ccaccggtgt gcgcgtgccc gtgcgcaccc gccccccctcg 19620
cacttgaaga tgctgacttc gcgatgttga tgtgtcccag cggcgaggag gatgtccaag 19680
cgcaaataca aggaagagat gctccaggtc atcgcgcctg agatctacgg ccccgcggcg 19740
gcggtgaagg aggaaagaaa gccccgcaaa ctgaagcggg tcaaaaagga caaaaaggag 19800
gaggaagatg acggactggt ggagtttgtg cgcgagttcg ccccccggcg gcgcgtgcag 19860
tggcgcgggc ggaaagtgaa accggtgctg cggcccggca ccacggtggt cttcacgccc 19920
ggcgagcgtt ccggctccgc ctccaagcgc tcctacgacg aggtgtacgg ggacgaggac 19980
atcctcgagc aggcggtcga gcgtctgggc gagtttgctt acggcaagcg cagccgcccc 20040
gcgcccttga aagaggaggc ggtgtccatc ccgctggacc acggcaaccc cacgccgagc 20100
ctgaagccgg tgaccctgca gcaggtgcta ccgagcgcgg cgccgcgccg ggcttcaag 20160
cgcgagggcg gcgaggatct gtacccgacc atgcagctga tggtgcccaa gcgccagaag 20220
ctggaggacg tgctggagca catgaaggtg gaccccgagg tgcagcccga ggtcaaggtg 20280
cggcccatca agcaggtggc tccgggcctg ggcgtgcaga ccgtggacat caagatcccc 20340
acggagccca tggaaacgca gaccgagccc gtgaagccca gcaccagcac catggaggtg 20400
cagacggatc cctggatgcc agcggcttcc accaccacca cccgccgaag acgcaagtac 20460
ggcgcgacca gcctgctgat gcccaactac gcgctgcatc cttccatcat ccccacgccg 20520
ggctaccgcg gcacgcgctt ctaccgcggc tacagcagcc gccgcaagac caccacccgc 20580
cgccgccgtc gtcgcacccg ccgcagcagc accgcgactt ccgccgccgc cttggtgcgg 20640
agagtgtacc gcagcgggcg cgagcctctg accctgccgc gcgcgcgcta ccacccgagc 20700
atcgccattt aactctgccg tcgcctcctt gcagatatgg ccctcacatg ccgcctccgc 20760
gtccccatta cgggctaccg aggaagaaag ccgcgccgta gaaggctgac ggggaacggg 20820
ctgcgtcgcc atcaccaccg gcggcggcgc gccatcagca agcggttggg gggaggcttc 20880
ctgcccgcgc tgatccccat catcgccgcg gcgatcgggg cgatccccgg catagcttcc 20940
gtggcggtgc aggcctctca gcgccactga gacacagctt ggaaaatttg taataaaaaa 21000
tggactgacg ctcctggtcc tgtgatgtgt gtttttagat ggaagacatc aatttttcgt 21060
ccctggcacc gcgacacggc acgcggccgt ttatgggcac ctggagcgac atcggcaaca 21120
gccaactgaa cgggggcgcc ttcaattgga gcagtctctg gagcgggctt aagaatttcg 21180
ggtccacgct caaaacctat ggcaacaagg cgtggaacag cagcacaggg caggcgctga 21240
gggaaaagct gaaagagcag aacttccagc agaaggtggt cgatggcctg gcctcgggca 21300
tcaacggggt ggtggacctg gccaaccagg ccgtgcagaa acagatcaac agccgcctgg 21360
acgcggtccc gcccgcgggg tccgtggaga tgccccaggt ggaggaggag ctgcctcccc 21420
tggacaagcg cggcgacaag cgaccgcgtc ccgacgcgga ggagacgctg ctgacgcaca 21480
cggacgagcc gcccccgtac gaggaggcgg tgaaactggg tctgcccacc acgcggcccg 21540
tggcgcctct ggccaccggg gtgctgaaac ccagcagcag cagcagccag cccgcgaccc 21600
tggacttgcc tccgcctgct tcccgcccct ccacagtggc taagcccctg ccgccggtgg 21660
ccgtcgcgtc gcgcgccccc cgaggccgcc cccaggcgaa ctggcagagc actctgaaca 21720
gcatcgtggg tctgggagtg cagagtgtga agcgccgccg ctgctattaa aagacactgt 21780
agcgcttaac ttgcttgtct gtgtgtatat gtatgtccgc cgaccagaag gaggaggaag 21840
aggcgcgtcg ccgagttgca agatggccac cccatcgatg ctgccccagt gggcgtacat 21900
gcacatcgcc ggacaggacg cttcggagta cctgagtccg ggtctggtgc agttcgcccg 21960
cgccacagac acctacttca gtctggggaa caagtttagg aaccccacgg tggcgcccac 22020
gcacgatgtg accaccgacc gcagccagcg gctgacgctg cgcttcgtgc ccgtggaccg 22080
cgaggacaac acctactcgt acaaagtgcg ctacacgctg gccgtgggcg acaaccgcgt 22140
gctggacatg gccagcacct actttgacat ccgcggcgtg ctggaccggg gccccagctt 22200
caaaccctac tccggcaccg cctacaacag tctggctccc aagggagcgc ccaacacctc 22260
acagtggata accaaagaca atggaactga taagacatac agttttggaa atgctccagt 22320
cagaggattg gacattacag aagagggtct ccaaatagga accgatgagt caggggggtga 22380
aagcaagaaa atttttgcag acaaaaccta tcagcctgaa cctcagcttg gagatgagga 22440
atggcatgat actattggag ctgaagacaa gtatggaggc agagcgctta aacctgccac 22500
caacatgaaa ccctgctatg ggtctttcgc caagccaact aatgctaagg gaggtcaggc 22560
taaaagcaga accaaggacg atggcactac tgagcctgat attgacatgg ccttctttga 22620
cgatcgcagt cagcaagcta gtttcagtcc agaacttgtt ttgtatactg agaatgtcga 22680
tctggacacc ccggataccc acattattta caaacctggc actgatgaaa caagttcttc 22740
tttcaacttg ggtcagcagt ccatgcccaa cagacccaac tacattgggt tcagagacaa 22800
ctttatcggt ctcatgtact acaacagcac tggcaatatg ggtgtgctgg ctggacaggc 22860
ctcccagctg aatgctgtgg tggacttgca ggacagaaac actgaactgt cctaccagct 22920
cttgcttgac tctctgggtg acagaactag gtatttcagt atgtggaatc aggcggtgga 22980
cagctacgac cccgatgtgc gcattattga aaatcacggt gtggaggatg aactccccaa 23040
ctattgcttc cctttgaatg gtgtgggctt tacagataca ttccagggaa ttaaggttaa 23100
aactaccaat aacggaacag caaatgctac agagtgggaa tctgatacct ctgtcaataa 23160
tgctaatgag attgccaagg gcaatccttt cgccatggag atcaacatcc aggccaacct 23220
gtggcggaac ttcctctacg cgaacgtggc gctgtacctg cccgactcct acaagtacac 23280
gccggccaac atcacgctgc ccaccaacac caacacctac gattacatga acggccgcgt 23340
ggtggcgccc tcgctggtgg acgcctacat caacatcggg gcgcgctggt cgctggaccc 23400
catggacaac gtcaacccct tcaaccacca ccgcaacgcg ggcctgcgct accgctccat 23460
gctcctgggc aacgggcgct acgtgccctt ccacatccag gtgccccaaa agtttttcgc 23520
catcaagagc ctcctgctcc tgcccgggtc ctacacctac gagtggaact tccgcaagga 23580
cgtcaacatg atcctgcaga gctccctcgg caacgacctg cgcacggacg gggcctccat 23640
cgccttcacc agcatcaacc tctacgccac cttcttcccc atggcgcaca acaccgcctc 23700
cacgctcgag gccatgctgc gcaacgacac caacgaccag tccttcaacg actacctctc 23760
ggcggccaac atgctctacc ccatcccggc caacgccacc aacgtgccca tctccatccc 23820
ctcgcgcaac tgggccgcct tccgcggatg gtccttcacg cgcctcaaga cccgcgagac 23880
gccctcgctc ggctccgggt tcgaccccta cttcgtctac tcgggctcca tcccctacct 23940
tgacggcacc ttctacctca accacacctt caagaaggtc tccatcacct tcgactcctc 24000
cgtcagctgg cccggcaacg accgcctcct gacgcccaac gagttcgaaa tcaagcgcac 24060
cgtcgacgga gaggggtaca acgtggccca gtgcaacatg accaaggact ggttcctggt 24120
ccagatgctg gcccactaca acatcggcta ccagggcttc tacgtgcccg agggctacaa 24180
ggaccgcatg tactccttct tccgcaactt ccagcccatg agccgccagg tcgtggacga 24240
ggtcaactac aaggactacc aggccgtcac cctggcctac cagcacaaca actcgggctt 24300
cgtcggctac ctcgcgccca ccatgcgcca gggccagccc taccccgcca actaccccta 24360
cccgctcatc ggcaagagcg ccgtcgccag cgtcacccag aaaaagttcc tctgcgaccg 24420
ggtcatgtgg cgcatcccct tctccagcaa cttcatgtcc atgggcgcgc tcaccgacct 24480
cggccagaac atgctctacg ccaactccgc ccacgcgcta gacatgaatt tcgaagtcga 24540
ccccatggat gagtccaccc ttctctatgt tgtcttcgaa gtcttcgacg tcgtccgagt 24600
gcaccagccc caccgcggcg tcatcgaggc cgtctacctg cgcacgccct tctcggccgg 24660
caacgccacc acctaagcct cttgcttctt gcaagatatg gcctgtgcgg gctccggcga 24720
gcaggagctc agggccatcc tccgcgacct gggctgcggg ccctgcttcc tgggcacctt 24780
cgacaagcgc ttcccgggat tcatggcccc gcacaagctg gcctgcgcca ttgtcaacac 24840
ggccggccgc gagaccgggg gcgagcactg gctggccttc gcctggaacc cgcgctccca 24900
cacctgctac ctcttcgacc cctttgggtt ctcggacgag cgcctcaagc agatctacca 24960
gttcgagtac gagggcctgc tgcgtcgcag cgccctggcc accgaggacc gctgcgtcac 25020
cctggaaaag tccacccaga ccgtgcaggg tccgcgctcg gccgcctgcg ggctcttctg 25080

```
ctgcatgttc ctgcacgcct tcgtgcactg gcccgaccgc cccatggaca agaaccccac  25140
catgaacttg ctgacggggg tgcccaacgg catgctccag tcgccccagg tggaacccac  25200
cctgcgccgc aaccaggagg cgctctaccg cttcctcaac gcccactccg cctactttcg  25260
atcccaccgc gcgcgcatcg agaaggccac cgccttcgac cgcatgaatc aagacatgta  25320
aaccgtgtgt gtatgtgaat gctttattca taataaacag cacatgttta tgccaccttc  25380
tctgaggctc tgactttatt tagaaatcga aggggttctg ccggctctcg gcgtgccccg  25440
cgggcaggga tacgttgcgg aactggtact tgggcagcca cttgaactcg gggatcagca  25500
gcttgggcac ggggaggtcg gggaacgagt cgctccacag cttgcgcgtg agttgcaggg  25560
cgcccagcag gtcgggcgcg gagatcttga aatcgcagtt gggacccgcg ttctgcgcgc  25620
gagagttgcg gtacacgggg ttgcagcact ggaacaccat cagggccggg tgcttcacgc  25680
tcgccagcac cgtcgcgtcg gtgatgccct ccacgtccag atcctcggcg ttggccatcc  25740
cgaagggggt catcttgcag gtctgccgcc ccatgctggg cacgcagccg ggcttgtggt  25800
tgcaatcgca gtgcaggggg atcagcatca tctgggcctg ctcggagctc atgcccgggt  25860
acatggcctt catgaaagcc tccagctggc ggaaggcctg ctgcgccttg ccgccctcgg  25920
tgaagaagac cccgcaggac ttgctagaga actggttggt ggcgcagccg gcgtcgtgca  25980
cgcagcagcg cgcgtcgttg ttggccagct gcaccacgct gcgcccccag cggttctggg  26040
tgatcttggc ccggtcgggg ttctccttca gcgcgcgctg cccgttctcg ctcgccacat  26100
ccatctcgat cgtgtgctcc ttctggatca tcacggtccc gtgcaggcac cgcagcttgc  26160
cctcggcctc ggtgcagccg tgcagccaca gcgcgcagcc ggtgctctcc cagttcttgt  26220
gggcgatctg ggagtgcgag tgcacgaagc cctgcaggaa gcggcccatc atcgcggtca  26280
gggtcttgtt gctggtgaag gtcagcggga tgccgcggtg ctcctcgttc acatacaggt  26340
ggcagatgcg gcggtacacc tcgccctgct cgggcatcag ctggaaggcg gacttcaggt  26400
cgctctccac gcggtaccgg tccatcagca gcgtcatcac ttccatgccc ttctcccagg  26460
ccgaaacgat cggcaggctc agggggttct tcaccgccat tgtcatctta gtcgccgccg  26520
ccgaagtcag gggtcgttc tcgtccaggg tctcaaacac tcgcttgccg tccttctcgg  26580
tgatgcgcac ggggggaag gcgaagccca cggccgccag ctcctcctcg gcctgccttt  26640
cgtcctcgct gtcctggctg atgtcttgca aaggcacatg cttggtcttg cggggtttct  26700
ttttgggcgg cagaggcggc ggcggagacg tgctgggcga gcgcgagttc tcgctcacca  26760
cgactatttc ttctccttgg ccgtcgtccg agaccacgcg gcggtaggca tgcctcttct  26820
ggggcagagg cggaggcgac gggctctcgc ggttcggcgg gcggctggca gagccccttc  26880
cgcgttcggg ggtgcgctcc tggcggcgct gctctgactg acttcctccg cggccggcca  26940
ttgtgttctc ctagggagca agcatggaga ctcagccatc gtcgccaaca tcgccatctg  27000
cccccgccgc cgccgacgag aaccagcaga atgaaagctt aaccgccccg ccgcccagcc  27060
ccacctccga cgcggcccca gacatgcaag agatggagga atccatcgag attgacctgg  27120
gctacgtgac gcccgcggag cacgaggagg agctggcagc gcgcttttca gccccggaag  27180
agaaccacca agagcagcca gagcaggaag cagagagcga gcagcagcag gctgggctcg  27240
agcatggcga ctacctgagc ggggcagagg acgtgctcat caagcatctg gcccgccaat  27300
gcatcatcgt caaggacgcg ctgctcgacc gcgccgaggt gcccctcagc gtggcggagc  27360
tcagccgcgc ctacgagcgc aacctcttct cgccgcgcgt gccccccaag cgccagccca  27420
acggcacctg cgagcccaac ccgcgcctca acttctaccc ggtcttcgcg gtgcccgagg  27480
```

```
ccctggccac ctaccacctc tttttcaaga accaaaggat ccccgtctcc tgccgcgcca  27540
accgcacccg cgccgacgcc ctgctcaacc tgggccccgg cgcccgccta cctgatatcg  27600
cctccttgga agaggttccc aagatcttcg agggtctggg cagcgacgag actcgggccg  27660
cgaacgctct gcaaggaagc ggagaggagc atgagcacca cagcgccctg gtggagttgg  27720
aaggcgacaa cgcgcgcctg gcggtgctca agcgcacggt cgagctgacc cacttcgcct  27780
acccggcgct caacctgccc cccaaggtca tgagcgccgt catggaccag gtgctcatca  27840
agcgcgcctc gcccctctcg gaggaggaga tgcaggaccc cgagagctcg gacgagggca  27900
agcccgtggt cagcgacgag cagctggcgc gctggctggg agcgagtagc accccccaga  27960
gcctggaaga gcggcgcaag ctcatgatgg ccgtggtcct ggtgaccgtg gagctggagt  28020
gtctgcgccg cttcttcgcc gacgcggaga ccctgcgcaa ggtcgaggag aacctgcact  28080
acctcttcag gcacgggttc gtgcgccagg cctgcaagat ctccaacgtg gagctgacca  28140
acctggtctc ctacatgggc atcctgcacg agaaccgcct ggggcagaac gtgctgcaca  28200
ccaccctgcg cggggaggcc cgccgcgact acatccgcga ctgcgtctac ctgtacctct  28260
gccacacctg gcagacgggc atgggcgtgt ggcagcagtg cctggaggag cagaacctga  28320
aagagctctg caagctcctg cagaagaacc tcaaggccct gtggaccggg ttcgacgagc  28380
gcaccaccgc ctcggacctg gccgacctca tcttccccga gcgcctgcgg ctgacgctgc  28440
gcaacgggct gcccgacttt atgagccaaa gcatgttgca aaactttcgc tctttcatcc  28500
tcgaacgctc cgggatcctg cccgccacct gctccgcgct gccctcggac ttcgtgccgc  28560
tgaccttccg cgagtgcccc ccgccgctct ggagccactg ctacctgctg cgcctggcca  28620
actacctggc ctaccactcg gacgtgatcg aggacgtcag cggcgagggc ctgctcgagt  28680
gccactgccg ctgcaacctc tgcacgccgc accgctccct ggcctgcaac ccccagctgc  28740
tgagcgagac ccagatcatc ggcaccttcg agttgcaagg ccccggcgac agcgagggca  28800
agggggtct caaactcacc ccggggctgt ggacctcggc ctacttgcgc aagttcgtgc  28860
ccgaggacta ccatcccttc gagatcaggt tctacgagga ccaatcccag ccgcccaagg  28920
ccaagctgtc ggcctgcgtc atcacccagg gggccatcct ggcccaattg caagccatcc  28980
agaaatcccg ccaagaattt ctgctgaaaa agggccacgg ggtctacttg gacccccaga  29040
ccggagagga gctcaacccc agcttccccc aggatgcccc gaggaagcag caagaagctg  29100
aaagtggagc tgccgccgcc ggaggatttg gaggaagact gggagagcag tcaggcagag  29160
gagatggaag actgggacag cactcaggca gaggaggaca gcctgcaaga cagtctggag  29220
gaggaagacg aggtggagga ggaggcagag gaagaagcag ccgccgccag accgtcgtcc  29280
tcggcggagg agaaagcaag cagcacggat accatctccg ctccgggtcg gggtcgcggc  29340
ggccgggccc acagtaggtg ggacgagacc gggcgcttcc cgaaccccac cacccagacc  29400
ggtaagaagg agcggcaggg atacaagtcc tggcgggggc acaaaaacgc catcgtctcc  29460
tgcttgcaag cctgcggggg caacatctcc ttcacccggc gctacctgct cttccaccgc  29520
ggggtgaact tcccccgcaa catcttgcat tactaccgtc acctccacag cccctactac  29580
tgtttccaag aagaggcaga aacccagcag cagcagcaga aaaccagcga cagctagaaa  29640
atccacagcg gcggcggcag gtggactgag gatcgcggcg aacgagccag cgcagacccg  29700
ggagctgagg aaccggatct ttcccaccct ctatgccatc ttccagcaga gtcgggggca  29760
ggagcaggaa ctgaaagtca agaaccgttc tctgcgctcg ctcacccgca gttgtctgta  29820
```

```
tcacaagagc gaagaccaac ttcagcgcac tctcgaggac gccgaggctc tcttcaacaa  29880
gtactgcgcg ctcactctta aagagtagcc cgcgcccgcc cacacacgga aaaaggcggg  29940
aattacgtca ccacctgcgc ccttcgcccg accatcatga gcaaagagat tcccacgcct  30000
tacatgtgga gctaccagcc ccagatgggc ctggccgccg gcgccgccca ggactactcc  30060
acccgcatga actggctcag tgccgggccc gcgatgatct cacgggtgaa tgacatccgc  30120
gcccaccgaa accagatact cctagaacag tcagcgatca ccaccacgcc ccgccatcac  30180
cttaatccgc gtaattggcc cgccgccctg gtgtaccagg aaattcccca gcccacgacc  30240
gtactacttc cgcgagacgc ccaggccgaa gtccagctga ctaactcagg tgtccagctg  30300
gccggcggcg ccgccctgtg tcgtcaccgc cccgctcagg gtataaagcg gctggtgatc  30360
cgaggcagag gcacacagct caacgacgag gtggtgagct cttcgctggg tctgcgacct  30420
gacggagtct tccaactcgc cggatcgggg agatcttcct tcacgcctcg tcaggccgtc  30480
ctgactttgg agagttcgtc ctcgcagccc cgctcgggcg gcatcggcac tctccagttc  30540
gtggaggagt tcactccctc ggtctacttc aacccctttct ccggctcccc cggccactac  30600
ccggacgagt tcatcccgaa cttcgacgcc atcagcgagt cggtggacgg ctacgattga  30660
atgtcccatg gtggcgcagc tgacctagct cggcttcgac acctggacca ctgccgccgc  30720
ttccgctgct tcgctcggga tctcgccgag tttgcctact ttgagctgcc cgaggagcac  30780
cctcagggcc cggcccacgg agtgcggatc gtcgtcgaag gggcctcga ctcccacctg  30840
cttcggatct tcagccagcg accgatcctg gtcgagcgcg agcaaggaca gacccgtctg  30900
accctgtact gcatctgcaa ccaccccggc ctgcatgaaa gtctttgttg tctgctgtgt  30960
actgagtata ataaaagctg agatcagcga ctactccgga cttccgtgtg ttcctgaatc  31020
catcaaccag tctttgttct tcaccgggaa cgagaccgag ctccagctcc agtgtaagcc  31080
ccacaagaag tacctcacct ggctgttcca gggctctccg atcgccgttg tcaaccactg  31140
cgacaacgac ggagtcctgc tgagcggccc tgccaacctt actttttcca cccgcagaag  31200
caagctccag ctcttccaac ccttcctccc cgggacctat cagtgcgtct cgggaccctg  31260
ccatcacacc ttccacctga tcccgaatac cacagcggcg ctccccgcta ctaacaacca  31320
aactacccac caacgacacc gtcgcgacct ttcctctggg tctaatacca ctaccggagg  31380
tgagctccga ggtcaaccaa cctctgggat ttactacggc ccctgggagg tggtagggtt  31440
aatagcgcta ggcctagttg cgggtgggct tttggctctc tgctacctat acctcccttg  31500
ctgttcgtac ttagtggtgc tgtgttgctg gtttaagaaa tggggaagat caccctagtg  31560
agctgcggtg cgctggtggc ggtggtgctt tcgattgtgg gactgggcag cgcggctgta  31620
gtgaaggaga aggccgatcc ctgcttgcat ttcaatcccg acaaatgcca gctgagtttt  31680
cagcccgatg gcaatcggtg cgcggtgctg atcaagtgcg gatgggaatg cgagaacgtg  31740
agaatcgagt acaataacaa gactcggaac aatactctcg cgtccgtgtg gcagcccggg  31800
gaccccgagt ggtacaccgt ctctgtcccc ggtgctgacg gctccccgcg caccgtgaat  31860
aatactttca tttttgcgca catgtgcgac acggtcatgt ggatgagcaa gcagtacgat  31920
atgtggcccc ccacgaagga gaacatcgtg gtcttctcca tcgcttacag cgtgtgcacg  31980
gtgctaatca ccgctatcgt gtgcctgagc attcacatgc tcatcgctat tcgccccaga  32040
aataatgccg aaaaagagaa acagccataa cacgtttttt cacacacctt tttcagacca  32100
tggcctctgt tactgcccta tttatttttt tgggccttgt gggcactagc agcacttttg  32160
atcataaaaa cctaactgtt tttgttggtt ctgatgttac actacctggg catcaatcgc  32220
```

```
accagagggt ttcatggtat cattttaata aacagaacac agcttataca ctttgcaaag  32280
gttatcagca agccacatat cgcagtggtc tttattacag atgcaataac aataacctca  32340
cactactctc agttaatgca aattattctg gcacatacta tggaaccaat tttaacgcaa  32400
aacaggacac ttactatagt gtcaaagtat tgaatccaac ctctcctaga actaccacta  32460
agcctaccac caccactact actgcgaaac ccactacacc taaaactacc aagaaaacca  32520
ctgtgaaaac tacaacaact aggaccacca caactacaga ggctaccacc agcacaacac  32580
ttgctaccac tacacacaca cacactgagc taaccttaca gaccactaat gatttgatcg  32640
ccctgttgca aaagggggat aacagcacca cttccaatga ggagataccc aaatccatga  32700
ttggcattat tgttgctgta gtggtgtgca tgttgatcat cgccttgtgc atggtgtact  32760
atgccttctg ctacagaaag cacagactga acgacaagct ggaacactta ctaagtgttg  32820
aattttaatt ttttagaacc atgaagatcc taggcctttt agttttttct atcattacct  32880
ctgctctatg caattctgac aatgaggacg ttactgtcgt tgtcggatca aattatacac  32940
taaaaggtcc agcaaaaggt atgctttcgt ggtattgttg gttcggaact gacgagcaac  33000
agacagaact ttgcaatgct caaaaaggca aaacctcaaa ttctaaaatc tctaattatc  33060
aatgcaatgg cactgactta gtattgctca atgtcacgaa agcatatgct ggcagttaca  33120
cctgccctgg agatgatgcc gacaatatga ttttttacaa agtggaagtg gttgatccca  33180
ctactccacc gcccaccacc acaactactc ataccacaca cacagaacaa acaccagagg  33240
cagcagaagc agagttggcc ttccaggttc acggagattc ctttgctgtc aatacccccta  33300
cacccgatca gcggtgtccg gggctgctcg tcagcggcat tgtcggtgtg ctttcgggat  33360
tagcagttat aatcatctgc atgttcattt ttgcttgctg ctatagaagg ctttaccgac  33420
aaaaatcaga cccactgctg aacctctatg tttaattttt tccagagcca tgaaggcagt  33480
tagcactcta gtttttttgtt ctttgattgg cattgttttt tgcaatccta ttcctagagt  33540
tagctttatt aaagatgtga atgttactga ggggggcaat gtgacactgg taggtgtaga  33600
gggtgctgaa aacaccacct ggacaaaata ccacctcaat gggtggaaag atatttgcaa  33660
ttggagtgta ttagtttata catgtgaggg agttaatctt accattgtca atgccacctc  33720
agctcaaaat ggtagaattc aaggacaaag tgtcagtgta tctaatgggt attttaccca  33780
acatactttt atctatgacg ttaaagtcat accactgcct acgcctagcc cacctagcac  33840
taccacacag acaaccacat acagtacatc aaatcagcct accaccacta cagcagcaga  33900
ggttgccagc tcgtctgggg tccgagtggc atttttgatg ttggccccat ctagcagtcc  33960
cactgctagt accaatgagc agactactga atttttgtcc actgtcgaga gccacaccac  34020
agctacctcg agtgccttct ctagcaccgc caatctctcc tcgctttcct ctacaccaat  34080
cagtcccgct actactccta gccccgctcc tcttcccact cccctgaagc aaactgagga  34140
cagcggcatg caatggcaga tcaccctgct cattgtgatc gggttggtca tcctggccgt  34200
gttgctctac tacatcttct gccgccgcat tcccaacgcg caccgcaagc cggcctacaa  34260
gcccatcgtt atcgggcagc cggagccgct tcaggtggaa gggggtctaa ggaatcttct  34320
cttctctttt acagtatggt gattgaacta tgattcctag acaattcttg atcactattc  34380
ttatctgcct cctccaagtc tgtgccaccc tcgctctggt ggccaacgcc agtccagact  34440
gtattgggcc cttcgcctcc tacgtgctct ttgccttcat cacctgcatc tgctgctgta  34500
gcatagtctg cctgcttatc accttcttcc agttcattga ctggatcttt gtgcgcatcg  34560
```

-continued

```
cctacctgcg ccaccacccc cagtaccgcg accagcgagt ggcgcggctg ctcaggctcc  34620
tctgataagc atgcgggctc tgctacttct cgcgcttctg ctgttagtgc tcccccgtcc  34680
cgtcgacccc cggtccccca ctcagtcccc cgaggaggtc cgcaaatgca aattccaaga  34740
accctggaaa ttcctcaaat gctaccgcca aaaatcagac atgcatccca gctggatcat  34800
gatcattggg atcgtgaaca ttctggcctg caccctcatc tcctttgtga tttacccctg  34860
ctttgacttt ggttggaact cgccagaggc gctctatctc ccgcctgaac ctgacacacc  34920
accacagcag caacctcagg cacacgcact accaccacca cagcctaggc cacaatacat  34980
gcccatatta gactatgagg ccgagccaca gcgacccatg ctccccgcta ttagttactt  35040
caatctaacc ggcggagatg actgacccac tggccaacaa caacgtcaac gaccttctcc  35100
tggacatgga cggccgcgcc tcggagcagc gactcgccca acttcgcatt cgccagcagc  35160
aggagagagc cgtcaaggag ctgcaggacg gcatagccat ccaccagtgc aagaaaggca  35220
tcttctgcct ggtgaaacag gccaagatct cctacgaggt cacccagacc gaccatcgcc  35280
tctcctacga gctcctgcag cagcgccaga agttcacctg cctggtcgga gtcaacccca  35340
tcgtcatcac ccagcagtcg ggcgatacca aggggtgcat ccactgctcc tgcgactccc  35400
ccgactgcgt ccacactctg atcaagaccc tctgcggcct ccgcgacctc ctccccatga  35460
actaatcacc ccccttatcca gtgaaataaa gatcatattg atgatgattt aaataaaaaa  35520
aaaaaaaaaa taatcatttg atttgaaata aagatacaat catattgatg atttgagttt  35580
taaaaaaata aagaatcact tacttgaaat ctgataccag gtctctgtcc atgttttctg  35640
ccaacaccac ttcactcccc tcttcccagc tctggtactg caggccccgg cgggctgcaa  35700
acttcctcca cacgctgaag ggatgtcaa attcctcctg tccctcaatc ttcattttat  35760
cttctatcag atgtccaaaa agcgcgtccg ggtggatgat gacttcgacc ccgtctaccc  35820
ctacgatgca gacaacgcac cgaccgtgcc cttcatcaac ccccccttcg tctcttcaga  35880
tggattccaa gagaagcccc tgggggtgct gtccctgcga ctggccgacc ccgtcaccac  35940
caagaacggg gaaatcaccc tcaagctggg agagggggtg gacctcgact cctcgggaaa  36000
actcatctcc aacacggcca ccaaggccgc cgcccctctc agtttttcca acaaatttcc  36060
cttaacatgg ataccccttt ttacaccaaa gatggaaaat taaccatgca ggtcactgca  36120
ccgctaaagt tagcaaacac agccatattg aacacactag ccatggcata tggaaatgga  36180
ttagggctaa gcaacaacgc tcttaccgtt cagttacaat ctccactcac ctttaacaac  36240
agcaaggttg ctatcaacct ggaaaatgga ccactaaacg tgacatcaaa tagacttagc  36300
attaattgca agaggggtgt ctatgtcacc accacaggag atgcaatcga aaccaacata  36360
agttggccaa atgctattaa atttatagga aatgcaatgg gtgtcaatat tgatacaaac  36420
aaaggcttgc aatttggcac caccagcact gtcacagatg tgaccgatgc tttccccata  36480
caagtcaaac ttggggctgg tcttgcattt gatagcactg gagctattgt tgcatggaac  36540
aaagaggatg acagtctcac tttgtggact acaccagatc catctccaaa ttgcaagata  36600
gcatctgaca aagatgctaa actcacactt tgcttgacaa agtgtggaag tcaaattctg  36660
ggtactgtga ctgtattggc agtgaataat ggaagtctca acccaatcac aaacacagta  36720
agcactgccc ttgtatcact taaattcgac gccaatggag cactcttgga aaaatcaacc  36780
ctaaacagag aatattggaa ctacagacaa ggagatctca ttccaggtac accatatacc  36840
catgcagtag gtttcatgcc caacaagaaa gcctacccta aaaacacaac tgcagcttcc  36900
aaaagccaca ttgtgggga cgtctatcta gacggggatg tagataagcc cctatctctc  36960
```

ataatcactt ttaatgaaac tgatgatgaa tcatgtgact attgcatgaa ctttcaatgg 37020
aaatggggtg ctgatcaata caaggacaaa acactcgcta ccagctcctt caccttctcc 37080
tacatcgccc aagaatgaac actgtatccc accctgcatg ccaacccttc ccacccact 37140 ctgtctgtgg aaaaaactct gaaacacaaa ataaaataaa gttcaagtgt tttattgatt 37200
caacagtttt acaggattcg agcagttatt tttcctccac cctcccagga catggaatac 37260
accaccctct ccccccgcac agccttgaac atctgaatgc cattggtgat ggacatgctt 37320
ttggtctcca cgttccacac agtttcagag cgagccagtc tcgggtcggt cagggagatg 37380
aaaccctccg ggcactcccg catctgcacc tcacagctca acagctgagg attgtcctcg 37440
gtggtcggga tcacggttat ctggaagaag cagaagagcg gcggtgggaa tcatagtccg 37500
cgaacgggat cggccggtgg tgccgcatca ggccccgcag cagtcgctgc cgccgccgct 37560
ccgtcaagct gctgctcagg gggtccgggt ccagggactc cctcagcatg atgcccacgg 37620
ccctcagcat cagtcgtctg gtgcggcggg cgcagcagcg catgcggatc tcgctcaggt 37680
cgctgcagta cgtgcaacac aggaccacca ggttgttcaa cagtccatag ttcaacacgc 37740
tccagccgaa actcatcgcg ggaaggatgc tacccacgtg gccgtcgtac cagatcctca 37800
ggtaaatcaa gtggcgcccc ctccagaaca cgctgcccac gtacatgatc tccttgggca 37860
tgtggcggtt caccacctcc cggtaccaca tcaccctttg gttgaacatg cagccccgga 37920
tgatcctgcg gaaccacagg gccagcaccg ccccgcccgc catgcagcga agagaccccg 37980
ggtcccgaca atggcaatgg aggacccacc gctcgtaccc gtggatcatc tgggagctga 38040
acaagtctat gttggcacag cacaggcaca cgctcatgca tctcttcagc actctcagct 38100
cctcgggggt caaaaccata tcccagggca cggggaactc ttgcaggaca gcgaaccccg 38160
cagaacaggg caatcctcgc acataactta cattgtgcat ggacagggta tcgcaatcag 38220
gcagcaccgg gtgatcctcc accagagaag cgcgggtctc ggtctcctca cagcgtggta 38280
agggggccgg ccgatacggg tgatggcggg acgcggctga tcgtgttcgc gaccgtgtca 38340
tgatgcagtt gctttcggac attttcgtac ttgctgtagc agaacctggt ccgggcgctg 38400
cacaccgatc gccggcggcg gtctcggcgc ttggaacgct cggtgttgaa attgtaaaac 38460
agccactctc tcagaccgtg cagcagatct agggcctcag gagtgatgaa gatcccatca 38520
tgcctgatgg ctctgatcac atcgaccacc gtggaatggg ccagacccag ccagatgatg 38580
caattttgtt gggtttcggt gacggcgggg gagggaagaa caggaagaac catgattaac 38640
ttttaatcca aacggtctcg gagtacttca aaatgaagat cgcggagatg gcacctctcg 38700
cccccgctgt gttggtggaa aataacagcc aggtcaaagg tgatacggtt ctcgagatgt 38760
tccacggtgg cttccagcaa agcctccacg cgcacatcca gaaacaagac aatagcgaaa 38820
gcgggagggt tctctaattc ctcaatcatc atgttacact cctgcaccat ccccagataa 38880
ttttcatttt tccagccttg aatgattcga actagttcct gaggtaaatc caagccagtc 38940
atgataaaga gctcgcgcag agcgccctcc accggcattc ttaagcacac cctcataatt 39000
ccaagatatt ctgctcctgg ttcacctgca gcagattgac aagcggaata tcaaaatctc 39060
tgccgcgatc cctgagctcc tccctcagca ataactgtaa gtactctttc atatcctctc 39120
cgaaattttt agccatagga ccaccaggaa taagattagg gcaagccaca gtacagataa 39180
accgaagtcc tccccagtga gcattgccaa atgcaagact gctataagca tgctggctag 39240
acccggtgat atcttccaga taactggaca gaaaatcacc caggcaattt ttaagaaaat 39300

```
caacaaaaga aaaatcctcc aggtgcacgt ttagggcctc gggaacaacg atggagtaaa  39360

cgcaagcggt gcgttccagc atggttagtt agctgatctg taaaaaaaca aaaaataaaa  39420

cattaaacca tgctagcctg gcgaacaggt gggtaaatcg ttctctccag caccaggcag  39480

gccacggggt ctccggcgcg accctcgtaa aaattgtcgc tatgattgaa aaccatcaca  39540

gagagacgtt cccggtggcc ggcgtgaatg attcgacaag atgaatacac ccccggaaca  39600

ttggcgtccg cgagtgaaaa aaagcgcccg aggaagcaat aaggcactac aatgctcagt  39660

ctcaagtcca gcaaagcgat gccatgcgga tgaagcacaa aattctcagg tgcgtacaaa  39720

atgtaattac tcccctcctg cacaggcagc aaagccccg atccctccag gtacacatac  39780

aaagcctcag cgtccatagc ttaccgagca gcagcacaca acaggcgcaa gagtcagaga  39840

aaggctgagc tctaacctgt ccacccgctc tctgctcaat atatagccca gatctacact  39900

gacgtaaagg ccaaagtcta aaaatacccg ccaaataatc acacacgccc aacacacgcc  39960

cagaaaccgg tgacacactc agaaaaatac gcgcacttcc tcaaacgccc aaactgccgt  40020

catttccggg ttcccacgct acgtcatcag aattcgactt tcaaattccg tcgaccgtta  40080

aaaacgtcac ccgccccgcc cctaacggtc gcccgtctct cggccaatca cagccccgca  40140

tccccaaatt caaacacctc atttgcatat taacgcgcac caaaagtttg aggtatatta  40200

ttgatgatgt taattaattg gttc                                          40224
```

<210> SEQ ID NO 3
<211> LENGTH: 6451
<212> TYPE: DNA
<213> ORGANISM: Artificial Sequence
<220> FEATURE:
<223> OTHER INFORMATION: Synthesized

<400> SEQUENCE: 3

```
tccacggtgg cttccagcaa agcctccacg cgcacatcca gaaacaagac aatagcgaaa     60

gcgggagggt tctctaattc ctcaatcatc atgttacact cctgcaccat ccccagataa    120

ttttcatttt tccagccttg aatgattcga actagttcct gaggtaaatc caagccagtc    180

atgataaaga gctcgcgcag agcgccctcc accggcattc ttaagcacac cctcataatt    240

ccaagatatt ctgctcctgg ttcacctgca gcagattgac aagcggaata tcaaaatctc    300

tgccgcgatc cctgagctcc tccctcagca ataactgtaa gtactctttc atatcctctc    360

cgaaattttt agccatagga ccaccaggaa taagattagg gcaagccaca gtacagataa    420

accgaagtcc tccccagtga gcattgccaa atgcaagact gctataagca tgctggctag    480

acccggtgat atcttccaga taactggaca gaaaatcacc caggcaattt ttaagaaaat    540

caacaaaaga aaaatcctcc aggtgcacgt ttagggcctc gggaacaacg atggagtaaa    600

cgcaagcggt gcgttccagc atggttagtt agctgatctg taaaaaaaca aaaaataaaa    660

cattaaacca tgctagcctg gcgaacaggt gggtaaatcg ttctctccag caccaggcag    720

gccacggggt ctccggcgcg accctcgtaa aaattgtcgc tatgattgaa aaccatcaca    780

gagagacgtt cccggtggcc ggcgtgaatg attcgacaag atgaatacac ccccggaaca    840

ttggcgtccg cgagtgaaaa aaagcgcccg aggaagcaat aaggcactac aatgctcagt    900

ctcaagtcca gcaaagcgat gccatgcgga tgaagcacaa aattctcagg tgcgtacaaa    960

atgtaattac tcccctcctg cacaggcagc aaagccccg atccctccag gtacacatac   1020

aaagcctcag cgtccatagc ttaccgagca gcagcacaca acaggcgcaa gagtcagaga   1080

aaggctgagc tctaacctgt ccacccgctc tctgctcaat atatagccca gatctacact   1140
```

gacgtaaagg ccaaagtcta aaaatacccg ccaaataatc acacacgccc aacacacgcc 1200
cagaaaccgg tgacacactc agaaaaatac gcgcacttcc tcaaacgccc aaactgccgt 1260
catttccggg ttcccacgct acgtcatcag aattcgactt tcaaattccg tcgaccgtta 1320
aaaacgtcac ccgccccgcc cctaacggtc gcccgtctct cggccaatca cagccccgca 1380
tccccaaatt caaacacctc atttgcatat taacgcgcac caaaagtttg aggtatatta 1440
ttgatgatgt taattaattg gttccactga gcgtcagacc ccttaataag atgatcttct 1500
tgagatcgtt ttggtctgcg cgtaatctct tgctctgaaa acgaaaaaac cgccttgcag 1560
ggcggttttt cgaaggttct ctgagctacc aactctttga accgaggtaa ctggcttgga 1620
ggagcgcagt caccaaaact tgtcctttca gtttagcctt aaccggcgca tgacttcaag 1680
actaactcct ctaaatcaat taccagtggc tgctgccagt ggtgcttttg catgtctttc 1740
cgggttggac tcaagacgat agttaccgga taaggcgcag cggtcggact gaacgggggg 1800
ttcgtgcata cagtccagct tggagcgaac tgcctacccg gaactgagtg tcaggcgtgg 1860
aatgagacaa acgcggccat aacagcggaa tgacaccggt aaaccgaaag gcaggaacag 1920
gagagcgcac gagggagccg ccagggggaa acgcctggta tctttatagt cctgtcgggt 1980
ttcgccacca ctgatttgag cgtcagattt cgtgatgctt gtcagggggg cggagcctat 2040
ggaaaaacgg ctttgccgcg gccctctcac ttccctgtta agtatcttcc tggcatcttc 2100
caggaaatct ccgccccgtt cgtaagccat ttccgctcgc cgcagtcgaa cgaccgagcg 2160
tagcgagtca gtgagcgagg aagcggaata tatcctgtat cacatattct gctgacgcac 2220
cggtgcagcc tttttctcc tgccacatga agcacttcac tgacaccctc atcagtgcca 2280
acatagtaag ccagtataca ctccgctagc gctgaggtct gcctcgtgaa gaaggtgttg 2340
ctgactcata ccaggcctga atcgccccat catccagcca gaaagtgagg gagccacggt 2400
tgatgagagc tttgttgtag gtggaccagt tggtgatttt gaacttttgc tttgccacgg 2460
aacggtctgc gttgtcggga agatgcgtga tctgatcctt caactcagca aaagttcgat 2520
ttattcaaca aagccacgtt gtgtctcaaa atctctgatg ttacattgca caagataaaa 2580
atatatcatc atgaacaata aaactgtctg cttacataaa cagtaataca aggggtgtta 2640
tgagccatat tcaacgggaa acgtcttgct cgaggccgcg attaaattcc aacatggatg 2700
ctgatttata tgggtataaa tgggctcgcg ataatgtcgg gcaatcaggt gcgacaatct 2760
atcgattgta tgggaagccc gatgcgccag agttgtttct gaaacatggc aaaggtagcg 2820
ttgccaatga tgttacagat gagatggtca gactaaactg gctgacggaa tttatgcctc 2880
ttccgaccat caagcatttt atccgtactc ctgatgatgc atggttactc accactgcga 2940
tccccgggaa aacagcattc caggtattag aagaatatcc tgattcaggt gaaaatattg 3000
ctgatgcgct ggcagtgttc ctgcgccggt tgcattcgat tcctgtttgt aattgtcctt 3060
ttaacagcga tcgcgtattt cgtctcgctc aggcgcaatc acgaatgaat aacggtttgg 3120
ttgatgcgag tgattttgat gacgagcgta atggctggcc tgttgaacaa gtctggaaag 3180
aaatgcataa gcttttgcca ttctcaccgg attcagtcgt cactcatggt gatttctcac 3240
ttgataacct tatttttgac gaggggaaat taataggttg tattgatgtt ggacgagtcg 3300
gaatcgcaga ccgataccag gatcttgcca tcctatggaa ctgcctcggt gagttttctc 3360
cttcattaca gaaacggctt tttcaaaaat atggtattga taatcctgat atgaataaat 3420
tgcagtttca tttgatgctc gatgagtttt tctaatcaga attggttaat tggttgtaac 3480
actggcagag cattacgctg acttgacggg acggcttagg gttaggcgtt ttgcgctgct 3540
tcgcgatgta cgggccagat atacgcaatg tagtcttatg caatactctt gtagtcttgc 3600
aacatggtaa cgatgagtta gcaacatgcc ttacaaggag agaaaaagca ccgtgcatgc 3660
cgattggtgg aagtaaggtg gtacgatcgt gccttattag gaaggcaaca gacgggtctg 3720
acatggattg gacgaaccac tgaattgccg cattgcagag atattgtatt taagtgccta 3780
gctcgataca taaacctctg gctaactaga gaacccactg cttactggct tatcgaaatt 3840
aatacgactc actataggga gacccagcca ccatggtgag caagggcgag gagctgttca 3900
ccggggtggt gcccatcctg gtcgagctgg acggcgacgt aaacggccac aagttcagcg 3960
tgtccggcga gggcgagggc gatgccacct acggcaagct gaccctgaag ttcatctgca 4020
ccaccggcaa gctgcccgtg ccctggccca ccctcgtgac caccctgacc tacggcgtgc 4080
agtgcttcag ccgctacccc gaccacatga agcagcacga cttcttcaag tccgccatgc 4140
ccgaaggcta cgtccaggag cgcaccatct tcttcaagga cgacggcaac tacaagaccc 4200
gcgccgaggt gaagttcgag ggcgacaccc tggtgaaccg catcgagctg aagggcatcg 4260
acttcaagga ggacggcaac atcctggggc acaagctgga gtacaactac aacagccaca 4320
acgtctatat catggccgac aagcagaaga acggcatcaa ggtgaacttc aagatccgcc 4380
acaacatcga ggacggcagc gtgcagctcg ccgaccacta ccagcagaac acccccatcg 4440
gcgacggccc cgtgctgctg cccgacaacc actacctgag cacccagtcc gccctgagca 4500
aagaccccaa cgagaagcgc gatcacatgg tcctgctgga gttcgtgacc gccgccggga 4560
tcactctcgg catggacgag ctgtacaagt aaagcggccg ctcgagtcta gagggcccgt 4620
ttaaacccgc tgatcagcct cgactgtgcc ttctagttgc cagccatctg ttgtttgccc 4680
ctcccccgtg ccttccttga ccctggaagg tgccactccc actgtccttt cctaataaaa 4740
tgaggaaatt gcatcgcatt gtctgagtag gtgtcattct attctggggg gtggggtggg 4800
gcaggacagc aagggggagg attgggaaga caatagcagg catgctgggg atgcggtggg 4860
ctctatggct tctgaggcgg aaagaaccag ctggggctct agggggtatc cccacgcgcc 4920
ctgtagcggc gcattaatag ggataacagg gtaatataca aacgaggccc tttcgtcttt 4980
aattaacatc atcaataata tacctcaaac ttttggtgcg cgttaatatg caaatgaggt 5040
gtttgaattt ggggatgcgg ggctgtgatt ggccgagaga cgggcgaccg ttaggggcgg 5100
ggcgggtgac gttttgatga cgtggccgtg aggcggagcc ggtttgcaag ttctcgtggg 5160
aaaagtgacg tcaaacgagg tgtggtttga acacggaaat actcaatttt cccgcgctct 5220
ctgacaggaa atgaggtgtt tctgggcgga tgcaagtgaa aacgggccat tttcgcgcga 5280
aaactgaatg aggaagtgaa aatctgagta atttcgcgtt tatggcaggg aggagtattt 5340
gccgagggcc gagtagactt tgaccgatta cgtgggggtt tcgattaccg tatttttcac 5400
ctaaatttcc gcgtacggtg tcaaagtccg gtgtttttac gtaggtgtca gctgatcgcc 5460
agggtattta aacctgcgct ctctagtcaa gaggccactc ttgagtgcca gcgagtagag 5520
ttttctcctc cgcgccgcga gtcagatcta cactttgaaa gatgaggcac ctgagagacc 5580
tgcccggtaa tgttttcctg gctactggga acgagattct ggaactggtg gtggacgcca 5640
tgatgggtga cgaccctcct gagcccccta ccccatttga ggcgccttcg ctgtacgatt 5700
tgtatgatct ggaggtggat gtgcccgaga acgaccccaa cgaggaggcg gtgaatgatt 5760
tgtttagcga tgccgcgctg ctggctgccg agcaggctaa tacggactct ggctcagaca 5820
gcgattcctc tctccatacc ccgagacccg gcagaggtga gaaaaagatc cccgagctta 5880
aaggggaaga gctcgacctg cgctgctatg aggaatgctt gcctccgagc gatgatgagg 5940
aggacgagga ggcgattcga gctgcagcga gcgagggagt gaaagctgcg ggcgagagct 6000
ttagcctgga ctgtcctact ctgcccggac acggctgtaa gtcttgtgaa tttcatcgca 6060
tgaatactgg agataagaat gtgatgtgtg ccctgtgcta tatgagagct tacaaccatt 6120
gtgtttacag taagtgtgat taactttagc tgggaaggca gagggtgact gggtgctgac 6180
tggtttattt atgtatgtat tctttatgtg taggtcccgt ctctgacgca gatgagaccc 6240
ccacttcaga gtgcatttca tcacccccag aaattggcga ggaaccgccc gaagatatta 6300
ttcatagacc agttgcagtg agagtcaccg ggcggagagc agctgtggag agtttggatg 6360
acttgctaca gggtggggat gaacctttgg acttgtgtac ccggaaacgc cccaggcact 6420
aagtgccaca catgtgtgtt tacttggatc c 6451

<210> SEQ ID NO 4
<211> LENGTH: 33146
<212> TYPE: DNA
<213> ORGANISM: Artificial Sequence
<220> FEATURE:
<223> OTHER INFORMATION: Synthesized

<400> SEQUENCE: 4
ttaattaatt ggttccactg agcgtcagac cccttaataa gatgatcttc ttgagatcgt 60
tttggtctgc gcgtaatctc ttgctctgaa aacgaaaaaa ccgccttgca gggcggtttt 120
tcgaaggttc tctgagctac caactctttg aaccgaggta actggcttgg aggagcgcag 180
tcaccaaaac ttgtcctttc agtttagcct taaccggcgc atgacttcaa gactaactcc 240
tctaaatcaa ttaccagtgg ctgctgccag tggtgctttt gcatgtcttt ccgggttgga 300
ctcaagacga tagttaccgg ataaggcgca gcggtcggac tgaacggggg gttcgtgcat 360
acagtccagc ttggagcgaa ctgcctaccc ggaactgagt gtcaggcgtg gaatgagaca 420
aacgcggcca taacagcgga atgacaccgg taaaccgaaa ggcaggaaca ggagagcgca 480
cgagggagcc gccaggggga aacgcctggt atctttatag tcctgtcggg tttcgccacc 540
actgatttga gcgtcagatt tcgtgatgct tgtcaggggg gcggagccta tggaaaaacg 600
gctttgccgc ggccctctca cttccctgtt aagtatcttc ctggcatctt ccaggaaatc 660
tccgccccgt tcgtaagcca tttccgctcg ccgcagtcga acgaccgagc gtagcgagtc 720
agtgagcgag gaagcggaat atatcctgta tcacatattc tgctgacgca ccggtgcagc 780 ctttttctc ctgccacatg aagcacttca ctgacaccct catcagtgcc aacatagtaa 840
gccagtatac actccgctag cgctgaggtc tgcctcgtga agaaggtgtt gctgactcat 900
accaggcctg aatcgcccca tcatccagcc agaaagtgag ggagccacgg ttgatgagag 960
ctttgttgta ggtggaccag ttggtgattt tgaacttttg ctttgccacg gaacggtctg 1020
cgttgtcggg aagatgcgtg atctgatcct tcaactcagc aaaagttcga tttattcaac 1080
aaagccacgt tgtgtctcaa aatctctgat gttacattgc acaagataaa aatatatcat 1140
catgaacaat aaaactgtct gcttacataa acagtaatac aaggggtgtt atgagccata 1200
ttcaacggga aacgtcttgc tcgaggccgc gattaaattc caacatggat gctgatttat 1260
atgggtataa atgggctcgc gataatgtcg ggcaatcagg tgcgacaatc tatcgattgt 1320
atgggaagcc cgatgcgcca gagttgtttc tgaaacatgg caaaggtagc gttgccaatg 1380
atgttacaga tgagatggtc agactaaact ggctgacgga atttatgcct cttccgacca 1440

```
tcaagcattt tatccgtact cctgatgatg catggttact caccactgcg atccccggga   1500
aaacagcatt ccaggtatta gaagaatatc ctgattcagg tgaaaatatt gctgatgcgc   1560
tggcagtgtt cctgcgccgg ttgcattcga ttcctgtttg taattgtcct tttaacagcg   1620
atcgcgtatt tcgtctcgct caggcgcaat cacgaatgaa taacggtttg gttgatgcga   1680
gtgattttga tgacgagcgt aatggctggc ctgttgaaca agtctggaaa gaaatgcata   1740
agcttttgcc attctcaccg gattcagtcg tcactcatgg tgatttctca cttgataacc   1800
ttatttttga cgaggggaaa ttaataggtt gtattgatgt tggacgagtc ggaatcgcag   1860
accgatacca ggatcttgcc atcctatgga actgcctcgg tgagttttct ccttcattac   1920
agaaacggct ttttcaaaaa tatggtattg ataatcctga tatgaataaa ttgcagtttc   1980
atttgatgct cgatgagttt ttctaatcag aattggttaa ttggttgtaa cactggcaga   2040
gcattacgct gacttgacgg gacggcttag ggttaggcgt tttgcgctgc ttcgcgatgt   2100
acgggccaga tatacgcaat gtagtcttat gcaatactct tgtagtcttg caacatggta   2160
acgatgagtt agcaacatgc cttacaagga gagaaaaagc accgtgcatg ccgattggtg   2220
gaagtaaggt ggtacgatcg tgccttatta ggaaggcaac agacgggtct gacatggatt   2280
ggacgaacca ctgaattgcc gcattgcaga gatattgtat ttaagtgcct agctcgatac   2340
ataaacctct ggctaactag agaacccact gcttactggc ttatcgaaat taatacgact   2400
cactataggg agacccagcc accatggtga gcaagggcga ggagctgttc accggggtgg   2460
tgcccatcct ggtcgagctg gacggcgacg taaacggcca caagttcagc gtgtccggcg   2520
agggcgaggg cgatgccacc tacggcaagc tgaccctgaa gttcatctgc accaccggca   2580
agctgcccgt gccctggccc accctcgtga ccaccctgac ctacggcgtg cagtgcttca   2640
gccgctaccc cgaccacatg aagcagcacg acttcttcaa gtccgccatg cccgaaggct   2700
acgtccagga gcgcaccatc ttcttcaagg acgacggcaa ctacaagacc cgcgccgagg   2760
tgaagttcga gggcgacacc ctggtgaacc gcatcgagct gaagggcatc gacttcaagg   2820
aggacggcaa catcctgggg cacaagctgg agtacaacta caacagccac aacgtctata   2880
tcatggccga caagcagaag aacggcatca aggtgaactt caagatccgc cacaacatcg   2940
aggacggcag cgtgcagctc gccgaccact accagcagaa cacccccatc ggcgacggcc   3000
ccgtgctgct gcccgacaac cactacctga gcacccagtc cgccctgagc aaagacccca   3060
acgagaagcg cgatcacatg gtcctgctgg agttcgtgac cgccgccggg atcactctcg   3120
gcatggacga gctgtacaag taaagcggcc gctcgagtct agagggcccg tttaaacccg   3180
ctgatcagcc tcgactgtgc cttctagttg ccagccatct gttgtttgcc cctcccccgt   3240
gccttccttg accctggaag gtgccactcc cactgtcctt tcctaataaa atgaggaaat   3300
tgcatcgcat tgtctgagta ggtgtcattc tattctgggg ggtggggtgg ggcaggacag   3360
caagggggag gattgggaag acaatagcag gcatgctggg gatgcggtgg gctctatggc   3420
ttctgaggcg gaaagaacca gctggggctc taggggggtat ccccacgcgc cctgtagcgg   3480
cgcattaata gggataacag ggtaatatac aaacgaggcc ctttcgtctt taattaacat   3540
catcaataat atacctcaaa cttttggtgc gcgttaatat gcaaatgagg tgtttgaatt   3600
tggggatgcg gggctgtgat tggccgagag acgggcgacc gttaggggcg gggcgggtga   3660
cgttttgatg acgtggccgt gaggcggagc cggtttgcaa gttctcgtgg gaaaagtgac   3720
gtcaaacgag gtgtggtttg aacacggaaa tactcaattt tcccgcgctc tctgacagga   3780
aatgaggtgt ttctgggcgg atgcaagtga aaacgggcca ttttcgcgcg aaaactgaat   3840
```

gaggaagtga aaatctgagt aatttcgcgt ttatggcagg gaggagtatt tgccgagggc 3900
cgagtagact ttgaccgatt acgtgggggt ttcgattacc gtatttttca cctaaatttc 3960
cgcgtacggt gtcaaagtcc ggtgttttta cgtaggtgtc agctgatcgc cagggtattt 4020
aaacctgcgc tctctagtca agaggccact cttgagtgcc agcgagtaga gttttctcct 4080
ccgcgccgcg agtcagatct acactttgaa agatgaggca cctgagagac ctgcccggta 4140
atgttttcct ggctactggg aacgagattc tggaactggt ggtggacgcc atgatgggtg 4200
acgaccctcc tgagcccccct accccatttg aggcgccttc gctgtacgat ttgtatgatc 4260
tggaggtgga tgtgcccgag aacgacccca accttgcatt tctcagtcct aaacagggta 4320
atgggctggg gctgaatcac atgaaggcaa ggtcagattt ttattattat gcacatctag 4380
cttgaaaatt ttccattaag tcaattacag tgaaaaacct cacctggtat tgaatgcttg 4440
ccttgtatgt ctggctattc tgtgttttta ttttaaaatt ataatatcaa aatatttgtg 4500
ttataaaata ttctaactat ggaggccata aacaagaaga ctaaagttct ctcctttcag 4560
ccttctgtac acatttcttc tcaagcactg gtttatgcat gtatactata tgcaaaagtg 4620
atttggtgtt gtcctgcaac gggacggagt tcggctccag cggggaagaa tctgactaga 4680
gtgagtagtg tttgggggtg ggtgggagcc tgcatgaggg gcagaatgac taaaatctgt 4740
gtttttctgt gtgttgcagc agcatgagcg gaagcgcctc ctttgaggga ggggtattca 4800
gcccttatct gacggggcgt ctcccctcct gggctggagt gcgtcagaat gtgatgggat 4860
ccacggtgga cggccggccc gtgcagcccg cgaactcttc aaccctgacc tacgcgaccc 4920
tgagctcctc gtccgtggac gcagctgccg ccgcagctgc tgcttccgcc gccagcgccg 4980
tgcgcggaat ggccctgggt gccggctact acagctctct ggtggccaac tcgagttcca 5040
ccaataatcc cgccagcctg aacgaggaga agctgctgct gctgatggcc cagctcgagg 5100
ccctgaccca gcgcctgggc gagctgaccc agcaggtggc tcagctgcag gcggagacgc 5160
gggccgcggt tgccacggtg aaaaccaaat aaaaaatgaa tcaataaata aacggagacg 5220
gttgttgatt ttaacacaga gtcttgaatc tttatttgat tttcgcgcg cggtaggccc 5280
tggaccaccg gtctcgatca ttgagcaccc ggtggatttt ttccaggacc cggtagaggt 5340
gggcttggat gttgaggtac atgggcatga gcccgtcccg ggggtggagg tagctccatt 5400
gcagggcctc gtgctcgggg gtggtgttgt aaatcaccca gtcatagcag gggcgcaggg 5460
cgtggtgctg cacgatgtcc ttgaggagga gactgatggc cacgggcagc cccttggtgt 5520
aggtgttgac gaacctgttg agctgggagg gatgcatgcg gggggagatg agatgcatct 5580
tggcctggat cttgagattg gcgatgttcc cgcccagatc ccgccggggg ttcatgttgt 5640
gcaggaccac cagcacggtg tatccggtgc acttggggaa tttgtcatgc aacttggaag 5700
ggaaggcatg aaagaatttg gagacgccct tgtgaccgcc caggttttcc atgcactcat 5760
ccatgatgat ggcaatgggc ccgtgggcgg cggcctgggc aaagacgttt cgggggtcgg 5820
acacatcgta gttgtggtcc tgggtgagct cgtcataggc cattttaatg aatttgggac 5880
ggagggtgcc cgattggggg acgaaggtgc cctcgatccc gggggcgtag ttgccctcgc 5940
agatctgcat ctcccaggcc ttgagctcgg agggggggat catgtccacc tgcggggcga 6000
tgaaaaaaac ggtttccggg gcgggggaga tgagctgcgc cgaaagcagg ttccggagca 6060
gctgggactt gccgcagccg gtgggaccgt agatgacccc gatgaccggc tgcaggtggt 6120
agttgaggga gagacagctg ccgtcctcgc ggaggagggg ggccacctcg ttcatcatct 6180
cgcgcacatg catgttctcg cgcacgagtt ccgccaggag gcgctcgccc cccagcgaga 6240
ggagctcttg cagcgaggcg aagtttttca gcggcttgag cccgtcggcc atgggcattt 6300
tggagagggt ctgttgcaag agttccagac ggtcccagag ctcggtgatg tgctctaggg 6360
catctcgatc cagcagacct cctcgtttcg cgggttgggg cgactgcggg agtagggcac 6420
caggcgatgg gcgtccagcg aggccagggt ccggtccttc cagggccgca gggtccgcgt 6480
cagcgtggtc tccgtcacgg tgaaggggtg cgcgccgggc tgggcgcttg cgagggtgcg 6540
cttcaggctc atccggctgg tcgagaaccg ctcccggtcg gcgccctgcg cgtcggccag 6600
gtagcaattg agcatgagtt cgtagttgag cgcctcggcc gcgtggccct tggcgcggag 6660
cttacctttg gaagtgtgtc cgcagacggg acagaggagg gacttgaggg cgtagagctt 6720
gggggcgagg aagacggact cgggggcgta ggcgtccgcg ccgcagctgg cgcagacggt 6780
ctcgcactcc acgagccagg tgaggtcggg ccggtcgggg tcaaaaacga ggtttcctcc 6840
gtgctttttg atgcgtttct tacctctggt ctccatgagc tcgtgtcccc gctgggtgac 6900
aaagaggctg tccgtgtccc cgtagaccga ctttatgggt cggtcctcga gcggggtgcc 6960
gcggtcctcg tcgtagagga accccgccca ctccgagacg aaggcccggg tccaggccag 7020
cacgaaggag gccacgtggg aggggtagcg gtcgttgtcc accagcgggt ccaccttctc 7080
cagggtatgc aagcacatgt ccccctcgtc cacatccagg aaggtgattg gcttgtaagt 7140
gtaggccacg tgaccggggg tcccggccgg gggggtataa aagggggcgg gcccctgctc 7200
gtcctcactg tcttccggat cgctgtccag gagcgccagc tgttggggta ggtattccct 7260
ctcgaaggcg ggcatgacct cggcactcag gttgtcagtt tctagaaacg aggaggattt 7320
gatattgacg gtgccgttgg agacgccttt catgagcccc tcgtccatct ggtcagaaaa 7380
gacgatcttt ttgttgtcga gcttggtggc gaaggagccg tagagggcgt tggagagcag 7440
cttggcgatg gagcgcatgg tctggttctt ttccttgtcg gcgcgctcct tggcggcgat 7500
gttgagctgt acgtactcgc gcgccacgca cttccattcg ggaagacgg tggtgagctc 7560
gtcgggcacg attctgaccc gccagccgcg gttgtgcagg gtgatgaggt ccacgctggt 7620
ggccacctcg ccgcgcaggg gctcgttggt ccagcagagg cgcccgccct tgcgcgagca 7680
gaagggggc agcgggtcca gcatgagctc gtcgggggg tcggcgtcca cggtgaagat 7740
gccgggcagg agctcggggt caaagtagct gatgcaggtg cccagatcgt ccagcgccgc 7800
ttgccagtcg cgcacggcca gcgcgcgctc gtaggggctg aggggcgtgc cccagggcat 7860
ggggtgcgtg agcgcggagg cgtacatgcc gcagatgtcg tagacgtaga ggggctcctc 7920
gaggacgccg atgtaggtgg ggtagcagcg cccccgcgg atgctggcgc gcacgtagtc 7980
gtacagctcg tgcgagggcg cgaggagccc cgtgccgaga ttggagcgct gcggcttttc 8040
ggcgcggtag acgatctggc ggaagatggc gtgggagttg gaggagatgg tgggcctctg 8100
gaagatgttg aagtgggcgt ggggcaggcc gaccgagtcc ctgatgaagt gggcgtagga 8160
gtcctgcagc ttggcgacga gctcggcggt gacgaggacg tccagggcgc agtagtcgag 8220
ggtctcttgg atgatgtcat acttgagctg gcccttctgc ttccacagct cgcggttgag 8280
aaggaactct tcgcggtcct tccagtactc ttcgaggggg aacccgtcct gatcggcacg 8340
gtaagagccc accatgtaga actggttgac ggccttgtag gcgcagcagc ccttctccac 8400
ggggagggcg taagcttgcg cggccttgcg cagggaggtg tgggtgaggg cgaaggtgtc 8460
gcgcaccatg accttgagga actggtgctt gaagtcgagg tcgtcgcagc cgccctgctc 8520
ccagagttgg aagtccgtgc gcttcttgta ggcggggttg ggcaaagcga aagtaacatc 8580

```
gttgaagagg atcttgcccg cgcggggcat gaagttgcga gtgatgcgga aaggctgggg   8640
cacctcggcc cggttgttga tgacctgggc ggcgaggacg atctcgtcga agccgttgat   8700
gttgtgcccg acgatgtaga gttccacgaa tcgcgggcgg cccttgacgt ggggcagctt   8760
cttgagctcg tcgtaggtga gctcggcggg gtcgctgagg ccgtgctgct cgagggccca   8820
gtcggcgacg tgggggttgg cgctgaggaa ggaagtccag agatccacgg ccagggcggt   8880
ctgcaagcgg tcccggtact gacggaactg ctggcccacg gccatttttt cgggggtgac   8940
gcagtagaag gtgcgggggt cgccgtgcca gcggtcccac ttgagctgga gggcgaggtc   9000
gtgggcgagc tcgacgagcg gcgggtcccc ggagagtttc atgaccagca tgaaggggac   9060
gagctgcttg ccgaaggacc ccatccaggt gtaggtttcc acatcgtagg tgaggaagag   9120
cctttcggtg cgaggatgcg agccgatggg gaagaactgg atctcctgcc accagttgga   9180
ggaatggctg ttgatgtgat ggaagtagaa atgccgacgg cgcgccgagc actcgtgctt   9240
gtgtttatac aagcgtccgc agtgctcgca acgctgcacg ggatgcacgt gctgcacgag   9300
ctgtacctga gttcctttga cgaggaattt cagtgggcag tggagcgctg gcggctgcat   9360
ctggtgttgt actacgtcct ggccatcggc gtggccatcg tctgcctcga tggtggtcat   9420
gctgacgagg ccgcgcggga ggcaggtcca gacctcggct cggacgggtc ggagagcgag   9480
gacgagggcg cgcaggccgg agctgtccag ggtcctgaga cgctgcggag tcaggtcagt   9540
gggcagcggc ggcgcgcggt tgacttgcag gagcttttcc agggcgcgcg ggaggtccag   9600
atggtacttg atctccacgg cgccgttggt ggcaacgtcc acggcttgca gggtgccgtg   9660
cccctggggc gccaccaccg tgccccgttt ctttttgggc gctggcggcg gcggctccat   9720
gcttagaatc ggcggcgagg acgcgcgccg ggcggcaggg gcggctcggg gcccggaggc   9780
aggggcggca ggggcacgtc ggcgccgcgc gcgggcaggt tctggtactg cgcccggaga   9840
agactggcgt gagcgacgac gcgacggttg acgtcctgga tctgacgcct ctgggtgaag   9900
gccacgggac ccgtgagttt gaacctgaaa gagagttcga cagaatcaat ctcggtatcg   9960
ttgacggcag cctgccgcag gatctcttgc acgtcgcccg agttgtcctg gtaggcgatc  10020
tcggtcatga actgctcgat ctcctcctcc tgaaggtctc cgcggccggc gcgctcgacg  10080
gtggccgcga ggtcgttgga gatgcggccc atgagctgcg agaaggcgtt catgccggcc  10140
tcgttccaga cgcggctgta gaccacggct ccgtcggggt cgcgcgcgcg catgaccacc  10200
tgggcgaggt tgatctccac gtggcgcgtg aagaccgcgt agttgcagag gcgctggtag  10260
aggtagttga gcgtggtggc gatgtgctcg gtgacgaaga agtacatgat ccagcggcgg  10320
agcggcatct cgctgacgtc gcccagggct tccaagcgct ccatggcctc gtagaagtcc  10380
acggcgaagt tgaaaaactg ggagttgcgc gccgagacgg tcaactcctc ctccagaaga  10440
cggatgagct cggcgatggt ggcgcgcacc tcgcgctcga aggccccggg gggctcctct  10500
tcttccatct cctcctcctc ttcctcctcc tccactaaca tctcttctac ttcctcctca  10560
ggaggcggcg gcgggggagg ggccctgcgt cgccggcggc gcacgggcag acggtcgatg  10620
aagcgctcga tggtctcccc gcgccggcga cgcatggtct cggtgacggc gcgcccgtcc  10680
tcgcggggcc gcagcgtgaa gacgccgccg cgcatctcca ggtggccgcc ggggggggtct 10740
ccgttgggca gggagagggc gctgacgatg catcttatca attggcccgt agggactccg  10800
cgcaaggacc tgagcgtctc gagatccacg ggatccgaaa accgctgaac gaaggcttcg  10860
agccagtcgc agtcgcaagg taggctgagc ccggtttctt gttcttcggg tatttggtcg  10920
```

ggaggcgggc gggcgatgct gctggtgatg aagttgaagt aggcggtcct gagacggcgg 10980
atggtggcga ggagcaccag gtccttgggc ccggcttgct ggatgcgcag acggtcggcc 11040
atgccccagg cgtggtcctg acacctggcg aggtccttgt agtagtcctg catgagccgc 11100
tccacgggca cctcctcctc gcccgcgcgg ccgtgcatgc gcgtgagccc gaacccgcgc 11160
tggggctgga cgagcgccag gtcggcgacg acgcgctcgg cgaggatggc ctgctggatc 11220
tgggtgaggg tggtctggaa gtcgtcgaag tcgacgaagc ggtggtaggc tccggtgttg 11280
atggtgtagg agcagttggc catgacggac cagttgacgg tctggtggcc ggggcgcacg 11340
agctcgtggt acttgaggcg cgagtaggcg cgcgtgtcga agatgtagtc gttgcaggtg 11400
cgcacgaggt actggtatcc gacgaggaag tgcggcggcg gctggcggta gagcggccat 11460
cgctcggtgg cgggggcgcc gggcgcgagg tcctcgagca tgaggcggtg gtagccgtag 11520
atgtacctgg acatccaggt gatgccggcg gcggtggtgg aggcgcgcgg gaactcgcgg 11580
acgcggttcc agatgttgcg cagcggcagg aagtagttca tggtggccgc ggtctggccc 11640
gtgaggcgcg cgcagtcgtg gatgctctag acatacgggc aaaaacgaaa gcggtcagcg 11700
gctcgactcc gtggcctgga ggctaagcga acgggttggg ctgcgcgtgt accccggttc 11760
gagtccctgc tcgaatcagg ctggagccgc agctaacgtg gtactggcac tcccgtctcg 11820
acccaagcct gctaacgaaa cctccaggat acggaggcgg gtcgttttgg caattttcgt 11880
caggccggaa atgaaactag taagcgcgga aagcggccgc ccgcgatggc tcgctgccgt 11940
agtctggaga aagaatcgcc agggttgcgt tgcggtgtgc cccggttcga gcctcggcgc 12000
tcgtgccggc cggattccgc ggctaacgtg ggcgtggctg ccccgtcgtt tccaagaccc 12060
cttagccagc cgacttctcc agttacggag cgagcccctc tttttttttt ttcttgtgtt 12120
tttgccagat gcatcccgta ctgcggcaga tgcgccccca ccctccacca caaccgcccc 12180
taccgcagca gcagcaacag ccggcgcttc tgcccccgcc ccagcagcag cagccagcca 12240
ctaccgcggc ggccgccgtg agcggagccg gcgttcagta tgacctggcc ttggaagagg 12300
gcgaggggct ggcgcggctg gggcgtcgt cgccggagcg gcacccgcgc gtgcagatga 12360
aaagggacgc tcgcgaggcc tacgtgccca agcagaacct gttcagagac aggagcggcg 12420
aggagcccga ggagatgcgc gcctcccgct tccacgcggg gcgggagctg cggcgcggcc 12480
tggaccgaaa gcgggtgctg agggacgagg atttcgaggc ggacgagctg acggggatca 12540
gccccgcgcg cgcgcacgtg gccgcggcca acctggtcac ggcgtacgag cagaccgtga 12600
aggaggagag caacttccaa aaatccttca acaaccacgt gcgcacgctg atcgcgcgcg 12660
aggaggtgac cctgggcctg atgcacctgt gggacctgct ggaggccatc gtgcagaacc 12720
ccacgagcaa gccgctgacg gcgcagctgt ttctggtggt gcagcacagt cgggacaacg 12780
agacgttcag ggaggcgctg ctgaatatca ccgagcccga gggccgctgg ctcctggacc 12840
tggtgaacat tctgcagagc atcgtggtgc aggagcgcgg gctgccgctg tccgagaagc 12900
tggcggccat caacttctcg gtgctgagcc tgggcaagta ctacgctagg aagatctaca 12960
agaccccgta cgtgcccata gacaaggagg tgaagatcga cgggttttac atgcgcatga 13020
ccctgaaagt gctgaccctg agcgacgatc tgggggtgta ccgcaacgac aggatgcacc 13080
gcgcggtgag cgccagccgc cggcgcgagc tgagcgacca ggagctgatg cacagcctgc 13140
agcgggccct gaccggggcc gggaccgagg gggagagcta ctttgacatg ggcgcggacc 13200
tgcgctggca gcccagccgc cgggccttgg aagctgccgg cggttccccc tacgtggagg 13260
aggtggacga tgaggaggag gagggcgagt acctggaaga ctgatggcgc gaccgtattt 13320
ttgctagatg cagcaacagc caccgccgcc tcctgatccc gcgatgcggg cggcgctgca 13380
gagccagccg tccggcatta actcctcgga cgattggacc caggccatgc aacgcatcat 13440
ggcgctgacg acccgcaatc ccgaagcctt tagacagcag cctcaggcca accggctctc 13500
ggccatcctg gaggccgtgg tgccctcgcg ctcgaacccc acgcacgaga aggtgctggc 13560
catcgtgaac gcgctggtgg agaacaaggc catccgcggc gacgaggccg ggctggtgta 13620
caacgcgctg ctggagcgcg tggcccgcta caacagcacc aacgtgcaga cgaacctgga 13680
ccgcatggtg accgacgtgc gcgaggcggt gtcgcagcgc gagcggttcc accgcgagtc 13740
gaacctgggc tccatggtgg cgctgaacgc cttcctgagc acgcagcccg ccaacgtgcc 13800
ccggggccag gaggactaca ccaacttcat cagcgcgctg cggctgatgg tggccgaggt 13860
gccccagagc gaggtgtacc agtcggggcc ggactacttc ttccagacca gtcgccaggg 13920
cttgcagacc gtgaacctga gccaggcttt caagaacttg cagggactgt ggggcgtgca 13980
ggccccggtc ggggaccgcg cgacggtgtc gagcctgctg acgccgaact cgcgcctgct 14040
gctgctgctg gtggcgccct tcacggacag cggcagcgtg agccgcgact cgtacctggg 14100
ctacctgctt aacctgtacc gcgaggccat cgggcaggcg cacgtggacg agcagaccta 14160
ccaggagatc acccacgtga gccgcgcgct gggccaggag gacccgggca acctggaggc 14220
caccctgaac ttcctgctga ccaaccggtc gcagaagatc ccgccccagt acgcgctgag 14280
caccgaggag gagcgcatcc tgcgctacgt gcagcagagc gtggggctgt tcctgatgca 14340
ggagggggcc acgcccagcg ccgcgctcga catgaccgcg cgcaacatgg agcccagcat 14400
gtacgcccgc aaccgcccgt tcatcaataa gctgatggac tacttgcatc gggcggccgc 14460
catgaactcg gactacttta ccaacgccat cttgaacccg cattggctcc cgccgcccgg 14520
gttctacacg ggcgagtacg acatgcccga ccccaacgac gggttcctgt gggacgacgt 14580
ggacagcagc gtgttctcgc cgcgccccac cgccaccacc gtgtggaaga aagagggcgg 14640
ggaccggcgg ccgtcctcgg cgctgtccgg tcgcgcgggt gctgccgcgg cggtgcccga 14700
ggccgccagc cccttcccga gcctgccctt ttcgctgaac agcgtgcgca gcagcgagct 14760
gggtcggctg acgcggccgc gcctgctggg cgaggaggag tacctgaacg actccttgtt 14820
gaggcccgag cgcgagaaga acttccccaa taacgggata gagagcctgg tggacaagat 14880
gagccgctgg aagacgtacg cgcacgagca cagggacgag ccccgagcta gcagcagcgc 14940
cacccgtaga cgccagcggc acgacaggca gcggggactg gtgtgggacg atgaggattc 15000
cgccgacgac agcagcgtgt tggacttggg tgggagtggt ggtaacccgt tcgctcactt 15060
gcgcccccgt atcgggcgcc tgatgtaaga atctgaaaaa ataaaaaacg gtactcacca 15120
aggccatggc gaccagcgtg cgttcttctc tgttgtttgt agtagtatga tgaggcgcgt 15180
gtacccggag ggtcctcctc cctcgtacga gagcgtgatg cagcaggcgg tggcggcggc 15240
gatgcagccc ccgctggagg cgccttacgt gcccccgcgg tacctggcgc ctacggaggg 15300
gcggaacagc attcgttact cggagctggc acccttgtac gataccaccc ggttgtacct 15360
ggtggacaac aagtcggcgg acatcgcctc gctgaactac cagaacgacc acagcaactt 15420
cctgaccacc gtggtgcaga acaacgattt cacccccacg gaggccagca cccagaccat 15480
caactttgac gagcgctcgc ggtggggcgg ccagctgaaa accatcatgc acaccaacat 15540
gcccaacgtg aacgagttca tgtacagcaa caagttcaag gcgcgggtga tggtctcgcg 15600
caagaccccc aacggggtga cggtagggga tgattatgat ggtagtcagg acgagctgac 15660
ctacgagtgg gtggagtttg agctgcccga gggcaacttc tcggtgacca tgaccatcga 15720
tctgatgaac aacgccatca tcgacaacta cttggcggtg gggcggcaga acggggtgct 15780
ggagagcgac atcggcgtga agttcgacac gcgcaacttc cggctgggct gggaccccgt 15840
gaccgagctg gtgatgccgg gcgtgtacac caacgaggcc ttccaccccg acatcgtcct 15900
gctgcccggc tgcggcgtgg acttcaccga gagccgcctc agcaacctgc tgggcatccg 15960
caagcggcag cccttccagg agggcttcca gatcctgtac gaggacctgg aggggggcaa 16020
catccccgcg ctgctggacg tggacgccta tgagaaaagc aaggaggata gcgccgccgc 16080
ggcgaccgca gccgtggcca ccgcctctac cgaggtgcgg ggcgataatt ttactagcgc 16140
cgcagcagtg gccgaggcgg ctgaaaccga aagtaagata gtgatccagc cggtggagaa 16200
ggacagcaag gacaggagct acaacgtgct cgcggacaag aaaaacaccg cctaccgcag 16260
ctggtacctg gcctacaact acggcgaccc cgagaagggc gtgcgctcct ggacgctgct 16320
caccacctcg gacgtcacct gcggcgtgga gcaagtctac tggtcgctgc ccgacatgat 16380
gcaagacccg gtcaccttcc gctccacgcg tcaagttagc aactacccgg tggtgggcgc 16440
cgagctcctg cccgtctact ccaagagctt cttcaacgag caggccgtct actcgcagca 16500
gctgcgcgcc ttcacctcgc tcacgcacgt tttcaaccgc ttccccgaga accagatcct 16560
cgttcgcccg cccgcgccca ccattaccac cgtcagtgaa aacgttcctg ctctcacaga 16620
tcacgggacc ctgccgctgc gcagcagtat ccggggagtc cagcgcgtga ccgtcactga 16680
cgccagacgc cgcacctgcc cctacgtcta caaggccctg ggcgtagtcg cgccgcgcgt 16740
cctctcgagc cgcaccttct aaaaaatgtc cattctcatc tcgcccagta ataacaccgg 16800
ttggggcctg cgcgcgccca gcaagatgta cggaggcgct cgccaacgct ccacacaaca 16860
ccccgtgcgc gtgcgcgggc acttccgcgc tccctggggc gccctcaagg gccgcgtgcg 16920
ctcgcgcacc accgtcgacg acgtgatcga ccaggtggtg gccgacgcgc gcaactacac 16980
gcccgccgcc gcgcccgtct ccaccgtgga cgccgtcatc gacagcgtgg tggccgacgc 17040
gcgccggtac gcccgcgcca agagccggcg gcggcgcatc gcccggcggc accggagcac 17100
ccccgccatg cgcgcggcgc gagccttgct gcgcagggcc aggcgcacgg gacgcagggc 17160
catgctcagg gcggccagac gcgcggcctc cggcagcagc agcgccggca gaacccgcag 17220
acgcgcggcc acggcggcgg cggcggccat cgccagcatg tcccgcccgc ggcgcggcaa 17280
cgtgtactgg gtgcgcgacg ccgccaccgg tgtgcgcgtg cccgtgcgca cccgcccccc 17340
tcgcacttga agatgctgac ttcgcgatgt tgatgtgtcc cagcggcgag gaggatgtcc 17400
aagcgcaaat acaaggaaga gatgctccag gtcatcgcgc ctgagatcta cggccccgcg 17460
gcggcggtga aggaggaaag aaagccccgc aaactgaagc gggtcaaaaa ggacaaaaag 17520
gaggaggaag atgacggact ggtggagttt gtgcgcgagt tcgccccccg gcggcgcgtg 17580
cagtggcgcg ggcggaaagt gaaaccggtg ctgcggcccg gcaccacggt ggtcttcacg 17640
cccggcgagc gttccggctc cgcctccaag cgctcctacg acgaggtgta cggggacgag 17700
gacatcctcg agcaggcggt cgagcgtctg ggcgagtttg cttacggcaa gcgcagccgc 17760
cccgcgccct tgaaagagga ggcggtgtcc atcccgctgg accacggcaa ccccacgccg 17820
agcctgaagc cggtgaccct gcagcaggtg ctaccgagcg cggcgccgcg ccggggcttc 17880
aagcgcgagg gcggcgagga tctgtacccg accatgcagc tgatggtgcc caagcgccag 17940
aagctggagg acgtgctgga gcacatgaag gtggaccccg aggtgcagcc cgaggtcaag 18000
gtgcggccca tcaagcaggt ggctccgggc ctgggcgtgc agaccgtgga catcaagatc 18060
cccacggagc ccatggaaac gcagaccgag cccgtgaagc ccagcaccag caccatggag 18120
gtgcagacgg atccctggat gccagcggct tccaccacca ccacccgccg aagacgcaag 18180
tacggcgcga ccagcctgct gatgcccaac tacgcgctgc atccttccat catccccacg 18240
ccgggctacc gcggcacgcg cttctaccgc ggctacagca gccgccgcaa gaccaccacc 18300
cgccgccgcc gtcgtcgcac ccgccgcagc agcaccgcga cttccgccgc cgccttggtg 18360
cggagagtgt accgcagcgg gcgcgagcct ctgaccctgc cgcgcgcgcg ctaccacccg 18420
agcatcgcca tttaactctg ccgtcgcctc cttgcagata tggccctcac atgccgcctc 18480
cgcgtcccca ttacgggcta ccgaggaaga aagccgcgcc gtagaaggct gacggggaac 18540
gggctgcgtc gccatcacca ccggcggcgg cgcgccatca gcaagcggtt gggggaggc 18600
ttcctgcccg cgctgatccc catcatcgcc gcggcgatcg gggcgatccc cggcatagct 18660
tccgtggcgg tgcaggcctc tcagcgccac tgagacacag cttggaaaat ttgtaataaa 18720
aaatggactg acgctcctgg tcctgtgatg tgtgttttta gatggaagac atcaattttt 18780
cgtccctggc accgcgacac ggcacgcggc cgtttatggg cacctggagc gacatcggca 18840
acagccaact gaacgggggc gccttcaatt ggagcagtct ctggagcggg cttaagaatt 18900
tcgggtccac gctcaaaacc tatggcaaca aggcgtggaa cagcagcaca gggcaggcgc 18960
tgagggaaaa gctgaaagag cagaacttcc agcagaaggt ggtcgatggc ctggcctcgg 19020
gcatcaacgg ggtggtggac ctggccaacc aggccgtgca gaaacagatc aacagccgcc 19080
tggacgcggt cccgcccgcg ggtccgtgg agatgcccca ggtggaggag gagctgcctc 19140
ccctggacaa gcgcggcgac aagcgaccgc gtcccgacgc ggaggagacg ctgctgacgc 19200
acacggacga gccgcccccg tacgaggagg cggtgaaact gggtctgccc accacgcggc 19260
ccgtggcgcc tctggccacc ggggtgctga aacccagcag cagcagcagc cagcccgcga 19320
ccctggactt gcctccgcct gcttcccgcc cctccacagt ggctaagccc ctgccgccgg 19380
tggccgtcgc gtcgcgcgcc ccccgaggcc gcccccaggc gaactggcag agcactctga 19440
acagcatcgt gggtctggga gtgcagagtg tgaagcgccg ccgctgctat taaaagacac 19500
tgtagcgctt aacttgcttg tctgtgtgta tatgtatgtc cgccgaccag aaggaggagg 19560
aagaggcgcg tcgccgagtt gcaagatggc caccccatcg atgctgcccc agtgggcgta 19620
catgcacatc gccggacagg acgcttcgga gtacctgagt ccgggtctgg tgcagttcgc 19680
ccgcgccaca gacacctact tcagtctggg gaacaagttt aggaacccca cggtggcgcc 19740
cacgcacgat gtgaccaccg accgcagcca gcggctgacg ctgcgcttcg tgcccgtgga 19800
ccgcgaggac aacacctact cgtacaaagt gcgctacacg ctggccgtgg gcgacaaccg 19860
cgtgctggac atggccagca cctactttga catccgcggc gtgctggacc ggggccccag 19920
cttcaaaccc tactccggca ccgcctacaa cagtctggct cccaagggag cgcccaacac 19980
ctcacagtgg ataaccaaag acaatggaac tgataagaca tacagttttg gaaatgctcc 20040
agtcagagga ttggacatta cagaagaggg tctccaaata ggaaccgatg agtcaggggg 20100
tgaaagcaag aaaatttttg cagacaaaac ctatcagcct gaacctcagc ttggagatga 20160
ggaatggcat gatactattg gagctgaaga caagtatgga ggcagagcgc ttaaacctgc 20220
caccaacatg aaaccctgct atgggtcttt cgccaagcca actaatgcta agggaggtca 20280
ggctaaaagc agaaccaagg acgatggcac tactgagcct gatattgaca tggccttctt 20340
tgacgatcgc agtcagcaag ctagtttcag tccagaactt gttttgtata ctgagaatgt 20400
cgatctggac accccggata cccacattat ttacaaacct ggcactgatg aaacaagttc 20460
ttctttcaac ttgggtcagc agtccatgcc caacagaccc aactacattg ggttcagaga 20520
caactttatc ggtctcatgt actacaacag cactggcaat atgggtgtgc tggctggaca 20580
ggcctcccag ctgaatgctg tggtggactt gcaggacaga aacactgaac tgtcctacca 20640
gctcttgctt gactctctgg gtgacagaac taggtatttc agtatgtgga atcaggcggt 20700
ggacagctac gaccccgatg tgcgcattat tgaaaatcac ggtgtggagg atgaactccc 20760
caactattgc ttccctttga atggtgtggg ctttacagat acattccagg gaattaaggt 20820
taaaactacc aataacggaa cagcaaatgc tacagagtgg gaatctgata cctctgtcaa 20880
taatgctaat gagattgcca agggcaatcc tttcgccatg gagatcaaca tccaggccaa 20940
cctgtggcgg aacttcctct acgcgaacgt ggcgctgtac ctgcccgact cctacaagta 21000
cacgccggcc aacatcacgc tgcccaccaa caccaacacc tacgattaca tgaacggccg 21060
cgtggtggcg ccctcgctgg tggacgccta catcaacatc ggggcgcgct ggtcgctgga 21120
ccccatggac aacgtcaacc ccttcaacca ccaccgcaac gcgggcctgc gctaccgctc 21180
catgctcctg ggcaacgggc gctacgtgcc cttccacatc caggtgcccc aaaagttttt 21240
cgccatcaag agcctcctgc tcctgcccgg gtcctacacc tacgagtgga acttccgcaa 21300
ggacgtcaac atgatcctgc agagctccct cggcaacgac ctgcgcacgg acggggcctc 21360
catcgccttc accagcatca acctctacgc caccttcttc cccatggcgc acaacaccgc 21420
ctccacgctc gaggccatgc tgcgcaacga caccaacgac cagtccttca acgactacct 21480
ctcggcggcc aacatgctct accccatccc ggccaacgcc accaacgtgc ccatctccat 21540
cccctcgcgc aactgggccg ccttccgcgg atggtccttc acgcgcctca agacccgcga 21600
gacgccctcg ctcggctccg ggttcgaccc ctacttcgtc tactcgggct ccatccccta 21660
ccttgacggc accttctacc tcaaccacac cttcaagaag gtctccatca ccttcgactc 21720
ctccgtcagc tggcccggca acgaccgcct cctgacgccc aacgagttcg aaatcaagcg 21780
caccgtcgac ggagaggggt acaacgtggc ccagtgcaac atgaccaagg actggttcct 21840
ggtccagatg ctggcccact acaacatcgg ctaccagggc ttctacgtgc ccgagggcta 21900
caaggaccgc atgtactcct tcttccgcaa cttccagccc atgagccgcc aggtcgtgga 21960
cgaggtcaac tacaaggact accaggccgt caccctggcc taccagcaca acaactcggg 22020
cttcgtcggc tacctcgcgc ccaccatgcg ccagggccag ccctaccccg ccaactaccc 22080
ctacccgctc atcggcaaga gcgccgtcgc cagcgtcacc cagaaaaagt tcctctgcga 22140
ccgggtcatg tggcgcatcc ccttctccag caacttcatg tccatgggcg cgctcaccga 22200
cctcggccag aacatgctct acgccaactc cgcccacgcg ctagacatga atttcgaagt 22260
cgaccccatg gatgagtcca cccttctcta tgttgtcttc gaagtcttcg acgtcgtccg 22320
agtgcaccag ccccaccgcg gcgtcatcga ggccgtctac ctgcgcacgc ccttctcggc 22380
cggcaacgcc accacctaag cctcttgctt cttgcaagat atggcctgtg cgggctccgg 22440
cgagcaggag ctcagggcca tcctccgcga cctgggctgc gggccctgct tcctgggcac 22500
cttcgacaag cgcttcccgg gattcatggc cccgcacaag ctggcctgcg ccattgtcaa 22560
cacggccggc cgcgagaccg gggcgagca ctggctggcc ttcgcctgga acccgcgctc 22620
ccacacctgc tacctcttcg accccttgg gttctcggac gagcgcctca agcagatcta 22680
ccagttcgag tacgagggcc tgctgcgtcg cagcgccctg gccaccgagg accgctgcgt 22740
caccctggaa aagtccaccc agaccgtgca gggtccgcgc tcggccgcct gcgggctctt 22800
ctgctgcatg ttcctgcacg ccttcgtgca ctggcccgac cgccccatgg acaagaaccc 22860
caccatgaac ttgctgacgg gggtgcccaa cggcatgctc cagtcgcccc aggtggaacc 22920
caccctgcgc cgcaaccagg aggcgctcta ccgcttcctc aacgcccact ccgcctactt 22980
tcgatcccac cgcgcgcgca tcgagaaggc caccgccttc gaccgcatga atcaagacat 23040
gtaaaccgtg tgtgtatgtg aatgctttat tcataataaa cagcacatgt ttatgccacc 23100
ttctctgagg ctctgacttt atttagaaat cgaaggggtt ctgccggctc tcggcgtgcc 23160
ccgcgggcag ggatacgttg cggaactggt acttgggcag ccacttgaac tcggggatca 23220
gcagcttggg cacggggagg tcggggaacg agtcgctcca cagcttgcgc gtgagttgca 23280
gggcgcccag caggtcgggc gcggagatct tgaaatcgca gttgggaccc gcgttctgcg 23340
cgcgagagtt gcggtacacg gggttgcagc actggaacac catcagggcc gggtgcttca 23400
cgctcgccag caccgtcgcg tcggtgatgc cctccacgtc cagatcctcg gcgttggcca 23460
tcccgaaggg ggtcatcttg caggtctgcc gccccatgct gggcacgcag ccgggcttgt 23520
ggttgcaatc gcagtgcagg gggatcagca tcatctgggc ctgctcggag ctcatgcccg 23580
ggtacatggc cttcatgaaa gcctccagct ggcggaaggc ctgctgcgcc ttgccgccct 23640
cggtgaagaa gaccccgcag gacttgctag agaactggtt ggtggcgcag ccggcgtcgt 23700
gcacgcagca gcgcgcgtcg ttgttggcca gctgcaccac gctgcgcccc cagcggttct 23760
gggtgatctt ggcccggtcg ggtttctcct tcagcgcgcg ctgcccgttc tcgctcgcca 23820
catccatctc gatcgtgtgc tccttctgga tcatcacggt cccgtgcagg caccgcagct 23880
tgccctcggc ctcggtgcag ccgtgcagcc acagcgcgca gccggtgctc tcccagttct 23940
tgtgggcgat ctgggagtgc gagtgcacga agccctgcag gaagcggccc atcatcgcgg 24000
tcagggtctt gttgctggtg aaggtcagcg ggatgccgcg gtgctcctcg ttcacataca 24060
ggtggcagat gcggcggtac acctcgccct gctcgggcat cagctggaag gcggacttca 24120
ggtcgctctc cacgcggtac cggtccatca gcagcgtcat cacttccatg cccttctccc 24180
aggccgaaac gatcggcagg ctcagggggt tcttcaccgc cattgtcatc ttagtcgccg 24240
ccgccgaagt caggggggtcg ttctcgtcca gggtctcaaa cactcgcttg ccgtccttct 24300
cggtgatgcg cacgggggggg aaggcgaagc ccacggccgc cagctcctcc tcggcctgcc 24360
tttcgtcctc gctgtcctgg ctgatgtctt gcaaaggcac atgcttggtc ttgcggggtt 24420
tctttttggg cggcagaggc ggcggcggag acgtgctggg cgagcgcgag ttctcgctca 24480
ccacgactat ttcttctcct tggccgtcgt ccgagaccac gcggcggtag gcatgcctct 24540
tctggggcag aggcggaggc gacgggctct cgcggttcgg cgggcggctg gcagagcccc 24600
ttccgcgttc gggggtgcgc tcctggcggc gctgctctga ctgacttcct ccgcggccgg 24660
ccattgtgtt ctcctaggga gcaagcatgg agactcagcc atcgtcgcca acatcgccat 24720
ctgcccccgc cgccgccgac gagaaccagc agaatgaaag cttaaccgcc ccgccgccca 24780
gccccacctc cgacgcggcc ccagacatgc aagagatgga ggaatccatc gagattgacc 24840
tgggctacgt gacgcccgcg gagcacgagg aggagctggc agcgcgcttt tcagccccgg 24900
aagagaacca ccaagagcag ccagagcagg aagcagagag cgagcagcag caggctgggc 24960
tcgagcatgg cgactacctg agcggggcag aggacgtgct catcaagcat ctggcccgcc 25020
aatgcatcat cgtcaaggac gcgctgctcg accgcgccga ggtgcccctc agcgtggcgg 25080
agctcagccg cgcctacgag cgcaacctct tctcgccgcg cgtgccccc aagcgccagc 25140 ccaacggcac ctgcgagccc aacccgcgcc tcaacttcta cccggtcttc gcggtgcccg 25200
aggccctggc cacctaccac ctctttttca agaaccaaag gatccccgtc tcctgccgcg 25260
ccaaccgcac ccgcgccgac gccctgctca acctgggccc cggcgcccgc ctacctgata 25320
tcgcctcctt ggaagaggtt cccaagatct tcgagggtct gggcagcgac gagactcggg 25380
ccgcgaacgc tctgcaagga agcggagagg agcatgagca ccacagcgcc ctggtggagt 25440
tggaaggcga caacgcgcgc ctggcggtgc tcaagcgcac ggtcgagctg acccacttcg 25500
cctacccggc gctcaacctg ccccccaagg tcatgagcgc cgtcatggac caggtgctca 25560
tcaagcgcgc ctcgcccctc tcggaggagg agatgcagga ccccgagagc tcggacgagg 25620
gcaagcccgt ggtcagcgac gagcagctgg cgcgctggct gggagcgagt agcaccccc 25680
agagcctgga agagcggcgc aagctcatga tggccgtggt cctggtgacc gtggagctgg 25740
agtgtctgcg ccgcttcttc gccgacgcgg agaccctgcg caaggtcgag gagaacctgc 25800
actacctctt caggcacggg ttcgtgcgcc aggcctgcaa gatctccaac gtggagctga 25860
ccaacctggt ctcctacatg ggcatcctgc acgagaaccg cctggggcag aacgtgctgc 25920
acaccaccct gcgcggggag gcccgccgcg actacatccg cgactgcgtc tacctgtacc 25980
tctgccacac ctggcagacg ggcatgggcg tgtggcagca gtgcctggag gagcagaacc 26040
tgaaagagct ctgcaagctc ctgcagaaga acctcaaggc cctgtggacc gggttcgacg 26100
agcgcaccac cgcctcggac ctggccgacc tcatcttccc cgagcgcctg cggctgacgc 26160
tgcgcaacgg gctgcccgac tttatgagcc aaagcatgtt gcaaaacttt cgctctttca 26220
tcctcgaacg ctccgggatc ctgcccgcca cctgctccgc gctgccctcg gacttcgtgc 26280
cgctgacctt ccgcgagtgc cccccgccgc tctggagcca ctgctacctg ctgcgcctgg 26340
ccaactacct ggcctaccac tcggacgtga tcgaggacgt cagcggcgag ggcctgctcg 26400
agtgccactg ccgctgcaac ctctgcacgc cgcaccgctc cctggcctgc aacccccagc 26460
tgctgagcga gacccagatc atcggcacct tcgagttgca aggccccggc gacagcgagg 26520
gcaagggggg tctcaaactc accccggggc tgtggacctc ggcctacttg cgcaagttcg 26580
tgcccgagga ctaccatccc ttcgagatca ggttctacga ggaccaatcc cagccgccca 26640
aggccaagct gtcggcctgc gtcatcaccc agggggccat cctggcccaa ttgcaagcca 26700
tccagaaatc ccgccaagaa tttctgctga aaaagggcca cggggtctac ttggaccccc 26760
agaccggaga ggagctcaac cccagcttcc cccaggatgc cccgaggaag cagcaagaag 26820
ctgaaagtgg agctgccgcc gccggaggat ttggaggaag actgggagag cagtcaggca 26880
gaggagatgg aagactggga cagcactcag gcagaggagg acagcctgca agacagtctg 26940
gaggaggaag acgaggtgga ggaggaggca gaggaagaag cagccgccgc cagaccgtcg 27000
tcctcggcgg aggagaaagc aagcagcacg gataccatct ccgctccggg tcggggtcgc 27060
ggcggccggg cccacagtag gtgggacgag accgggcgct tcccgaaccc caccacccag 27120
accggtaaga aggagcggca gggatacaag tcctggcggg ggcacaaaaa cgccatcgtc 27180
tcctgcttgc aagcctgcgg gggcaacatc tccttcaccc ggcgctacct gctcttccac 27240
cgcggggtga acttcccccg caacatcttg cattactacc gtcacctcca cagcccctac 27300
tactgtttcc aagaagaggc agaaacccag cagcagcagc agaaaaccag cgacagctag 27360
aaaatccaca gcggcggcgg caggtggact gaggatcgcg gcgaacgagc cagcgcagac 27420
ccgggagctg aggaaccgga tctttcccac cctctatgcc atcttccagc agagtcgggg 27480
gcaggagcag gaactgaaag tcaagaaccg ttctctgcgc tcgctcaccc gcagttgtct 27540
gtatcacaag agcgaagacc aacttcagcg cactctcgag gacgccgagg ctctcttcaa 27600
caagtactgc gcgctcactc ttaaagagta gcccgcgccc gcccacacac ggaaaaaggc 27660
gggaattacg tcaccacctg cgcccttcgc ccgaccatca tgagcaaaga gattcccacg 27720
ccttacatgt ggagctacca gccccagatg ggcctggccg ccggcgccgc ccaggactac 27780
tccacccgca tgaactggct cagtgccggg cccgcgatga tctcacgggt gaatgacatc 27840
cgcgcccacc gaaaccagat actcctagaa cagtcagcga tcaccaccac gccccgccat 27900
caccttaatc cgcgtaattg gcccgccgcc ctggtgtacc aggaaattcc ccagcccacg 27960
accgtactac ttccgcgaga cgcccaggcc gaagtccagc tgactaactc aggtgtccag 28020
ctggccggcg gcgccgccct gtgtcgtcac cgccccgctc agggtataaa gcggctggtg 28080
atccgaggca gaggcacaca gctcaacgac gaggtggtga gctcttcgct gggtctgcga 28140
cctgacggag tcttccaact cgccggatcg gggagatctt ccttcacgcc tcgtcaggcc 28200
gtcctgactt tggagagttc gtcctcgcag ccccgctcgg gcggcatcgg cactctccag 28260
ttcgtggagg agttcactcc ctcggtctac ttcaacccct tctccggctc cccggccac 28320
tacccggacg agttcatccc gaacttcgac gccatcagcg agtcggtgga cggctacgat 28380
tgatcacccc cttatccagt gaaataaaga tcatattgat gatgatttaa ataaaaaaaa 28440
aaaaaaaata atcatttgat ttgaaataaa gatacaatca tattgatgat ttgagtttta 28500
aaaaaataaa gaatcactta cttgaaatct gataccaggt ctctgtccat gttttctgcc 28560
aacaccactt cactcccctc ttcccagctc tggtactgca ggccccggcg ggctgcaaac 28620
ttcctccaca cgctgaaggg gatgtcaaat tcctcctgtc cctcaatctt cattttatct 28680
tctatcagat gtccaaaaag cgcgtccggg tggatgatga cttcgacccc gtctacccct 28740
acgatgcaga caacgcaccg accgtgccct tcatcaaccc cccttcgtc tcttcagatg 28800
gattccaaga gaagcccctg gggtgctgt ccctgcgact ggccgacccc gtcaccacca 28860
agaacgggga aatcaccctc aagctgggag agggggtgga cctcgactcc tcgggaaaac 28920
tcatctccaa cacggccacc aaggccgccg cccctctcag tttttccaac aacaccattt 28980
cccttaacat ggataccccct ttttacacca aagatggaaa attaaccatg caggtcactg 29040
caccgctaaa gttagcaaac acagccatat tgaacacact agccatggca tatggaaatg 29100
gattagggct aagcaacaac gctcttaccg ttcagttaca atctccactc acctttaaca 29160
acagcaaggt tgctatcaac ctggaaaatg gaccactaaa cgtgacatca aatagactta 29220
gcattaattg caagaggggt gtctatgtca ccaccacagg agatgcaatc gaaaccaaca 29280
taagttggcc aaatgctatt aaatttatag gaaatgcaat gggtgtcaat attgatacaa 29340
acaaaggctt gcaatttggc accaccagca ctgtcacaga tgtgaccgat gctttcccca 29400
tacaagtcaa acttggggct ggtcttgcat ttgatagcac tggagctatt gttgcatgga 29460
acaaagagga tgacagtctc actttgtgga ctacaccaga tccatctcca aattgcaaga 29520
tagcatctga caaagatgct aaactcacac tttgcttgac aaagtgtgga agtcaaattc 29580
tgggtactgt gactgtattg gcagtgaata atggaagtct caacccaatc acaaacacag 29640
taagcactgc ccttgtatca cttaaattcg acgccaatgg agcactcttg gaaaaatcaa 29700
ccctaaacag agaatattgg aactacagac aaggagatct cattccaggt acaccatata 29760
cccatgcagt aggtttcatg cccaacaaga aagcctaccc taaaaacaca actgcagctt 29820
ccaaaagcca cattgtgggg gacgtctatc tagacgggga tgtagataag cccctatctc 29880
tcataatcac ttttaatgaa actgatgatg aatcatgtga ctattgcatg aactttcaat 29940
ggaaatgggg tgctgatcaa tacaaggaca aaacactcgc taccagctcc ttcaccttct 30000
cctacatcgc ccaagaatga acactgtatc ccaccctgca tgccaaccct tcccacccca 30060
ctctgtctgt ggaaaaaact ctgaaacaca aaataaaata aagttcaagt gttttattga 30120
ttcaacagtt ttacaggatt cgagcagtta tttttcctcc accctcccag gacatggaat 30180
acaccaccct ctccccccgc acagccttga acatctgaat gccattggtg atggacatgc 30240
ttttggtctc cacgttccac acagtttcag agcgagccag tctcgggtcg gtcagggaga 30300
tgaaaccctc cgggcactcc cgcatctgca cctcacagct caacagctga ggattgtcct 30360
cggtggtcgg gatcacggtt atctggaaga agcagaagag cggcggtggg aatcatagtc 30420
cgcgaacggg atcggccggt ggtgccgcat caggccccgc agcagtcgct gccgccgccg 30480
ctccgtcaag ctgctgctca gggggtccgg gtccagggac tccctcagca tgatgcccac 30540
ggccctcagc atcagtcgtc tggtgcggcg ggcgcagcag cgcatgcgga tctcgctcag 30600
gtcgctgcag tacgtgcaac acaggaccac caggttgttc aacagtccat agttcaacac 30660
gctccagccg aaactcatcg cgggaaggat gctacccacg tggccgtcgt accagatcct 30720
caggtaaatc aagtggcgcc ccctccagaa cacgctgccc acgtacatga tctccttggg 30780
catgtggcgg ttcaccacct cccggtacca catcaccctt tggttgaaca tgcagccccg 30840
gatgatcctg cggaaccaca gggccagcac cgccccgccc gccatgcagc gaagagaccc 30900
cgggtcccga caatggcaat ggaggaccca ccgctcgtac ccgtggatca tctgggagct 30960
gaacaagtct atgttggcac agcacaggca cacgctcatg catctcttca gcactctcag 31020
ctcctcgggg gtcaaaacca tatcccaggg cacggggaac tcttgcagga cagcgaaccc 31080
cgcagaacag ggcaatcctc gcacataact tacattgtgc atggacaggg tatcgcaatc 31140
aggcagcacc gggtgatcct ccaccagaga agcgcgggtc tcggtctcct cacagcgtgg 31200
taagggggcc ggccgatacg ggtgatggcg ggacgcggct gatcgtgttc gcgaccgtgt 31260
catgatgcag ttgctttcgg acattttcgt acttgctgta gcagaacctg gtccgggcgc 31320
tgcacaccga tcgccggcgg cggtctcggc gcttggaacg ctcggtgttg aaattgtaaa 31380
acagccactc tctcagaccg tgcagcagat ctagggcctc aggagtgatg aagatcccat 31440
catgcctgat ggctctgatc acatcgacca ccgtggaatg ggccagaccc agccagatga 31500
tgcaattttg ttgggtttcg gtgacggcgg gggagggaag aacaggaaga accatgatta 31560
acttttaatc caaacggtct cggagtactt caaaatgaag atcgcggaga tggcacctct 31620
cgcccccgct gtgttggtgg aaaataacag ccaggtcaaa ggtgatacgg ttctcgagat 31680
gttccacggt ggcttccagc aaagcctcca cgcgcacatc cagaaacaag acaatagcga 31740
aagcgggagg gttctctaat tcctcaatca tcatgttaca ctcctgcacc atccccagat 31800
aattttcatt tttccagcct tgaatgattc gaactagttc ctgaggtaaa tccaagccag 31860
tcatgataaa gagctcgcgc agagcgccct ccaccggcat tcttaagcac accctcataa 31920
ttccaagata ttctgctcct ggttcacctg cagcagattg acaagcggaa tatcaaaatc 31980
tctgccgcga tccctgagct cctccctcag caataactgt aagtactctt tcatatcctc 32040
tccgaaattt ttagccatag gaccaccagg aataagatta gggcaagcca cagtacagat 32100
aaaccgaagt cctccccagt gagcattgcc aaatgcaaga ctgctataag catgctggct 32160
agacccggtg atatcttcca gataactgga cagaaaatca cccaggcaat ttttaagaaa 32220
atcaacaaaa gaaaaatcct ccaggtgcac gtttagggcc tcgggaacaa cgatggagta 32280

```
aacgcaagcg gtgcgttcca gcatggttag ttagctgatc tgtaaaaaaa caaaaaataa  32340

aacattaaac catgctagcc tggcgaacag gtgggtaaat cgttctctcc agcaccaggc  32400

aggccacggg gtctccggcg cgaccctcgt aaaaattgtc gctatgattg aaaaccatca  32460

cagagagacg ttcccggtgg ccggcgtgaa tgattcgaca agatgaatac accccggaa   32520

cattggcgtc cgcgagtgaa aaaaagcgcc cgaggaagca ataaggcact acaatgctca  32580

gtctcaagtc cagcaaagcg atgccatgcg gatgaagcac aaaattctca ggtgcgtaca  32640

aaatgtaatt actcccctcc tgcacaggca gcaaagcccc cgatccctcc aggtacacat  32700

acaaagcctc agcgtccata gcttaccgag cagcagcaca caacaggcgc aagagtcaga  32760

gaaaggctga gctctaacct gtccacccgc tctctgctca atatatagcc cagatctaca  32820

ctgacgtaaa ggccaaagtc taaaaatacc cgccaaataa tcacacacgc ccaacacacg  32880

cccagaaacc ggtgacacac tcagaaaaat acgcgcactt cctcaaacgc ccaaactgcc  32940

gtcatttccg ggttcccacg ctacgtcatc agaattcgac tttcaaattc cgtcgaccgt  33000

taaaaacgtc acccgccccg cccctaacgg tcgcccgtct ctcggccaat cacagccccg  33060

catccccaaa ttcaaacacc tcatttgcat attaacgcgc accaaaagtt tgaggtatat  33120

tattgatgat gttaattaat tggttc                                         33146
```

<210> SEQ ID NO 5
<211> LENGTH: 328
<212> TYPE: DNA
<213> ORGANISM: Artificial Sequence
<220> FEATURE:
<223> OTHER INFORMATION: Synthesized

<400> SEQUENCE: 5

```
cttgcatttc tcagtcctaa acagggtaat gggctggggc tgaatcacat gaaggcaagg     60

tcagattttt attattatgc acatctagct tgaaaatttt ccattaagtc aattacagtg    120

aaaaacctca cctggtattg aatgcttgcc ttgtatgtct ggctattctg tgttttttatt    180

ttaaaattat aatatcaaaa tatttgtgtt ataaaatatt ctaactatgg aggccataaa    240

caagaagact aaagttctct cctttcagcc ttctgtacac atttcttctc aagcactggt    300

ttatgcatgt atactatatg caaaagtg                                       328
```

<210> SEQ ID NO 6
<211> LENGTH: 1775
<212> TYPE: DNA
<213> ORGANISM: Artificial Sequence
<220> FEATURE:
<223> OTHER INFORMATION: Synthesized

<400> SEQUENCE: 6

```
aggagcggca gggatacaag tcctggcggg ggcacaaaaa cgccatcgtc tcctgcttgc     60

aagcctgcgg gggcaacatc tccttcaccc ggcgctacct gctcttccac cgcggggtga    120

acttcccccg caacatcttg cattactacc gtcacctcca cagcccctac tactgtttcc    180

aagaagaggc agaaacccag cagcagcagc agaaaaccag cgacagctag aaaatccaca    240

gcggcggcgg caggtggact gaggatcgcg gcgaacgagc cagcgcagac ccgggagctg    300

aggaaccgga tctttcccac cctctatgcc atcttccagc agagtcgggg gcaggagcag    360

gaactgaaag tcaagaaccg ttctctgcgc tcgctcaccc gcagttgtct gtatcacaag    420

agcgaagacc aacttcagcg cactctcgag gacgccgagg ctctcttcaa caagtactgc    480
```

gcgctcactc ttaaagagta gcccgcgccc gcccacacac ggaaaaaggc gggaattacg 540
tcaccacctg cgcccttcgc ccgaccatca tgagcaaaga gattcccacg ccttacatgt 600
ggagctacca gccccagatg ggcctggccg ccggcgccgc ccaggactac tccacccgca 660
tgaactggct cagtgccggg cccgcgatga tctcacgggt gaatgacatc cgcgcccacc 720
gaaaccagat actcctagaa cagtcagcga tcaccaccac gccccgccat caccttaatc 780
cgcgtaattg gcccgccgcc ctggtgtacc aggaaattcc ccagcccacg accgtactac 840
ttccgcgaga cgcccaggcc gaagtccagc tgactaactc aggtgtccag ctggccggcg 900
gcgccgccct gtgtcgtcac cgccccgctc agggtataaa gcggctggtg atccgaggca 960
gaggcacaca gctcaacgac gaggtggtga gctcttcgct gggtctgcga cctgacggag 1020
tcttccaact cgccggatcg gggagatctt ccttcacgcc tcgtcaggcc gtcctgactt 1080
tggagagttc gtcctcgcag ccccgctcgg gcggcatcgg cactctccag ttcgtggagg 1140
agttcactcc ctcggtctac ttcaacccct tctccggctc cccggccac tacccggacg 1200 agttcatccc gaacttcgac gccatcagcg agtcggtgga cggctacgat tgatcacccc 1260
cttatccagt gaaataaaga tcatattgat gatgatttaa ataaaaaaaa aaaaaaaata 1320
atcatttgat ttgaaataaa gatacaatca tattgatgat ttgagtttta aaaaaataaa 1380
gaatcactta cttgaaatct gataccaggt ctctgtccat gttttctgcc aacaccactt 1440
cactcccctc ttcccagctc tggtactgca ggccccggcg ggctgcaaac ttcctccaca 1500
cgctgaaggg gatgtcaaat tcctcctgtc cctcaatctt cattttatct tctatcagat 1560
gtccaaaaag cgcgtccggg tggatgatga cttcgacccc gtctacccct acgatgcaga 1620
caacgcaccg accgtgccct tcatcaaccc ccccttcgtc tcttcagatg gattccaaga 1680
gaagcccctg gggtgctgt ccctgcgact ggccgacccc gtcaccacca agaacgggga 1740
aatcaccctc aagctgggag agggggtgga cctcg 1775

<210> SEQ ID NO 7
<211> LENGTH: 639
<212> TYPE: DNA
<213> ORGANISM: Artificial Sequence
<220> FEATURE:
<223> OTHER INFORMATION: Synthesized

<400> SEQUENCE: 7
atgaacacct cacagtggat aaccaaagac aatggaactg ataagacata cagttttgga 60
aatgctccag tcagaggatt ggacattaca gaagagggtc tccaaatagg aaccgatgag 120
tcagggggtg aaagcaagaa aatttttgca gacaaaacct atcagcctga acctcagctt 180
ggagatgagg aatggcatga tactattgga gctgaagaca agtatggagg cagagcgctt 240
aaacctgcca ccaacatgaa accctgctat gggtctttcg ccaagccaac taatgctaag 300
ggaggtcagg ctaaaagcag aaccaaggac gatggcacta ctgagcctga tattgacatg 360
gccttctttg acgatcgcag tcagcaagct agtttcagtc cagaacttgt tttgtatact 420
gagaatgtcg atctggacac cccggatacc cacattattt acaaacctgg cactgatgaa 480
acaagttctt ctttcaactt gggtcagcag tccatgccca acagacccaa ctacattggg 540
ttcagagaca actttatcgg tctcatgtac tacaacagca ctggcaatat gggtgtgctg 600
gctggacagg cctcccagct gaatgctgtg gtggactaa 639

<210> SEQ ID NO 8
<211> LENGTH: 3822

<212> TYPE: DNA
<213> ORGANISM: Artificial Sequence
<220> FEATURE:
<223> OTHER INFORMATION: Synthesized

<400> SEQUENCE: 8
atgtttgttt ttcttgtttt attgccacta gtctctagtc agtgtgttaa tcttacaacc 60
agaactcaat tacccccctgc atacactaat tctttcacac gtggtgttta ttaccctgac 120
aaagttttca gatcctcagt tttacattca actcaggact tgttcttacc tttcttttcc 180
aatgttactt ggttccatgc tatacatgtc tctgggacca atggtactaa gaggtttgat 240
aaccctgtcc taccatttaa tgatggtgtt tattttgctt ccactgagaa gtctaacata 300
ataagaggct ggatttttgg tactacttta gattcgaaga cccagtccct acttattgtt 360
aataacgcta ctaatgttgt tattaaagtc tgtgaatttc aattttgtaa tgatccattt 420
ttgggtgttt attaccacaa aaacaacaaa agttggatgg aaagtgagtt cagagtttat 480
tctagtgcga ataattgcac ttttgaatat gtctctcagc cttttcttat ggaccttgaa 540
ggaaaacagg gtaatttcaa aaatcttagg gaatttgtgt ttaagaatat tgatggttat 600
tttaaaatat attctaagca cacgcctatt aatttagtgc gtgatctccc tcagggtttt 660
tcggctttag aaccattggt agatttgcca ataggtatta acatcactag gtttcaaact 720
ttacttgctt tacatagaag ttatttgact cctggtgatt cttcttcagg ttggacagct 780
ggtgctgcag cttattatgt gggttatctt caacctagga cttttctatt aaaatataat 840
gaaaatggaa ccattacaga tgctgtagac tgtgcacttg accctctctc agaaacaaag 900
tgtacgttga aatccttcac tgtagaaaaa ggaatctatc aaacttctaa ctttagagtc 960
caaccaacag aatctattgt tagatttcct aatattacaa acttgtgccc ttttggtgaa 1020
gtttttaacg ccaccagatt tgcatctgtt tatgcttgga acaggaagag aatcagcaac 1080
tgtgttgctg attattctgt cctatataat tccgcatcat tttccacttt taagtgttat 1140
ggagtgtctc ctactaaatt aaatgatctc tgctttacta atgtctatgc agattcattt 1200
gtaattagag gtgatgaagt cagacaaatc gctccagggc aaactggaaa gattgctgat 1260
tataattata aattaccaga tgattttaca ggctgcgtta tagcttggaa ttctaacaat 1320
cttgattcta aggttggtgg taattataat tacctgtata gattgtttag gaagtctaat 1380
ctcaaacctt ttgagagaga tatttcaact gaaatctatc aggccggtag cacaccttgt 1440
aatggtgttg aaggttttaa ttgttacttt cctttacaat catatggttt ccaacccact 1500
aatggtgttg gttaccaacc atacagagta gtagtacttt cttttgaact tctacatgca 1560
ccagcaactg tttgtggacc taaaaagtct actaatttgg ttaaaaacaa atgtgtcaat 1620
ttcaacttca atggtttaac aggcacaggt gttcttactg agtctaacaa aaagtttctg 1680
cctttccaac aatttggcag agacattgct gacactactg atgctgtccg tgatccacag 1740
acacttgaga ttcttgacat tacaccatgt tcttttggtg gtgtcagtgt tataacacca 1800
ggaacaaata cttctaacca ggttgctgtt ctttatcagg atgttaactg cacagaagtc 1860
cctgttgcta ttcatgcaga tcaacttact cctacttggc gtgtttattc tacaggttct 1920
aatgtttttc aaacacgtgc aggctgttta ataggggctg aacatgtcaa caactcatat 1980
gagtgtgaca tacccattgg tgcaggtata tgcgctagtt atcagactca gactaattct 2040
cctcggcggg cacgtagtgt agctagtcaa tccatcattg cctacactat gtcacttggt 2100
gcagaaaatt cagttgctta ctctaataac tctattgcca tacccacaaa ttttactatt 2160
agtgttacca cagaaattct accagtgtct atgaccaaga catcagtaga ttgtacaatg 2220
tacatttgtg gtgattcaac tgaatgcagc aatcttttgt tgcaatatgg cagtttttgt 2280
acacaattaa accgtgcttt aactggaata gctgttgaac aagacaaaaa cacccaagaa 2340
gtttttgcac aagtcaaaca aatttacaaa acaccaccaa ttaaagattt tggtggtttt 2400
aatttttcac aaatattacc agatccatca aaaccaagca agaggtcatt tattgaagat 2460
ctacttttca acaaagtgac acttgcagat gctggcttca tcaaacaata tggtgattgc 2520
cttggtgata ttgctgctag agacctcatt tgtgcacaaa agtttaacgg ccttactgtt 2580
ttgccacctt tgctcacaga tgaaatgatt gctcaataca cttctgcact gttagcgggt 2640
acaatcactt ctggttggac ctttggtgca ggtgctgcat tacaaatacc atttgctatg 2700
caaatggctt ataggtttaa tggtattgga gttacacaga atgttctcta tgagaaccaa 2760
aaattgattg ccaaccaatt taatagtgct attggcaaaa ttcaagactc actttcttcc 2820
acagcaagtg cacttggaaa acttcaagat gtggtcaacc aaaatgcaca agctttaaac 2880
acgcttgtta aacaacttag ctccaatttt ggtgcaattt caagtgtttt aaatgatatc 2940
ctttcacgtc ttgacaaagt tgaggctgaa gtgcaaattg ataggttgat cacaggcaga 3000
cttcaaagtt tgcagacata tgtgactcaa caattaatta gagctgcaga aatcagagct 3060
tctgctaatc ttgctgctac taaaatgtca gagtgtgtac ttggacaatc aaaaagagtt 3120
gatttttgtg gaaagggcta tcatcttatg tccttccctc agtcagcacc tcatggtgta 3180
gtcttcttgc atgtgactta tgtccctgca caagaaaaga acttcacaac tgctcctgcc 3240
atttgtcatg atggaaaagc acactttcct cgtgaaggtg tctttgtttc aaatggcaca 3300
cactggtttg taacacaaag gaatttttat gaaccacaaa tcattactac agacaacaca 3360
tttgtgtctg gtaactgtga tgttgtaata ggaattgtca acaacacagt ttatgatcct 3420
ttgcaacctg aattagactc attcaaggag gagttagata aatattttaa gaatcataca 3480
tcaccagatg ttgatttagg tgacatctct ggcattaatg cttcagttgt aaacattcaa 3540
aaagaaattg accgcctcaa tgaggttgcc aagaatttaa atgaatctct catcgatctc 3600
caagaacttg gaaagtatga gcagtatata aaatggccat ggtacatttg gctaggtttt 3660
atagctggct tgattgccat agtaatggtg acaattatgc tttgctgtat gaccagttgc 3720
tgtagttgtc tcaagggctg ttgttcttgt ggatcctgct gcaaatttga tgaagacgac 3780
tctgagccag tgctcaaagg agtcaaatta cattacacat aa 3822

<210> SEQ ID NO 9
<211> LENGTH: 27
<212> TYPE: DNA
<213> ORGANISM: Artificial Sequence
<220> FEATURE:
<223> OTHER INFORMATION: Synthesized

<400> SEQUENCE: 9
ataaccaaag acaatggaac tgataag 27

<210> SEQ ID NO 10
<211> LENGTH: 24
<212> TYPE: DNA
<213> ORGANISM: Artificial Sequence
<220> FEATURE:
<223> OTHER INFORMATION: Synthesized

<400> SEQUENCE: 10
gagtcagggg gtgaaagcaa gaaa 24

<210> SEQ ID NO 11
<211> LENGTH: 27
<212> TYPE: DNA
<213> ORGANISM: Artificial Sequence
<220> FEATURE:
<223> OTHER INFORMATION: Synthesized

<400> SEQUENCE: 11
catgatacta ttggagctga agacaag 27

<210> SEQ ID NO 12
<211> LENGTH: 18
<212> TYPE: DNA
<213> ORGANISM: Artificial Sequence
<220> FEATURE:
<223> OTHER INFORMATION: Synthesized

<400> SEQUENCE: 12
aaggacgatg gcactact 18

<210> SEQ ID NO 13
<211> LENGTH: 15
<212> TYPE: DNA
<213> ORGANISM: Artificial Sequence
<220> FEATURE:
<223> OTHER INFORMATION: Synthesized

<400> SEQUENCE: 13
agtcagcaag ctagt 15

<210> SEQ ID NO 14
<211> LENGTH: 18
<212> TYPE: DNA
<213> ORGANISM: Artificial Sequence
<220> FEATURE:
<223> OTHER INFORMATION: Synthesized

<400> SEQUENCE: 14
ggcactgatg aaacaagt 18

<210> SEQ ID NO 15
<211> LENGTH: 54
<212> TYPE: DNA
<213> ORGANISM: Artificial Sequence
<220> FEATURE:
<223> OTHER INFORMATION: Synthesized

<400> SEQUENCE: 15
acagcaaatg ctacagagtg ggaatctgat acctctgtca ataatgctaa tgag 54

<210> SEQ ID NO 16
<211> LENGTH: 1126
<212> TYPE: DNA
<213> ORGANISM: Artificial Sequence
<220> FEATURE:
<223> OTHER INFORMATION: Synthesized

<400> SEQUENCE: 16
ttaatagtaa tcaattacgg ggtcattagt tcatagccca tatatggagt tccgcgttac 60
ataacttacg gtaaatggcc cgcctggctg accgcccaac gacccccgcc cattgacgtc 120
aataatgacg tatgttccca tagtaacgcc aatagggact ttccattgac gtcaatgggt 180
ggagtattta cggtaaactg cccacttggc agtacatcaa gtgtatcata tgccaagtac 240

```
gccccctatt gacgtcaatg acggtaaatg gcccgcctgg cattatgccc agtacatgac    300

cttatgggac tttcctactt ggcagtacat ctacgtatta gtcatcgcta ttaccatggt    360

gatgcggttt tggcagtaca tcaatgggcg tggatagcgg tttgactcac ggggatttcc    420

aagtctccac cccattgacg tcaatgggag tttgttttgg caccaaaatc aacgggactt    480

tccaaaatgt cgtaacaact ccgccccatt gacgcaaatg ggcggtaggc gtgtacggtg    540

ggaggtctat ataagcagag ctcgtcgacg agctcgttta gtgaaccgtc agatcgcctg    600

gagacgccat ccacgctgtt ttgacctcca tagaagacac cgggaccgat ccagcctccg    660

cggccgggaa cggtgcattg gaacgcggat tccccgtgcc aagagtgacg taagtaccgc    720

ctatagagtc tataggccca ccccccttggc ttcacttgag gtgtggcagg cttgagatct    780

ggccatacac ttgagtgaca atgacatcca ctttgccttt ctctccacag gtgtccactc    840

ccaggtccaa ctgcagccgg tacctaatac gactcactat acggatccct gatcactgca    900

gaattcgata tcaagcttat cgattgcggc cgctctcgag tctagctagt ctagactagc    960

tagaaagatc cgggaacttg tttattgcag cttataatgg ttacaaataa agcaatagca   1020

tcacaaattt cacaaataaa gcattttttt cactgcattc tagttgtggt ttgtccaaac   1080

tcatcaatgt atcttatcat gtctggatcg gtgatcaccg atcccg                  1126
```

<210> SEQ ID NO 17
<211> LENGTH: 597
<212> TYPE: DNA
<213> ORGANISM: Artificial Sequence
<220> FEATURE:
<223> OTHER INFORMATION: Synthesized

<400> SEQUENCE: 17

```
tcgacaatca acctctggat tacaaaattt gtgaaagatt gactggtatt cttaactatg     60

ttgctccttt tacgctatgt ggatacgctg ctttaatgcc tttgtatcat gctattgctt    120

cccgtatggc tttcattttc tcctccttgt ataaatcctg gttgctgtct ctttatgagg    180

agttgtggcc cgttgtcagg caacgtggcg tggtgtgcac tgtgtttgct gacgcaaccc    240

ccactggttg gggcattgcc accacctgtc agctcctttc cgggactttc gctttccccc    300

tccctattgc cacggcggaa ctcatcgccg cctgccttgc ccgctgctgg acaggggctc    360

ggctgttggg cactgacaat tccgtggtgt tgtcggggaa gctgacgtcc tttccatggc    420

tgctcgcctg tgttgccacc tggattctgc gcgggacgtc cttctgctac gtcccttcgg    480

ccctcaatcc agcggacctt ccttcccgcg gcctgctgcc ggctctgcgg cctcttccgc    540

gtcttcgcct tcgccctcag acgagtcgga tctccctttg ggccgcctcc ccgcctg       597
```

<210> SEQ ID NO 18
<211> LENGTH: 53
<212> TYPE: DNA
<213> ORGANISM: Artificial Sequence
<220> FEATURE:
<223> OTHER INFORMATION: Synthesized

<400> SEQUENCE: 18

```
tttgaggtat attattgatg atgttaatta ttggttccac ttgagcgtca gac            53
```

<210> SEQ ID NO 19
<211> LENGTH: 53
<212> TYPE: DNA
<213> ORGANISM: Artificial Sequence
<220> FEATURE:
<223> OTHER INFORMATION: Synthesized

<400> SEQUENCE: 19
tttgaggtat attattgatg atgttaatta aagacgaaag ggcctcgttt gta 53

<210> SEQ ID NO 20
<211> LENGTH: 24
<212> TYPE: DNA
<213> ORGANISM: Artificial Sequence
<220> FEATURE:
<223> OTHER INFORMATION: Synthesized

<400> SEQUENCE: 20
catcatcaat aatatacctc aaac 24

<210> SEQ ID NO 21
<211> LENGTH: 50
<212> TYPE: DNA
<213> ORGANISM: Artificial Sequence
<220> FEATURE:
<223> OTHER INFORMATION: Synthesized

<400> SEQUENCE: 21
ctttgctggg aagccaccgt gggaggatcc aagtaaacac acatgtggca 50

<210> SEQ ID NO 22
<211> LENGTH: 20
<212> TYPE: DNA
<213> ORGANISM: Artificial Sequence
<220> FEATURE:
<223> OTHER INFORMATION: Synthesized

<400> SEQUENCE: 22
tccacggtgg cttccagcaa 20

<210> SEQ ID NO 23
<211> LENGTH: 24
<212> TYPE: DNA
<213> ORGANISM: Artificial Sequence
<220> FEATURE:
<223> OTHER INFORMATION: Synthesized

<400> SEQUENCE: 23
catcatcaat aatatacctc aaac 24

<210> SEQ ID NO 24
<211> LENGTH: 19
<212> TYPE: DNA
<213> ORGANISM: Artificial Sequence
<220> FEATURE:
<223> OTHER INFORMATION: Synthesized

<400> SEQUENCE: 24
tcattcaccg cctcctcgt 19

<210> SEQ ID NO 25
<211> LENGTH: 20
<212> TYPE: DNA
<213> ORGANISM: Artificial Sequence
<220> FEATURE:
<223> OTHER INFORMATION: Synthesized

<400> SEQUENCE: 25
ggacctgcga cccgatcatt 20

<210> SEQ ID NO 26

<211> LENGTH: 85
<212> TYPE: DNA
<213> ORGANISM: Artificial Sequence
<220> FEATURE:
<223> OTHER INFORMATION: Synthesized

<400> SEQUENCE: 26
taatacgact cactatagat tcaccgcctc ctcgtttttt agagctaaaa tagcaaggct 60
agtccgtatc aacttgaaaa gtttt 85

<210> SEQ ID NO 27
<211> LENGTH: 33
<212> TYPE: DNA
<213> ORGANISM: Artificial Sequence
<220> FEATURE:
<223> OTHER INFORMATION: Synthesized

<400> SEQUENCE: 27
taatacgact cactatagat tcaccgcctc ctc 33

<210> SEQ ID NO 28
<211> LENGTH: 33
<212> TYPE: DNA
<213> ORGANISM: Artificial Sequence
<220> FEATURE:
<223> OTHER INFORMATION: Synthesized

<400> SEQUENCE: 28
ttctagctct aaaacaacga ggaggcggtg aat 33

<210> SEQ ID NO 29
<211> LENGTH: 33
<212> TYPE: DNA
<213> ORGANISM: Artificial Sequence
<220> FEATURE:
<223> OTHER INFORMATION: Synthesized

<400> SEQUENCE: 29
taatacgact cactatagac ctgcgacccg atc 33

<210> SEQ ID NO 30
<211> LENGTH: 33
<212> TYPE: DNA
<213> ORGANISM: Artificial Sequence
<220> FEATURE:
<223> OTHER INFORMATION: Synthesized

<400> SEQUENCE: 30
ttctagctct aaaacaatga tcgggtcgca ggt 33

<210> SEQ ID NO 31
<211> LENGTH: 74
<212> TYPE: RNA
<213> ORGANISM: Artificial Sequence
<220> FEATURE:
<223> OTHER INFORMATION: Synthesized

<400> SEQUENCE: 31
gauucaccgc cuccucguug uuuuuagaaa uagcaaguua aaauaaggcu agucacaacu 60
ugaaaaaagu guuu 74

<210> SEQ ID NO 32
<211> LENGTH: 75
<212> TYPE: RNA
<213> ORGANISM: Artificial Sequence

```
<220> FEATURE:
<223> OTHER INFORMATION: Synthesized

<400> SEQUENCE: 32

gaccugcgac ccgaucauug uuuuuagaau agcaaguuaa aauaaggcua guuucaacuu     60

gaaaaaaagg uguuu                                                      75


<210> SEQ ID NO 33
<211> LENGTH: 43
<212> TYPE: DNA
<213> ORGANISM: Artificial Sequence
<220> FEATURE:
<223> OTHER INFORMATION: Synthesized

<400> SEQUENCE: 33

atgtgcccga gaacccccaa ccttgcattt ctcagtccta aac                       43


<210> SEQ ID NO 34
<211> LENGTH: 45
<212> TYPE: DNA
<213> ORGANISM: Artificial Sequence
<220> FEATURE:
<223> OTHER INFORMATION: Synthesized

<400> SEQUENCE: 34

cccgttgcag gacaacacca aatcactttg catatagtat acatg                     45


<210> SEQ ID NO 35
<211> LENGTH: 328
<212> TYPE: DNA
<213> ORGANISM: Artificial Sequence
<220> FEATURE:
<223> OTHER INFORMATION: Synthesized

<400> SEQUENCE: 35

cttgcatttc tcagtcctaa acagggtaat gggctggggc tgaatcacat gaaggcaagg     60

tcagattttt attattatgc acatctagct tgaaaatttt ccattaagtc aattacagtg    120

aaaaacctca cctggtattg aatgcttgcc ttgtatgtct ggctattctg tgtttttatt    180

ttaaaattat aatatcaaaa tatttgtgtt ataaaatatt ctaactatgg aggccataaa    240

caagaagact aaagttctct cctttcagcc ttctgtacac atttcttctc aagcactggt    300

ttatgcatgt atactatatg caaaagtg                                       328


<210> SEQ ID NO 36
<211> LENGTH: 20
<212> TYPE: DNA
<213> ORGANISM: Artificial Sequence
<220> FEATURE:
<223> OTHER INFORMATION: Synthesized

<400> SEQUENCE: 36

agcggcaggg atacaagtcc                                                 20


<210> SEQ ID NO 37
<211> LENGTH: 19
<212> TYPE: DNA
<213> ORGANISM: Artificial Sequence
<220> FEATURE:
<223> OTHER INFORMATION: Synthesized

<400> SEQUENCE: 37

gggaaatcac cctcaagct                                                  19
```

<210> SEQ ID NO 38
<211> LENGTH: 61
<212> TYPE: DNA
<213> ORGANISM: Artificial Sequence
<220> FEATURE:
<223> OTHER INFORMATION: Synthesized

<400> SEQUENCE: 38
aatacgactc actatagcgg cagggataca agtccgttta gagctaaaat agcaagggtt 60
t 61

<210> SEQ ID NO 39
<211> LENGTH: 126
<212> TYPE: DNA
<213> ORGANISM: Artificial Sequence
<220> FEATURE:
<223> OTHER INFORMATION: Synthesized

<400> SEQUENCE: 39
taatacgact cactatagga aatcaccctc aagctgtttt agagctaaaa tagcaagtta 60
aaatagggct agtccgtatc aacttgaaag gggcaccgag ggggcaccga gggtggtgtg 120
tttttt 126

<210> SEQ ID NO 40
<211> LENGTH: 33
<212> TYPE: DNA
<213> ORGANISM: Artificial Sequence
<220> FEATURE:
<223> OTHER INFORMATION: Synthesized

<400> SEQUENCE: 40
taatacgact cactatagcg gcagggatac aag 33

<210> SEQ ID NO 41
<211> LENGTH: 33
<212> TYPE: DNA
<213> ORGANISM: Artificial Sequence
<220> FEATURE:
<223> OTHER INFORMATION: Synthesized

<400> SEQUENCE: 41
ttctagctct aaaacggact tgtatccctg ccg 33

<210> SEQ ID NO 42
<211> LENGTH: 32
<212> TYPE: DNA
<213> ORGANISM: Artificial Sequence
<220> FEATURE:
<223> OTHER INFORMATION: Synthesized

<400> SEQUENCE: 42
taatacgact cactatagga aatcaccctc aa 32

<210> SEQ ID NO 43
<211> LENGTH: 33
<212> TYPE: DNA
<213> ORGANISM: Artificial Sequence
<220> FEATURE:
<223> OTHER INFORMATION: Synthesized

<400> SEQUENCE: 43
ttctagctct aaaacagctt gagggtgatt tcc 33

```
<210> SEQ ID NO 44
<211> LENGTH: 80
<212> TYPE: RNA
<213> ORGANISM: Artificial Sequence
<220> FEATURE:
<223> OTHER INFORMATION: Synthesized

<400> SEQUENCE: 44

gcggcaggga uacaaguccg uuuuuagaau agcaaguuaa aauaaggcua guccguuauc      60

aacuugaaaa aagaguguuu                                                  80


<210> SEQ ID NO 45
<211> LENGTH: 71
<212> TYPE: RNA
<213> ORGANISM: Artificial Sequence
<220> FEATURE:
<223> OTHER INFORMATION: Synthesized

<400> SEQUENCE: 45

gggaaaucac acccucaagc uguuuuagaa auagcaaguu aaaaagguua ucacaacuug      60

aaaaaguguu u                                                           71


<210> SEQ ID NO 46
<211> LENGTH: 20
<212> TYPE: DNA
<213> ORGANISM: Artificial Sequence
<220> FEATURE:
<223> OTHER INFORMATION: Synthesized

<400> SEQUENCE: 46

aggagcggca gggatacaag                                                  20


<210> SEQ ID NO 47
<211> LENGTH: 20
<212> TYPE: DNA
<213> ORGANISM: Artificial Sequence
<220> FEATURE:
<223> OTHER INFORMATION: Synthesized

<400> SEQUENCE: 47

tcaatcgtag ccgtccaccg                                                  20


<210> SEQ ID NO 48
<211> LENGTH: 46
<212> TYPE: DNA
<213> ORGANISM: Artificial Sequence
<220> FEATURE:
<223> OTHER INFORMATION: Synthesized

<400> SEQUENCE: 48

agtcggtgga cggctacgat tgatcacccc cttatcccag tgaaat                     46


<210> SEQ ID NO 49
<211> LENGTH: 17
<212> TYPE: DNA
<213> ORGANISM: Artificial Sequence
<220> FEATURE:
<223> OTHER INFORMATION: Synthesized

<400> SEQUENCE: 49

cgaggtccac cccctcc                                                     17


<210> SEQ ID NO 50
<211> LENGTH: 45
<212> TYPE: DNA
```

<213> ORGANISM: Artificial Sequence
<220> FEATURE:
<223> OTHER INFORMATION: Synthesized

<400> SEQUENCE: 50
tggatcggtg atcaccgatc ccgtttcaaa gtgtagatct gactc 45

<210> SEQ ID NO 51
<211> LENGTH: 49
<212> TYPE: DNA
<213> ORGANISM: Artificial Sequence
<220> FEATURE:
<223> OTHER INFORMATION: Synthesized

<400> SEQUENCE: 51
gttagctcac tcattaggca cccttaatta acatcatcaa taatatacc 49

<210> SEQ ID NO 52
<211> LENGTH: 21
<212> TYPE: DNA
<213> ORGANISM: Artificial Sequence
<220> FEATURE:
<223> OTHER INFORMATION: Synthesized

<400> SEQUENCE: 52
gggtgcctaa tgagtgagct a 21

<210> SEQ ID NO 53
<211> LENGTH: 20
<212> TYPE: DNA
<213> ORGANISM: Artificial Sequence
<220> FEATURE:
<223> OTHER INFORMATION: Synthesized

<400> SEQUENCE: 53
gacgtcaggt ggcacttttc 20

<210> SEQ ID NO 54
<211> LENGTH: 42
<212> TYPE: DNA
<213> ORGANISM: Artificial Sequence
<220> FEATURE:
<223> OTHER INFORMATION: Synthesized

<400> SEQUENCE: 54
cccgaaaagt gccacctgac gtctccgacc agccggatga gc 42

<210> SEQ ID NO 55
<211> LENGTH: 42
<212> TYPE: DNA
<213> ORGANISM: Artificial Sequence
<220> FEATURE:
<223> OTHER INFORMATION: Synthesized

<400> SEQUENCE: 55
ccccgtaatt gattactatt aatagagtga gtagtgttgg gg 42

<210> SEQ ID NO 56
<211> LENGTH: 23
<212> TYPE: DNA
<213> ORGANISM: Artificial Sequence
<220> FEATURE:
<223> OTHER INFORMATION: Synthesized

<400> SEQUENCE: 56
ttaatagtaa tcaattacgg ggt 23

-continued

```
<210> SEQ ID NO 57
<211> LENGTH: 20
<212> TYPE: DNA
<213> ORGANISM: Artificial Sequence
<220> FEATURE:
<223> OTHER INFORMATION: Synthesized

<400> SEQUENCE: 57

cgggatcggt gatcaccgat                                              20


<210> SEQ ID NO 58
<211> LENGTH: 49
<212> TYPE: DNA
<213> ORGANISM: Artificial Sequence
<220> FEATURE:
<223> OTHER INFORMATION: Synthesized

<400> SEQUENCE: 58

tatccagcac agtggcggcc gggccgctcg acaatcaacc tctggatta              49


<210> SEQ ID NO 59
<211> LENGTH: 68
<212> TYPE: DNA
<213> ORGANISM: Artificial Sequence
<220> FEATURE:
<223> OTHER INFORMATION: Synthesized

<400> SEQUENCE: 59

taaacgggcc ctctagactc gaggcggccg ccgggggggg gggggggggg gggggggggg     60

gggcgcca                                                           68


<210> SEQ ID NO 60
<211> LENGTH: 53
<212> TYPE: DNA
<213> ORGANISM: Artificial Sequence
<220> FEATURE:
<223> OTHER INFORMATION: Synthesized

<400> SEQUENCE: 60

tccctgatca ctgcagaatt cgatatcgcc accatgttcg ttttctggtg ctg          53


<210> SEQ ID NO 61
<211> LENGTH: 50
<212> TYPE: DNA
<213> ORGANISM: Artificial Sequence
<220> FEATURE:
<223> OTHER INFORMATION: Synthesized

<400> SEQUENCE: 61

attgtcgagc ggccgcaatc gataagcttt caggtgtagt gcagcttcac             50
```